United States Patent [19]

Yamauchi et al.

[11] Patent Number: 5,516,644
[45] Date of Patent: May 14, 1996

[54] ELECTROCHEMICAL IMMUNOCHROMATOGRAPHIC ASSAY

[75] Inventors: Tadakazu Yamauchi; Toshinori Kanamori; Masahiro Nobuhara, all of Tokyo, Japan

[73] Assignee: Mochida Pharmaceutical Co., Ltd., Tokyo, Japan

[21] Appl. No.: 243,095

[22] Filed: May 16, 1994

Related U.S. Application Data

[63] Continuation of Ser. No. 921,260, Jul. 29, 1992, abandoned.

[30] Foreign Application Priority Data

Jul. 29, 1991 [JP] Japan ................................. 3-188703

[51] Int. Cl.⁶ ..................... G01N 33/535; G01N 33/544; G01N 33/551; G01N 33/561
[52] U.S. Cl. .................. 435/7.9; 435/7.93; 435/7.94; 435/188; 435/810; 436/524; 436/528; 436/162; 436/169; 422/56; 422/61; 422/68.1; 422/82.01
[58] Field of Search ...................... 435/7.9, 7.93, 435/7.94, 188, 810, 970; 436/524, 528, 162, 169, 807; 422/56, 61, 68.1, 82.01

[56] References Cited

U.S. PATENT DOCUMENTS

| | | | |
|---|---|---|---|
| 4,956,275 | 9/1990 | Zuk et al. | 435/7.92 |
| 4,963,245 | 10/1990 | Weetall | 204/403 |
| 5,066,372 | 11/1991 | Weetall | 204/153.1 |

FOREIGN PATENT DOCUMENTS

| | | |
|---|---|---|
| 0032286 | 7/1981 | European Pat. Off. . |
| 0051183 | 5/1982 | European Pat. Off. . |
| 0066648 | 12/1982 | European Pat. Off. . |
| 0075379 | 3/1983 | European Pat. Off. . |
| 0100619 | 2/1984 | European Pat. Off. . |
| 0125139 | 11/1984 | European Pat. Off. . |
| 0125136 | 11/1984 | European Pat. Off. . |
| 0142301 | 5/1985 | European Pat. Off. . |
| 0150999 | 8/1985 | European Pat. Off. . |
| 0223541 | 5/1987 | European Pat. Off. . |
| 0236768 | 9/1987 | European Pat. Off. |
| 0323605 | 7/1989 | European Pat. Off. . |

(List continued on next page.)

OTHER PUBLICATIONS

D. J. Litman et al., *Analytical Biochemistry*, vol. 106, pp. 223–229, 1980 "Enzyme Channeling Immunoassay: A New Homogeneous Enzyme Immunoassay Technique".

M. J. Doyle et al., *Analytical Chemistry*, vol. 56, No. 13, pp. 2355–2360, 1984. "Enzyme–Linked Immunosorbent Assay with Electrochemical Detection for α1–Acid Glycoprotein".

G. A. Robinson et al., *Clinical Chemistry*, vol. 31, No. 9, pp. 1449–1452, 1985 "Bioelectrochemical Enzyme Immunoassay of Human Choriogonadotropin with Magnetic Electrodes".

*Primary Examiner*—James C. Housel
*Assistant Examiner*—Nancy J. Parsons
*Attorney, Agent, or Firm*—Birch, Stewart, Kolasch & Birch

[57] ABSTRACT

A specific binding assay process which is useful for quick qualitative or quantitative measurement and which can be used for various purposes, and a specific binding assay device suitable for the practice of the process, in which a substance to be assayed in a liquid test sample is determined qualitatively or quantitatively by developing the substance in a liquid test sample in a matrix, which comprises the steps of, for example:

allowing the substance to be assayed to react with a specific binding substance which has specific affinity for the substance to be assayed;

allowing a signal substance generator (a substance which competes with the substance to be assayed for the specific binding substance and which generates a signal) to chance its distribution in the matrix in response to the reaction of the above step, and;

detecting the resulting distributional changes at a detection means as changes of signals which are rate-limited by the mass transfer of a signal substance generated from the signal substance generator.

10 Claims, 17 Drawing Sheets

FOREIGN PATENT DOCUMENTS

| | | |
|---|---|---|
| 0352138 | 1/1990 | European Pat. Off. . |
| 0402126 | 12/1990 | European Pat. Off. . |
| 2729872 | 7/1977 | Germany . |
| 3227474 | 2/1983 | Germany . |
| 63-139248 | 6/1988 | Japan . |
| 2-112752 | 4/1990 | Japan . |
| 2-59424 | 12/1990 | Japan . |
| 2018986 | 10/1979 | United Kingdom . |
| 8505451 | 12/1985 | WIPO . |
| 8808534 | 11/1988 | WIPO . |
| 89/05454 | 6/1989 | WIPO . |

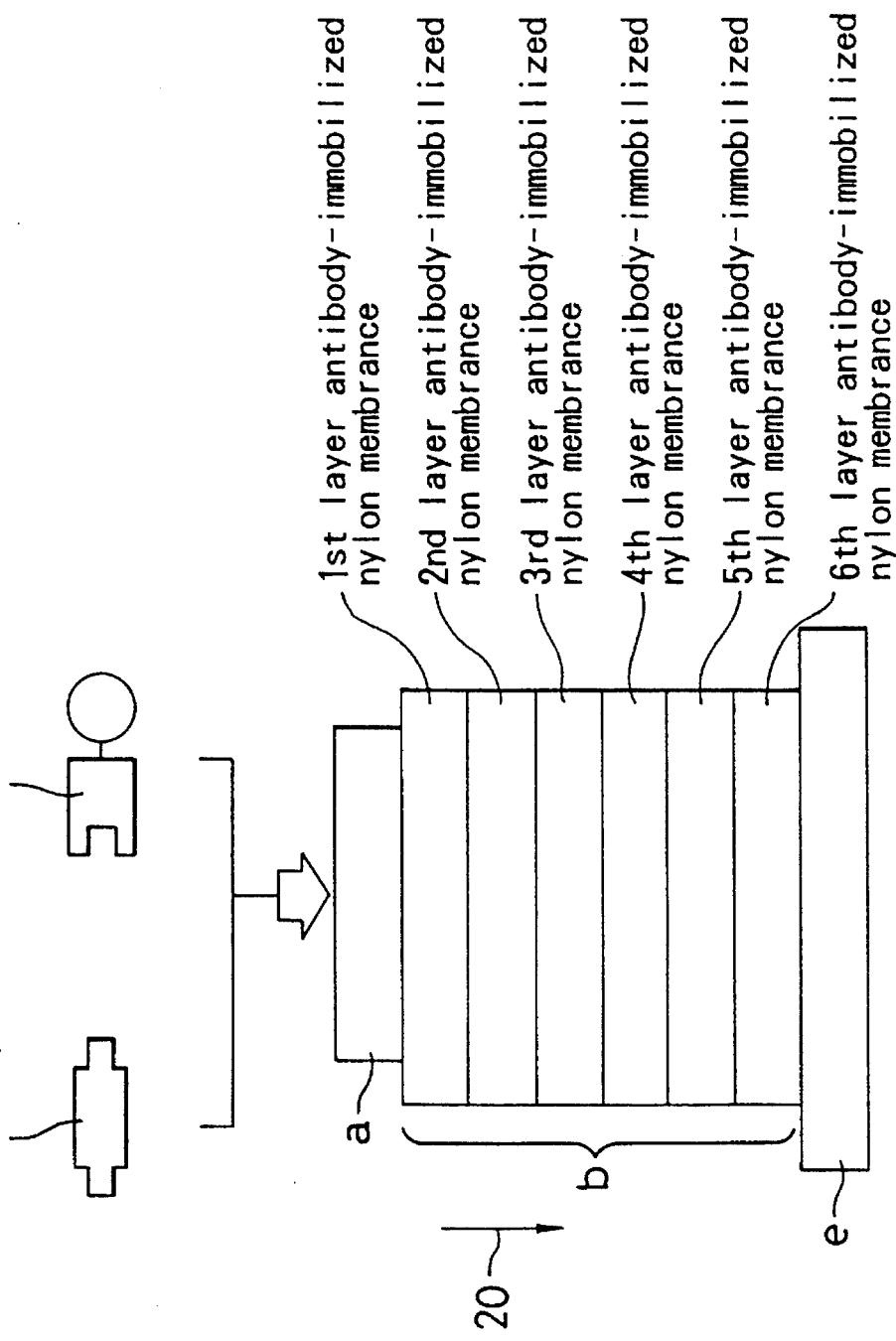

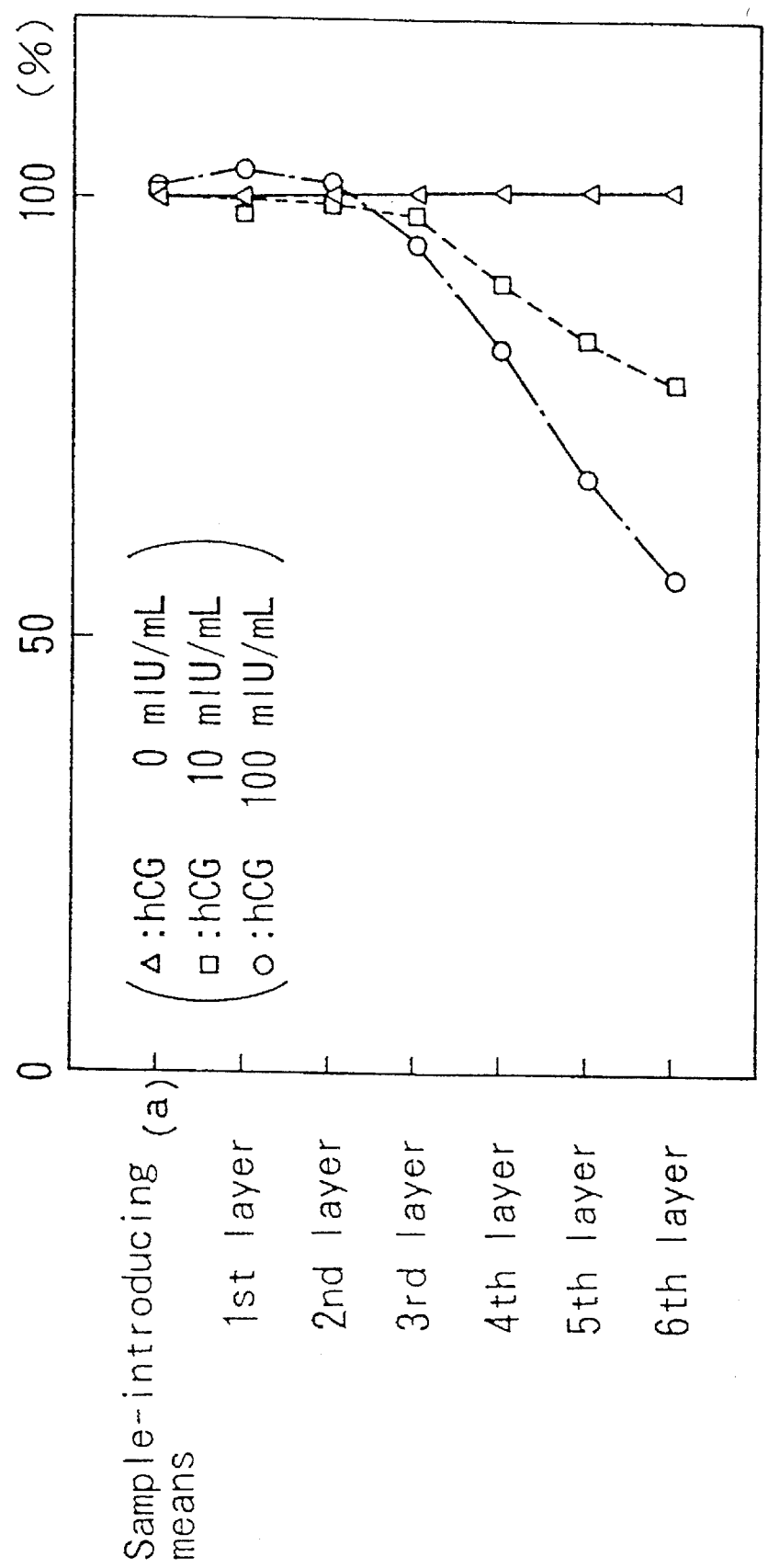

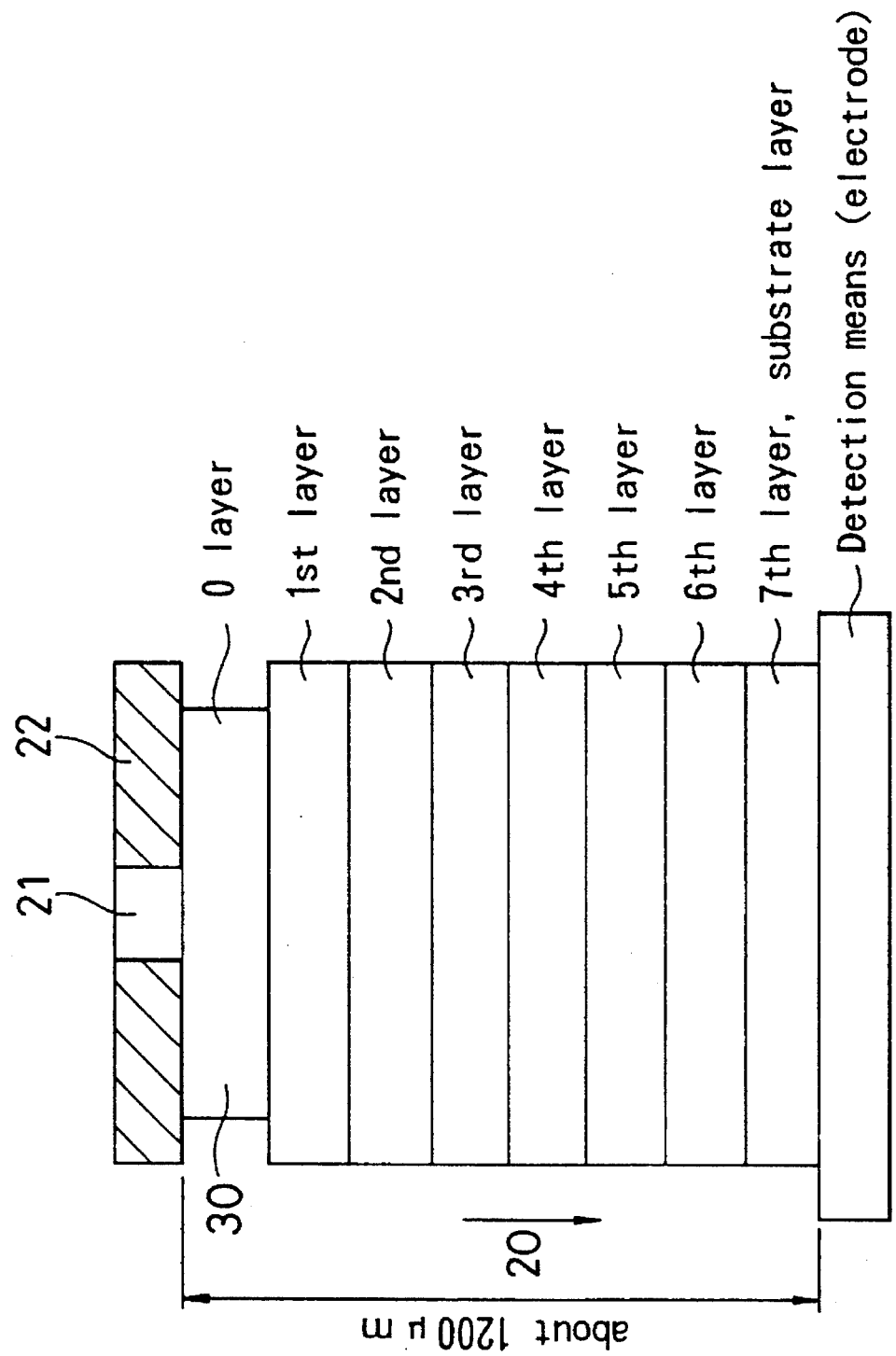

ELECTROCHEMICAL IMMUNOCHROMATOGRAPHIC ASSAY

This application is a continuation of application Ser. No. 07/921,260 filed on Jul. 29, 1992, now abandoned.

FIELD OF THE INVENTION

The present invention relates to a specific binding assay process for simple and quick qualitative or quantitative analysis of substances to be assayed in test samples and to a specific binding assay device suitable for the practice of the process.

More particularly, the present invention relates to an assay process and a device suitable for the practice of the process in which (1) distribution of a label (signal substance generator) correlative to a detection means can be changed in response to the concentration of a substance to be assayed, in a matrix where a specific binding substance which binds specifically to the substance to be assayed is immobilized or included, through at least one specific binding reaction of the substance to be assayed with the specific binding substance, using a specific binding reaction-related substance as the label (signal substance generator) that binds to the specific binding substance in competition with the substance to be assayed or binds to the substance to be assayed directly and specifically without binding to the specific binding substance and can generate signal substances directly or indirectly and (2) signals observed at the detection means can be modulated in response to the distance between the label and the detection means (that is, diffusion length of a signal substance), making use of a signal substance which is released from the label (signal substance generator) and directly or indirectly generates signals that are detectable only at the detection means.

BACKGROUND OF THE INVENTION

There are a number of known specific binding assay methods such as an immunoassay in which an antigen-antibody reaction is employed, a receptor assay in which a receptor is used and a nucleic acid probe assay in which hybridization of complementary nucleic acid sequences is employed. Because of the high specificity, these assay methods are used frequently in various fields including clinical inspection and the like.

In general, these methods are divided into a heterogeneous method which requires a step for the isolation of unreacted substances after specific binding reactions and a homogeneous method that does not require such an isolation step.

The heterogeneous method is useful for the measurement of samples with relatively high sensitivity and can be regarded as a general purpose method, because it can detect the degree of the specific binding reaction without the interference of unreacted substances. This method, however, requires complex handling for the removal of unreacted substances and, in some cases, requires special tools or instruments such as a washing apparatus. Because of this, it is still necessary to improve this method in terms of its simplicity and rapidity.

With the aim of improving the handling simplicity of the homogeneous type assay method, various techniques have been developed, which include agglutination method, EMIT method, proximal linkage immunoassay such as an enzyme channeling technique, immunochromatographic assay and the like. These techniques, however, are still inferior to the heterogeneous method in terms of efficiency and general purpose use.

For example, the agglutination type methods which are effected by the formation of aggregates by antigen-antibody reaction or by the inhibition of the aggregate formation, such as a gel diffusion technique, an erythrocyte agglutination technique, a latex agglutination technique and the like, have considerably inferior sensitivity and accuracy in comparison with other methods in which labels such as enzymes are used.

Examples of homogeneous type methods which are effected by the use of labels such as enzymes include: EMIT method and the like which are effected by the modulation of enzyme activity, itself based on a specific binding reaction; and proximal linkage immunoassay in which signal modulation occurs when two types of labels having a mutual relation get close due to a specific binding reaction. In the case of the EMIT method and related techniques, it is necessary to modify an enzyme, a coenzyme component, an enzyme inhibitor or the like with a substance to be assayed (or an analogue of the substance to be assayed) while the activity of the enzyme or the like is kept constant and to induce a significant modulation of the enzyme activity through a binding reaction of the modified product with a specific binding substance. Because of such requirements, this method is inferior to other methods in terms of sensitivity and general purpose use and, in some cases, cannot be used depending on the physical properties (molecular weight, configuration, solubility and the like) and chemical properties (reactivity, position of functional groups and the like) of the substance to be assayed. On the contrary, the proximal linkage immunoassay can sometimes be effected by certain labeling techniques which are generally used in the heterogeneous method and therefore is superior to the EMIT method and the like in terms of general purpose use. In addition, from the viewpoint of specific binding reaction and detection of signals, increase in the sensitivity and decrease in the measuring time can be expected as the concentration of specific binding substances including labeling substances increases. Such a concentration increment, however, increases approaching frequency of labels independent of the specific binding reaction. Such properties which are contrary to each other become a significant factor that limits the sensitivity. An example of the proximal linkage immunoassay is the enzyme channeling technique in which two types of enzymes are used that catalyze two continued reactions such as formation of a product by a first enzyme and utilization of the product by a second enzyme as its substrate. Processes in relation to such a technique have been disclosed for instance in GB 2018986, EP 32286, EP 75379, *Analytical Biochemistry* (vol. 106, pp. 223–229, 1980) and the like. However, each of these prior art processes is based on the modulation of the total enzyme reaction rate, which is effected by a difference between a time when a labeled enzyme exists in a free state and a time when a microscopic environment is formed by a proximity effect of labels by a specific binding reaction so that channeling of the labeled enzymes can be carried out, or when the labeled enzyme undergoes specific binding to a dispersion type discrete particulate carrier (dextran particles or the like) or to a non-dispersion type carrier (filter paper or the like) which provides a channeling environment. In consequence, a free labeled enzyme in the liquid phase could approach the solid phase by free diffusion, and its non-specific reaction would cause a problem when the concentration of the labeled enzyme is high. Another problem of this technique is that, since a first enzyme can continue its reaction independent of the degree of proximity of a second enzyme, the reaction product of the first enzyme accumulates inside the measuring system when an environment for its channeling with the second enzyme is not formed. Such an accumulation of the product formed by the reaction of the first enzyme also causes acceleration of non-specific reactions. In order to solve such problems, a scavenger is used which can remove excess amounts of the first reaction product. However, addition of a scavenger in an effective amount causes a certain competitive inhibition effect on the whole reaction. Application of such a scavenger, therefore, cannot be regarded as a general purpose countermeasure.

A different type of assay method has been reported which includes a step in which a test sample presumably containing a substance to be assayed is permeated and developed, together with or separately from a labeled specific binding substance, in a chromatographic area that comprises a porous or particulate-packed type carrier to which a specific binding substance is immobilized. Such a method, or an immunochromatographic assay, is advantageous in some cases from the viewpoint of sensitivity and measuring time because of the large immobilizable effective surface area and the relatively high collision efficiency between reaction molecules which can induce a specific binding reaction, in comparison with a liquid phase reaction. In this instance, the label itself may be a signal substance or may generate a signal, moreover, instead of the generation of a signal by the label itself, a signal substance which is concerned in the generation of a signal may be generated by another label. Examples of the former type of labels include a radioactive isotope, a coloring substance, a fluorescent substance, a luminescent substance and the like, and those of the latter type of labels include an enzyme and the like. Processes for the immunochromatographic assay in which the former type labels are used have been disclosed for instance in DE 2729872, WO 8808534, EP 323605, and those in which the latter type labels are used have been disclosed for instance in EP 100619, WO 8505451 and U.S. Pat. No. 4,956,275. The latter type of labels may be advantageous in general when it is desirable to maintain sensitivity without using a radioactive isotope. In the case of the use of the latter type labels, a signal substance is generated by the contact of a component which is necessary for the signal substance generation (for example, an enzyme substrate, a coloring matter or the like) with a label (an enzyme or the like Because of this, such a process requires an additional step to effect the just described contact reaction (to be referred to as "development step" hereinafter), which is carried out after the permeation development step of a test sample presumably containing a substance to be assayed and a labeled specific binding substance, thus entailing the problem of complex handling.

In addition, these immunochromatographic assay processes have a common problem which still remains unsolved. That is, when a labeled specific binding substance and a liquid test sample are subjected to a chromatographic specific binding reaction in a specific binding reaction area, the specific binding reaction at least depends on the reaction frequency of two molecules. Because of this, the binding distribution of the labeled specific binding substance in the chromatographic direction in the specific binding reaction area becomes, more or less, a gentle curved pattern such as a gradient pattern or a sigmoid pattern. When the concentration of a substance to be assayed in a liquid test sample is changed, the reaction frequency changes and the binding distribution of a label in the specific binding reaction area changes, but still exhibits a curved distribution pattern as a whole. Because of this, a boundary line between colored and un-colored portions becomes unclear in many cases, thus causing considerable errors when, for example, the concentration of a substance to be assayed in a liquid test sample is determined qualitatively or quantitatively based on the length or position of a colored portion after the development step, that is, the distance or position to the end point of the binding distribution of a label. In order to improve measuring accuracy, it is necessary to perform quantification of the binding distribution of the label in the specific binding reaction area by understanding it collectively. U.S. Pat. No. 4,956,275 discloses arrangement of a plurality of detection means in a detection area which is also used as a specific binding reaction area. By such an arrangement of a plurality of detection means in the detection area, understanding the accuracy of the binding distribution of a label in the specific binding reaction area is improved in comparison with the case of the use of a single detection means. However, such an improvement is not substantial, because the assay apparatus becomes complex and the number of detection means to be arranged is limited. The just cited patent also discloses that an enzyme channeling-based signal generation system can be arranged in the detection area. According to the description, however, the detection area means an area where immobilized antibody molecules are located, and the description merely explains that only an existing portion of a labeled second enzyme can generate a signal by immobilizing a first enzyme together with the antibody to the detection area and by adding a substrate of the first enzyme to a development solution. In consequence, the process of the just cited patent can simplify the development step, but cannot solve the aforementioned problems in terms of the measuring accuracy and sensitivity.

A specific binding assay device which comprises multilayer analytical materials is known as another type of the immunochromatographic assay. Techniques in relation to this type of process have been disclosed for instance in EP 51183, EP 66648, DE 3227474 and EP 236768. Of these, each of EP 51181 and EP 66648 discloses a process in which a specific binding layer comprising a porous material immobilizing a specific binding substance is superposed on a detection layer and, after completion of the specific binding reaction, a labeled substance permeated into the detection layer is detected with a reagent contained in the detection layer. These patents also disclose that a light-shading layer is interposed between the detection layer and the specific binding layer, in order to avoid a bad influence of signals originating from a labeled substance bound to the specific binding layer. However, when a signal product is formed by the reaction of a labeled substance with a reagent in the detection layer, such as the case in which the label is an enzyme, the light-shading layer cannot prevent bad influences of inverse diffusion of the reagent into the specific binding layer and permeation of an enzyme reaction product formed in the specific binding layer into the detection layer. Each of DE 3227474 and EP 236768 discloses a specific binding assay device which comprises multilayer analytical materials into which the principle of the homogeneous method is introduced or in which an immobilized enzyme substrate is introduced into a specific binding layer. However, both of these devices cannot avoid the limitations of the homogeneous method described in the foregoing, and the bad effects caused by the curved binding distribution pattern of a label in the specific binding layer are very serious because of the short and thin chromatography layer.

As described above, a number of specific binding assay methods have been developed with the aim of improving simplicity and quickness, but virtually nothing has been reported about a highly sensitive specific binding assay method which can also be used for various purposes and which can determine a substance to be assayed semi-quantitatively or quantitatively with high accuracy.

With the recently expanding domestic and regional medical care and increasing demands for emergency clinical inspections, great concern has been directed toward the development of a specific binding assay method by which a substance to be assayed can be measured quickly, easily and accurately even by persons who have no knowledge about clinical inspection. Under such circumstances, various types of sensors have been developed including electrochemical sensors. In the field of biochemical assay methods, simple and quick measuring methods have been developed making use of enzyme sensors and the like, and have already been disclosed for example in JP-B 02-59424 (the term "JP-B" as used herein means an "examined Japanese patent publication") and EP 125136. Though positive attempts have been made to apply such measuring methods to the specific binding assay process, virtually nothing has been reported on the development of a general purpose assay process which can be handled easily. Of these prior art sensors for use in the specific binding assay, electrochemical sensors which are effected by the use of relatively high sensitivity labels such as enzymes are described in the following.

EP 125136 discloses a specific binding reaction on the surface of an electrode to which an enzyme (catalase)-labeled antibody preparation is applied. Also, EP 125136 discloses a competitive specific binding reaction on the surface of an electrode to which an enzyme (glucose oxidase)-labeled substance is applied. Since a specific binding substance is immobilized on the surface of an electrode which has a limitation in its size, each of the sensors in these disclosures is limited in the immobilization efficiency. Because of this, and because the reaction is effected in a liquid phase, each of these sensors possesses disadvantages in terms of sensitivity and measuring time.

EP 125136 discloses an enzyme activity detection sensor which comprises an oxidation-reduction enzyme (glucose oxidase or the like) and an electron mediator (a ferrocene derivative or the like), in which the extent of a specific binding reaction is measured using either of the enzyme and the electron mediator as a label, by changing (a) the effective level of the electron mediator, (b) the effective level of the enzyme, (c) the effective levels of the electron mediator and the enzyme simultaneously and (d) the effective area of the electrode. According to this disclosure, the specific binding reaction is effected on the surface of a solid phase (vessel wall or electrode) (heterogeneous method) or in a solution where the electrode exists (homogeneous method). Similar to the case of other heterogeneous type methods, the heterogeneous method of this disclosure requires a step for the isolation or washing of unreacted substances. In addition to this, only the surface of the vessel wall or the electrode is available as the immobilization carrier. This sensor, therefore, fails to improve the measuring efficiency and simplicity of the heterogeneous method. Also, the homogeneous method of this disclosure is substantially identical to any of the aforementioned homogeneous type methods, thus leaving the homogeneous method-inherent problems unsolved. For example, in the homogeneous method in which a ligand-modified electron mediator is used, the electron mediator should have a capacity to perform electron transfer by getting close to the redox center of the enzyme molecule. However, when an electron mediator is modified with a ligand, the function of the electron mediator is spoiled in some cases depending on the type of the ligand to be used, thus entailing limited availability of ligands, as well as a disadvantage in terms of the sensitivity. A similar technique has been disclosed in EP 402126 which also has a limitation with regard to the binding of an electron mediator and a ligand to carrier molecules.

Similar techniques have also been disclosed for instance in EP 142301, EP 125139, EP 150999, JP-A 63-139248 (the term "JP-A" as used herein means an "unexamined published Japanese patent application"), U.S. Pat. No. 4,963,245, U.S. Pat. No. 5,066,372, Anal. Chem. (vol. 56, pp. 2355–2360, 1984) and Clin. Chem. (vol. 31, pp. 1449–1452, 1985). Of these, each of U.S. Pat. No. 4,963,245 and U.S. Pat. No. 5,066,372 discloses a semi-homogeneous method in which the measurement after a specific binding reaction is effected without requiring a step for the washing of unreacted substances, by magnetically separating specific binding substance-immobilized magnetic particles on the surface of an electrode. However, this type of method requires a magnetic separation device in order to separate the magnetic particle carrier physically. In addition, similar to the case of the aforementioned proximal linkage immunoassay (enzyme channeling technique or the like), a labeled enzyme free in the liquid phase can approach the electrode by free diffusion, and the resulting non-specific reaction becomes a cause of problems.

EP 223541 discloses a heterogeneous electrochemical specific binding assay process in which an enzyme (alkaline phosphatase) is used as a label that catalyzes conversion of an inactive type electron mediator precursor (a ferrocene-linked substrate) into an active type electron mediator. A PCT application (WO 89-05454) discloses a heterogeneous type specific binding assay process in which an enzyme (alkaline phosphatase) that catalyzes conversion of a precursor ($NADP^+$) into its oxidation-reduction pair ($NAD^+$) is used as a label, and the amount of the formed oxidation-reduction pair is measured using an electrochemical enzyme sensor. Also, JP-A 02-112752 discloses a process in which biological cells trapped on a depth filter are allowed to react with enzyme-labeled antibody on the filter, unreacted molecules of the labeled antibody are removed by washing, and then the biological cells are detected by measuring activities of the labeled enzyme using an electrode. However, being a typical heterogeneous method, each of these processes fails to improve the measuring performance and simplicity of the conventional heterogeneous method.

SUMMARY OF THE INVENTION

A primary object of the present invention is to provide the simple general purpose process useful for quick qualitative or quantitative analysis, which is based on a principle of the specific binding assay but does not require a step for the separation (washing) of unreacted substances, as well as a specific binding assay device suitable for the practice of the process.

Particularly, the present invention provides a process for general purpose specific binding assay use, as well as a device suitable for the practice of the process, which (1) can be applied suitably to various sensor techniques that render possible measurement using a relatively small and simple measuring device, (2) can be applied suitably to various immunochromatographic assay carriers that are handy and from which sensitivity improvement can be expected, (3) can minimize the immunochromatographic assay-inherent impeding effects originating from the curving tendency of the binding distribution of labels, (4) can suitably use signal substance generators (enzymes and the like) that render possible relatively high sensitivity measurement, and (5) has no limitations specific to the homogeneous type method, but rather can suitably employ labeling techniques and immobilization techniques that are used in conventional general immunoassay processes.

According to a first aspect of the present invention, there is provided a process for specific binding assay in which a substance to be assayed in a test sample is determined qualitatively or quantitatively by at least one specific binding reaction of the substance to be assayed with a specific binding substance that binds specifically to the substance to be assayed, which comprises introducing a liquid test sample presumably containing the substance to be assayed for a detection means through a matrix, wherein a signal substance generator is allowed to distribute in the matrix by a specific binding reaction of the substance to be assayed with the specific binding substance, and the resulting change corresponding to the amount of the substance to be assayed in the distribution of the signal substance generator in the matrix is measured as a degree of signal modulation at the detection means via a signal substance which directly or indirectly generates a signal which is detectable only at the detection means.

According to a second aspect of the present invention, there is provided a specific binding assay device useful for the practice of the assay process of the first aspect of the present invention, which comprises a sample-introducing means (a), a matrix (b), a detection means (c) and, when required, an absorption means (d).

Other objects and advantages of the present invention will be made apparent as the description progresses.

It is noted that each term of a substance, a precursor, a substrate, a generator, and an electron mediator used herein in singular form does not mean a singular number but represents the generic name of one or more species in singular number or plural number.

BRIEF DESCRIPTION OF THE DRAWINGS

FIGS. 10A–10H are a perspective diagram showing an example of the matrix shape of the device of the present invention.

FIG. 11 is a schematic illustration showing the experiment performed in Example 2.

FIG. 12 is a graph showing results of the experiment performed in Example 2.

FIG. 13 is a schematic illustration showing an assay device used in Example 3.

Figure 1A:
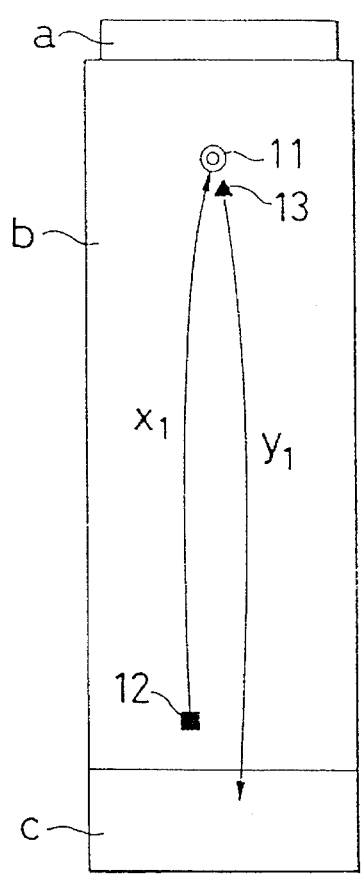
FIGS. 1A and 1B are a conceptual representation showing a principle of the process of the present invention.

In these figures, means, substances, conditions and the like are indicated by characters as follows: a, sample-introducing means; b, matrix; c, detection means; d, absorption means; e, support (or base); f, cover; g, hole; s, signal; 1, specific binding assay device; 11, signal substance generator; 12, substance related to the generation of signal substance; 13, signal substance; 14, substance to be assayed; 15, substance related to signal generation; 20, permeation direction of liquid test sample; 21, sample-introducing hole; 22, upper plate; 23, communication means; 24, counter/reference electrode; 25, working electrode; 26, reference electrode terminal; 27, working electrode terminal; 28, sealing means; 29, through hole and 30, sample introducing filter.

DETAILED DESCRIPTION OF THE INVENTION

Firstly, technical terms used in the specification of this invention are explained.

The term "substance to be assayed" as used herein means a substance which is detected qualitatively or quantitatively by the process or the device of the present invention. Examples of such substances include those which are functionally capable of acting as antibody molecules and antigens, such as proteins, polypeptides, glycoproteins, polysaccharides, complex glycolipids, nucleic acids, effector molecules, receptor molecules, enzymes, inhibitors and the like. More illustratively, such substances include: tumor markers such as α-fetoprotein, carcinoembryonic antigen (CEA), CA 125, CA 19-9 and the like; various proteins, glycoproteins and complex glycolipids such as $\beta_2$-microglobulin ($\beta_2$ m), ferritin and the like; various hormones such as estradiol ($E_2$), estriol ($E_3$), human chorionic gonadotropin (hCG), luteinizing hormone (LH), human placental lactogen (hPL) and the like; various virus-related antigens and virus-related antibody molecules such as HBs antigen, anti-HBs antibody, HBc antigen, anti-HBc antibody, anti-HCV antibody, anti-HIV antibody and the like; various allergens and their corresponding IgE antibody molecules; narcotic drugs and medical drugs and metabolic products thereof; and nucleic acids having virus- and tumor-related polynucleotide sequences.

The term "analogue of a substance to be assayed" as used herein means a substance which shows similar behavior to the substance to be assayed in a binding reaction with a specific binding substance. In general, it means a substance which is structurally analogous to the substances to be assayed. Illustrative examples include various types of structural analogues of the substances to be assayed. In the present invention, these structural analogues are used as composing elements of signal substance generators which will be described later, mainly when a substance to be assayed has a low molecular weight and its specific binding reaction is effected by a competitive method.

The term "test sample" as used herein means a liquid material which contains or probably contains a substance to be assayed. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like.

The term "specific binding substance" as used herein means a substance which has a specific affinity for a certain substance such as a substance to be assayed, that is, a substance which is capable of undergoing a specific binding reaction with a specific substance. Examples of combinations of the specific substance with the specific binding substance include: antigens with corresponding antibody molecules, a nucleic acid sequence with its complementary sequence, effector molecules with receptor molecules, enzymes with inhibitors, sugar chain-containing compounds with lectins, an antibody molecule with another antibody molecule specific for the former antibody, receptor molecules with corresponding antibody molecules and the like combinations. Other examples of the specific binding substances include a compound which has been chemically modified to such a degree that its specific binding activity still remains intact and a complex body of a compound bound to other components. Examples of combinations of such types of specific binding substances with the specific substances include: a chemically biotin-modified antibody molecule or polynucleotide with avidin, an avidin-bound antibody molecule with biotin and the like combinations.

In the specification of the present invention, a substance which has a portion that acts as a specific binding substance may also be used as a specific binding substance, such as the following signal substance generator.

The term "signal substance generator" as used herein means a substance which (1) takes part in the specific binding reaction such as binding to a specific binding substance in competition with a substance to be assayed or specific binding to the substance to be assayed, (2) generates a signal directly or indirectly and (3) shows distributional changes in a matrix, keeping a correlation to the amount of the substance to be assayed.

In other words, the signal substance generator is a labeled specific binding substance consisting of a portion which acts as a specific binding substance and another portion that contributes to the formation of a signal substance which will be described later.

In this instance, the portion which acts as a specific binding substance has a structure as a specific binding substance for a substance to be assayed, or has a structure of the substance to be assayed or its analogue, and the other portion that contributes to the formation of a signal substance is composed of various types of enzymes or the like which are conventionally used as labeling agents in immune reactions and the like.

That is, the signal substance generator is a substance which, on the one hand, takes part in the specific binding reaction of a substance to be assayed with a corresponding specific binding substance, thereby changing its distribution in a matrix in response the the amount of the substance to be assayed, and, on the other hand, contributes to the formation of a signal substance.

The term "signal substance" as used herein means a substance which is formed by the signal substance generator-contributing reaction and which generates a certain signal by itself or causes other substance to generate a signal.

The term "substance related to the generation of a signal substance" as used herein may include the signal substance generator when the term is interpreted literally. According to the present invention, however, it means a substance other than the signal substance generator, such as a precursor of a signal substance or a substance which contributes to the conversion of the precursor into its corresponding signal substance.

The term "electron mediator" as used herein represents, in accordance with the present invention, the generic name of oxidation-reduction compounds which mediate between an enzyme reaction and an electrode reaction, thereby rendering possible electron transfer between the two reactions. Such compounds include a substance which does not form substantially irreversible by-products in either of the two reactions and is capable of undergoing cycling between the two reactions.

The term "substance related to the generation of a signal" means a substance which contributes to the generation of a signal, excluding the signal substance, when the signal substance does not generate a signal directly but causes other substance to generate a signal, or when the signal substance generates a signal in conjunction with another substance.

Examples of signals include electron transfer which is measurable electrochemically, fluorescence which is measurable using a fluorophotometer, luminescence which is measurable using a luminometer, and coloring which is measurable by visual judgment or by using a color-difference meter.

The specific binding substance, the signal substance generator, the substance related to the generation of a signal substance and the substance related to the generation of a signal may be included in the reaction system in advance or may be introduced into the reaction system prior to, at the same time as, or after the introduction of a test sample.

When these substances are included in the reaction system in advance, they may be distributed evenly in the reaction system or arranged on specified positions in the reaction system so that they are able to diffuse when a liquid test sample or a developing solution other than the sample is introduced.

According to the assay device of the present invention, the term "sample-introducing means" as used herein means a portion where a test sample is introduced.

The term "matrix" as used herein means an area where a substance to be assayed and a signal substance generator are developed, for example, an area where a specific binding substance is immobilized and a specific binding reaction occurs having a distribution along the flow direction of a test sample. In an illustrative example of such an area, a substance to be assayed and a signal substance generator perform specific binding to a specific binding substance in a competitive manner, or the substance to be assayed binds to the specific binding substance and then the signal substance generator binds to the substance to be assayed in a sandwich binding type reaction, in which the specific binding reaction occurs having a distribution along the flow direction of a test sample.

The matrix where the specific binding reaction and the like occur having a distribution along the flow direction of a test sample is not limited to the case in which a specific binding substance is immobilized, but may be an area where changes in the molecular weight and the like caused by the specific binding reaction are detected and exhibited as a distribution.

The term "detection means" as used herein means an area where a signal is detected and the degree of signal modulation is measured by visual judgment or by using an appropriate external measuring instrument depending on the signal properties.

The term "absorption means" as used herein means a part which comprises a water-absorbable material and where, when required, the aforementioned substance related to the generation of a signal substance and the like substances are maintained. This means also contributes to the absorption and keeping of the introduced liquid test sample.

The following describes the present invention in detail making use of the thus defined terms.

The specific binding assay process of the present invention is characterized in that a specific binding reaction is effected in a matrix and in that a signal formed via a signal substance generated by a signal substance generator whose distribution in the matrix is changed by the specific binding reaction can be detected only by a detection means without requiring a B/F separation step. In this instance, the term "specific binding reaction" means a reaction of a substance to be assayed with a specific binding substance (contains a signal substance generator) which has a specific affinity for the substance to be assayed, a reaction of a specific binding substance that binds specifically to the substance to be assayed with a signal substance generator, or the like reaction. More particularly, the specific binding assay process and the device suitable for the practice of the process of the present invention have been accomplished on the basis of the findings that: (1) signals observed at a detection means can be modulated in response to the distance between a label and the detection means (that is, diffusion length of a signal substance), in the case of the use of a signal substance which is generated by the label of a signal substance generator and which directly or indirectly generates signals that are detectable only at the detection means; and (2) distribution of the signal substance generator (label) correlative to the detection means can be changed in response to the concentration of a substance to be assayed, through at least one specific binding reaction of the substance to be assayed with a substance (specific binding substance) which binds specifically to the substance no be assayed.

According to the specific binding assay process of the present invention, the length distribution of the signal substance generator to the detection means is changed in response to the amount of a substance to be assayed in a test sample through the specific binding reaction, and the resulting changes in the distribution are measured.

The following describes a method for the distribution changing, though it is merely an example among various possible techniques.

In this instance, preferably, the following factors (A) to (C) may be satisfied to effect measurement of the distribution.

(A) Distribution related to the amount of the substance to be assayed of the length of signal substance generators to the detection means should change in such a size that mass transfer of a signal material becomes the rate-determining step in generating a signal. As will be confirmed later in Examples 3 and 4, in the cases of an enzyme-substrate and an enzyme-substrate-electron mediator reaction system, such sizes are in the order of L (see FIG. 3)=about 0 to 500 µm or L=about 0 to 1,000 µm respectively, as the linear distance between the detection means and the signal substance generator. But it is noted that the sizes may be changed with materials composed of a matrix, properties of a signal substance or a signal substance generator, materials of a detection means and properties of a detection method.

(B) In order that changes in the length distribution can be measured in response to the amount of a substance to be assayed in a test sample, free enzyme molecules in portions of the signal substance generator should be minimized as small as possible. Then, the signal substance generator is added to a concentration which is equivalent to the sensitivity of the detection means. As will be confirmed later in Examples 1(1), 5(1) and 8(1), when a signal substance generator (enzyme labelled antibodies) is prepared, free enzyme molecules are removed.

(C) An element which is essential for the detection of a signal which is generated directly or indirectly from a signal substance or at least a portion of the member should substantially be immobilized to the detection means. As will be confirmed later in Examples 1, 5, 6 and 8, the suitable electrodes or enzyme electrodes used in the Examples are composed of the materials immobilized to the electron means.

Figure 1B:
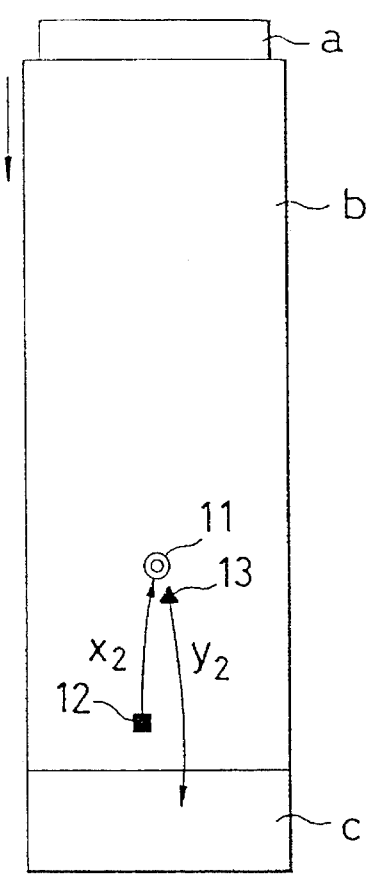

The following describes a principle of the assay process of the present invention based on the drawing shown in FIGS. 1A and 1B. In this instance, the device shown in FIGS. 1A and 1B is constructed in such a way that a test sample introduced into a sample-introducing means (a) is led into a matrix (b) and then to a detection means (c) where the liquid flow is substantially stopped.

FIGS. 1A and 1B show the position of a signal substance generator 11 at the time when it is led into the matrix (b) and its specific binding reaction is completed. In this figure, 12 is a substance related to the generation of a signal substance, and the arrows indicate travel directions of the test sample and the like.

FIG. 1-(A) shows a state in which the signal substance generator 11 is trapped in the upper part of the matrix (b) or stopped at the upper part of the matrix (b) because of its small travel speed, and FIG. 1-(B) shows a state in which the signal substance generator 11 has reached the lower part of the matrix (b).

When the signal substance generator 11 is in the state of FIG. 1-(A), at least a portion of the substance 12 related to the generation of a signal substance reaches the signal substance generator 11 by diffusion through the distance $x_1$, and the substance 12 related to the generation of a signal substance becomes a signal substance 13 by the function of the signal substance generator 11. Thereafter, at least a portion of the signal substance 13 reaches the detection means (c) by diffusion through the distance $y_1$ and generates a signal at the detection means (c).

On the other hand, when the signal substance generator 11 is in the state of FIG. 1-(B), the diffusion distance $x_2$ which is necessary for at least a portion of the substance 12 related to the generation of a signal substance to reach the signal substance generator 11 is shorter than the case of the distance $x_1$, and the diffusion distance $y_2$ which is necessary for at least a portion of the generated signal substance 13 to reach the detection means (c) is also shorter than the case of the distance $y_1$. In consequence, in comparison with the former case in which the signal substance generator 11 is in the state of FIG. 1-(A), the probability of of the signal substance 13 reached the detection means (c) is high, and the signal generation frequency (signal strength) and/or the signal generation speed are also high.

In the assay process of the present invention, the amount or the presence of a substance to be assayed is measured making use of the difference in the signal generation frequency (signal strength) and/or the signal generation speed between a signal related to the signal substance generator 11 which is in the state shown in FIG. 1-(A) and another signal related to the signal substance generator 11 that is in the state of FIG. 1-(B).

Figure 8:
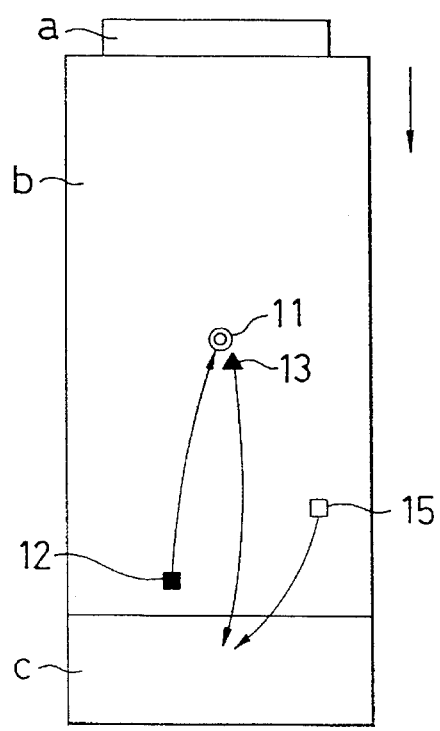
FIG. 8 is a conceptual representation showing a principle of the process of the present invention.
Figure 9A:
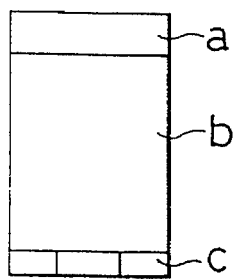
FIGS. 9A–9H are a side view or a plan view showing an example of the device of the present invention.
Figure 9B:
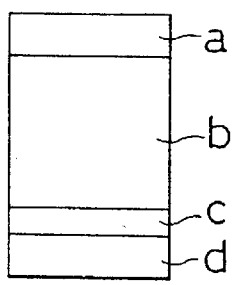
Figure 9C:
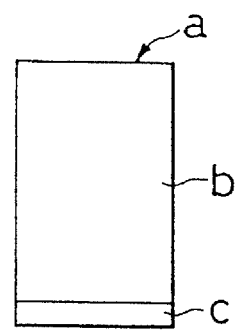
Figure 9D:
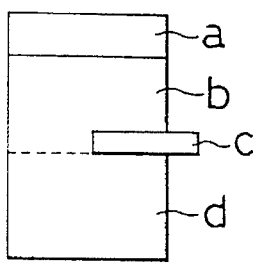
Figure 9E:
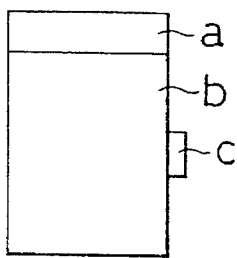
Figure 9F:
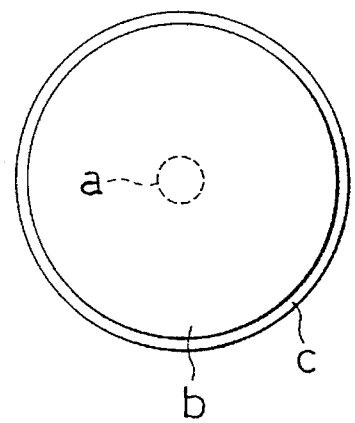
Figure 9G:
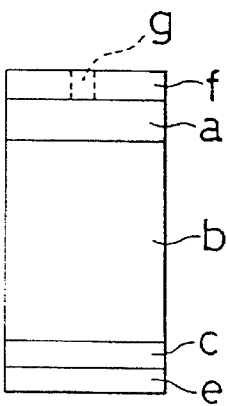
Figure 9H:
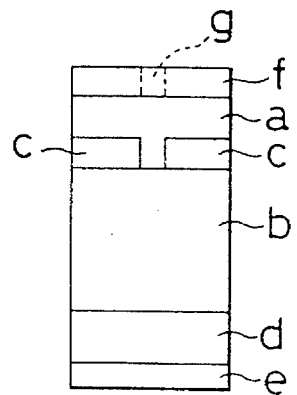
Figure 10A:
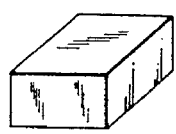
Figure 10B:
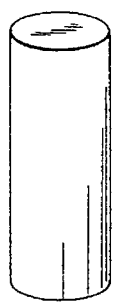
Figure 10C:
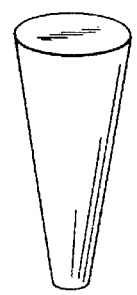
Figure 10D:
Figure 10E:
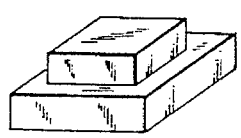
Figure 10F:
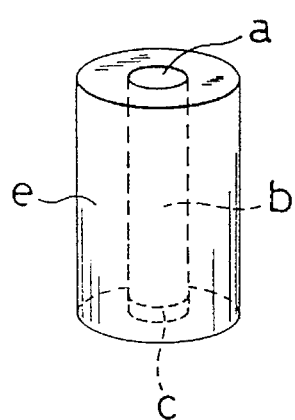
Figure 10G:
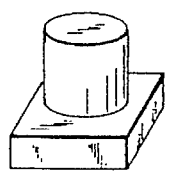
Figure 10F:
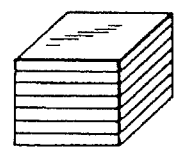

When the signal substance 13 does not generate a signal directly, a substance 15 related to the generation of a signal must reach an area close to the detection means (c) or be present in the area as shown in FIG. 8, though the basic principle is the same as the case of FIGS. 1A and 1B.

Figure 2:
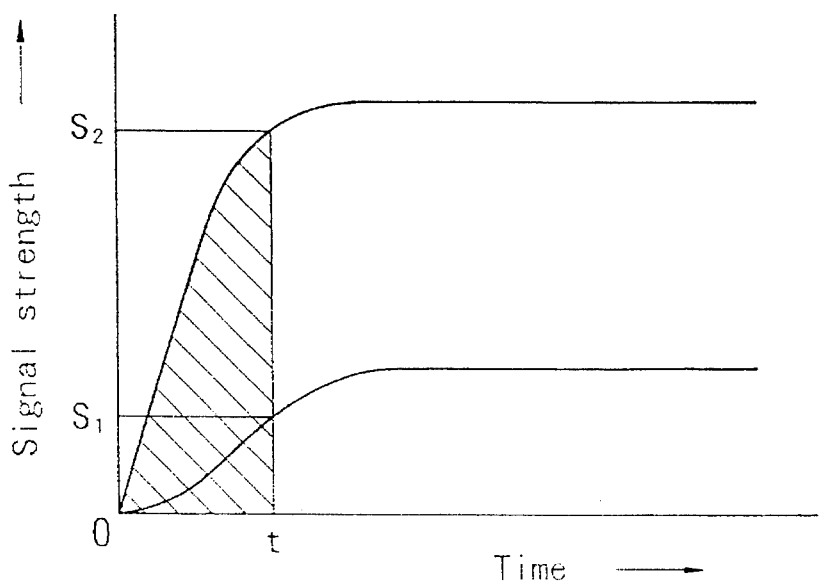
FIG. 2 is the graph showing a relationship between the signal strength and the elapsed time after commencement of a measurement.

FIG. 2 shows an example of the relationship between signal strength measured by the assay process of the present invention and elapsed time after commencement of the introduction of the signal substance generator 11 into the matrix (b). For example, the initial rate of the generation of a signal related to the signal substance generator 11 which is in the state of FIG. 1-(A) is slower than the case of a signal related to the signal substance generator 11 that is in the state of FIG. 1-(B). As will be described later, the distribution of the signal substance generator 11 in the matrix (b) is regulated by the amount of the substance to be assayed in a test sample. Than is, the ratio of the signal substance generator 11 in the state of FIG. 1-(A) to the signal substance generator 11 in the state of FIG. 1-(B) changes depending on the amount of the substance to be assayed in a test sample. Signals detected at the detection means (c) are measured as the sum total of signals related to the signal substance generator 11 in the FIG. 1-(A), FIG. 1-(B) and the like states. As shown in FIG. 2, the initial rate of signals becomes slow when the ratio of the signal substance generator 11 in the state of FIG. 1-(A) is high, and the initial rate of signals becomes rapid when the ratio of the signal substance generator 11 in the state of FIG. 1-(B) is high. In consequence, the amount of a substance to be assayed can be calculated by measuring the initial rate of signals and converting the measured rate into changes in the distribution of the signal substance generator in a test sample.

As shown in FIG. 2, signals may be measured based on the signal strength at an optional time t ($s_1$ or $s_2$) or as a time t until the signal strength reaches a specified level or, as indicated by the oblique lines in FIG. 2, as an integrated value of the signal strength until the time t. Signal measurement may also be effected by measuring signal strengths at two specified times and calculating the difference between the two signal strengths. Any other method may be applied to the measurement of signals, provided that it can measure modulation of signals caused by changes in the distribution of the signal substance generator 11 in the matrix (b).

The following describes mathematical modeling of the above description and estimation of signal modulation.

Figure 3:
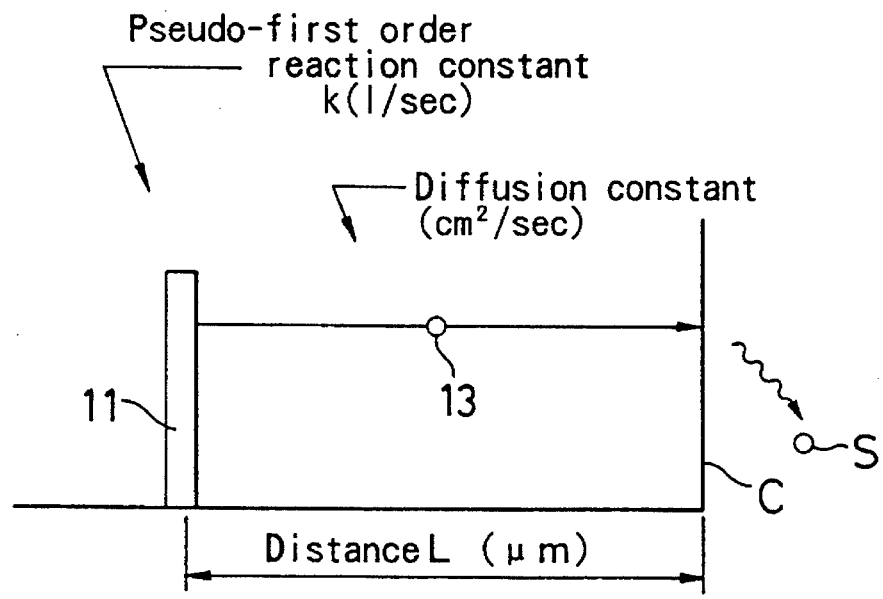
FIG. 3 is a conceptual graph showing a principle of the process of the present invention.
Figure 4:
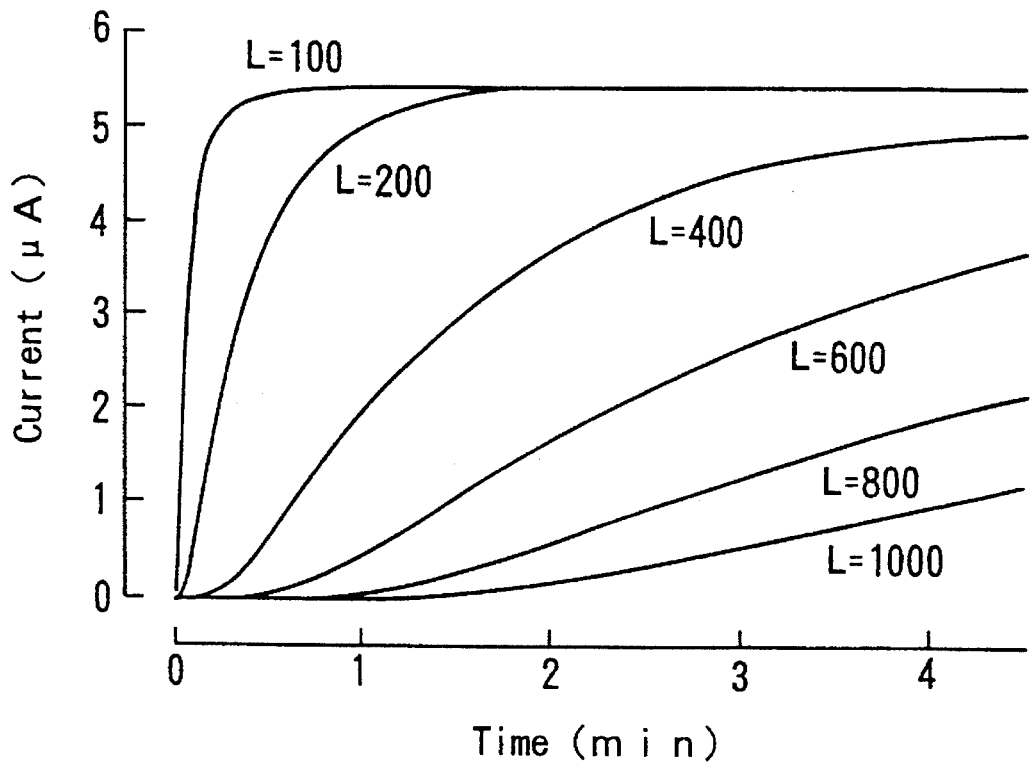
FIG. 4 is a graph showing theoretically predicted changes in current signals which are detected at a detection means (c) in response to the distance L, based on the assumption shown in FIG. 3.

FIG. 3 is a conceptual graph for use in the explanation of the principle of the assay process of the present invention in which the signal substance generator 11 is located at a position which is distant from the detection means (c) by a distance L. In the figure, a signal substance generator 11 such as an enzyme labeled substance is located at a position which is distant from a detection means (c) such as an electrode by a distance L (μm), and a signal substance 13 is generated continuously at a pseudo-first order reaction constant k (1/sec). The signal substance 13 thus generated has a diffusion constant D ($cm^2$/sec), and all of the signal substance 13 which reaches the surface of the detection means by diffusion generates a signal s such as a current value. This is a considerably simplified model, because generation of the signal substance 13 is assumed to be a pseudo-first order reaction, all of the signal substance 13 which reaches the surface of the detection means generates a signal s, the presence of other elements such as a substance related to the generation of a signal substance and a substance related to the generation of a signal is disregarded, and the condition of the signal substance after signal generation is not taken into consideration. Though the present invention is not limited to this hypothetical model, it seems that this model accurately reflects the basic condition of the present invention, that is, "changes in the distribution of the signal substance generator 11 in the matrix are measured as a degree of the modulation of the signal s at the detection means (c) via the signal substance 13 which is generated by the signal substance generator 11 and which generates a signal that is detectable only at the detection means (c)". As shown in FIG. 4, when the signal substance 13 causes an oxidation-reduction reaction on the surface of a detection means (electrode) where sufficient overvoltage is applied and an electric current I is measured as the signal s, theoretical prediction lines of current signals detected at the detection means (c) can be prepared in response to the distance L based on the assumption shown in FIG. 3, and modulation of the current signals shown in FIG. 4 can be predicted based on the distance L. The inventors of the present invention have predicted a possibility of such a signal modulation, confirmed the possibility through experiments such as those shown in Examples 3 and 4, and found that application of such a signal modulation to a specific binding assay process was markedly useful. In this way, the inventive specific binding assay device has been devised.

In the aforementioned example, a considerably biased distribution was assumed in which the signal substance generator 11 was located at a specific position and signal modulation was effected by changing the distance between the located position and an electrode. However, since mass diffusion such as diffusion of the signal substance 13 and the like can be overlapped in general, the continuous curved distribution of the signal substance generator 11 in the immunochromatographic assay can be treated by dividing the distribution into microcubic contents. Since a signal s originating from the signal substance generator 11 in each microcubic content shows the aforementioned behavior, the signal s in the case of the continuous curved distribution of the signal substance generator 11 becomes the sum total of each signal s originating from the signal substance generator 11 in each of the microcubic contents which constitute the distribution. In consequence, the sum total of the signal s can be modulated by changing the continuous curved distribution of the signal substance generator 11 through a specific binding reaction. On the contrary, an excellent specific binding assay device can be produced by arranging the detection means (c) at a specified position where changes in such a distribution of the signal substance generator 11 can be detected as a signal modulation with high sensitivity. Illustrative examples of such devices will be described later in Examples 1, 5, 6 and 8, though the assay device of the present invention is not limited to these examples because many other modifications are possible in terms of the type of matrix (b) and the positional relation between the matrix (b) and the detection means (c). Though signals are detected by electrochemical means in the above description and in the Examples, any other signal s can be applied to the assay process and device of the present invention, provided that the signal substance 13 can generate the signal s directly or indirectly at the detection means (c).

Next, the following describes changes in the distribution of a signal substance generator in a matrix in response to the amount of a substance to be assayed in a test sample, in the practice of the assay process of the present invention in which an antigen-antibody reaction is employed, making use of the drawings attached hereto.

Figure 5A:
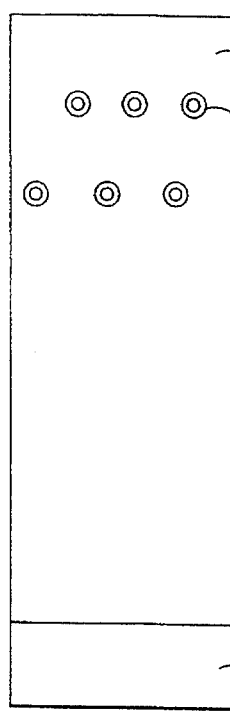
FIGS. 5A–5C are a conceptual representation showing a principle of the process of the present invention.
Figure 5B:
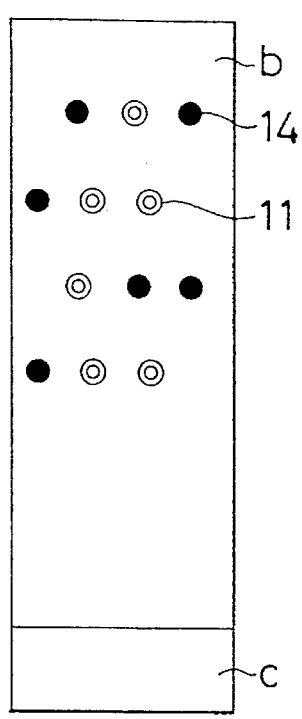
Figure 5C:
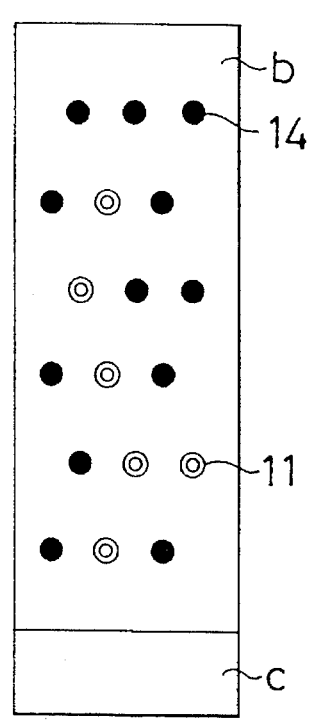

FIGS. 5A–5C is an aspect of the assay process of the present invention, showing the distribution of a substance to be assayed 14 and a signal substance generator 11 in a matrix (b), when the substance to be assayed 14 is measured by a competitive method. In this instance, the substance to be assayed 14 is an antigen, and antibody molecules specific for the antigen, that is, a first specific binding substance, is immobilized in the matrix (b). Also, the signal substance generator 11 is a labeled antigen which competes with the substance to be assayed for the first specific binding substance, and the signal substance generator 11 is introduced into the matrix (b) together with a test sample.

FIG. 5-(A) shows a case in which the substance to be assayed 14 is not contained in a test sample. In this case, the signal substance generator 11 reacts with the antibody immobilized on an upper part (upstream side in terms of the flow direction of a test sample) of the matrix (b) and is trapped in the upper part of the matrix (b). Since the distance between the signal substance generator 11 and the detection means (c) is long in this case, signals measured after (until) a predetermined elapsed time are very small or zero.

FIG. 5-(B) and FIG. 5-(C) show a case in which the substance to be assayed 14 is contained in a test sample. As is evident from the figure, the amount of the substance to be assayed 14 is larger in 5-(C) than in 5-(B).

In this case, the signal substance generator 11 and the substance to be assayed 14 (antigen) react in a competitive manner with the antibody immobilized in the matrix (b). As the amount of the substance to be assayed 14 increases, inhibition frequency of the binding of the signal substance generator 11 to the immobilized antibody increases. As a result, the signal substance generator 11 is trapped in an area ranging from the upper part to the middle part (in the case of FIG. 5-(B)) or from the upper part to the lower part (FIG. 5-(C)) of the matrix (b). When the amount of the substance to be assayed 14 is large, a portion of the signal substance generator 11 is not trapped but reaches the detection means (c).

In the case of FIG. 5-(B), the distance between the signal substance generator 11 and the detection means (c) is a medium-to-long distance type, while that of the case of FIG. 5-(C) is a short-to-long distance type. In consequence, signals measured after (until) a predetermined elapsed time are medium in the case of FIG. 5-(B) and large in FIG. 5-(C).

Figure 7A:
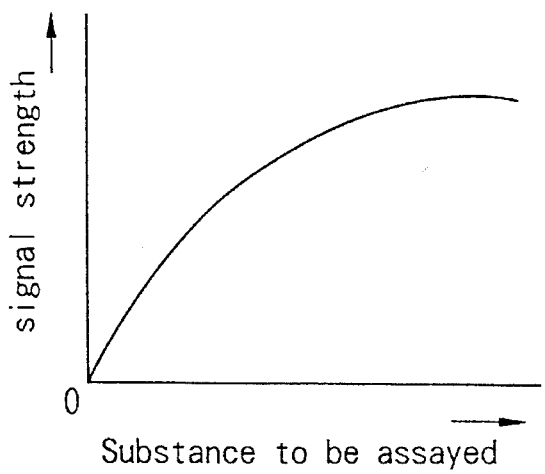
FIGS. 7A and 7B are a graph showing the relationship between the amount of a substance to be assayed in a test sample and the signal strength.
Figure 7B:
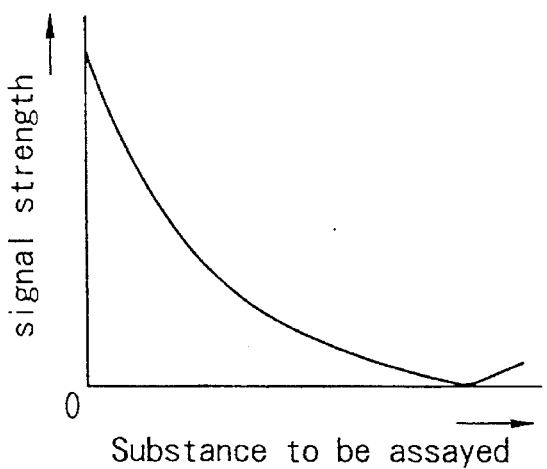

In other words, the signal strength becomes large in proportion to the amount of the substance to be assayed 14 as shown in FIG. 7-(A).

Figure 6A:
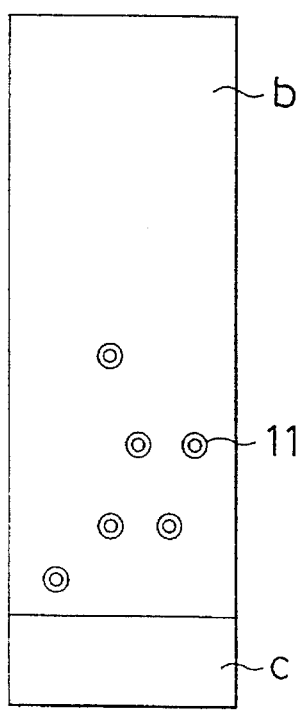
FIGS. 6A–6C are a conceptual representation showing a principle of the process of the present invention.
Figure 6B:
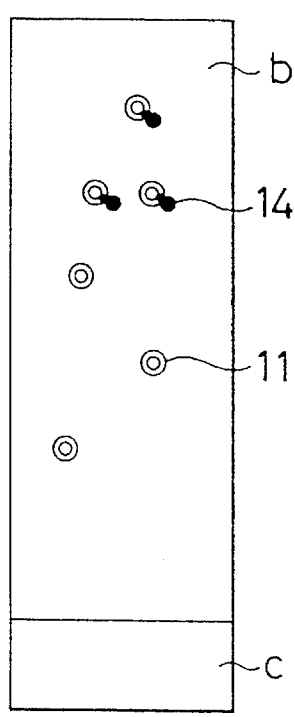
Figure 6C:
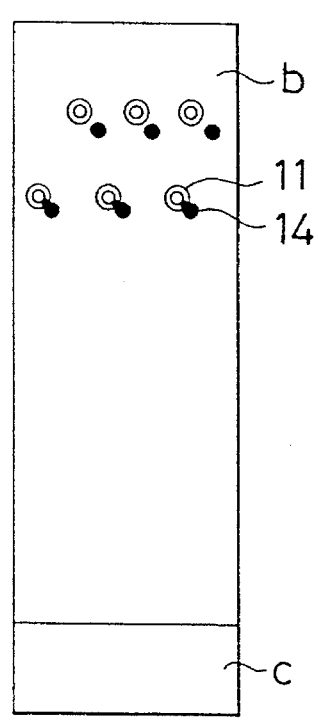

FIGS. 6A–6C are another aspect of the assay process of the present invention, showing the distribution of a substance to be assayed 14 and a signal substance generator 11 in a matrix (b), when the substance to be assayed 14 is measured by a sandwich method. In this instance, the substance to be assayed 14 is an antigen, and antibody molecules specific for epitope A of the antigen, that is, a first specific binding substance, is immobilized in the matrix (b). Also, the signal substance generator 11 is a labeled antibody molecule which is prepared by binding a labeling material to antibody molecules specific for epitope B of the antigen, or a second specific binding substance, and the signal substance generator 11 is introduced into the matrix (b) together with a test sample.

FIG. 6-(A) shows a case in which the substance to be assayed 14 is not contained in a test sample. In this case, since the antigens as the substance to be assayed 14 are not trapped in the matrix (b), the signal substance generator 11 is not trapped in the matrix (b) but reaches the lower part (downstream side in terms of the flow direction of a test sample) of the matrix (b). Since the distance between the signal substance generator 11 and the detection means (c) is short in this case, signals measured after (until) a predetermined elapsed time are large.

FIG. 6-(B) and FIG. 6-(C) show a case in which the substance to be assayed 14 is contained in a test sample. As is evident from the figure, the amount of the substance to be assayed 14 is larger in 6-(C) than in 6-(B).

In this case, a portion of the signal substance generator 11, which is related to the amount of the substance to be assayed 14 (antigen) trapped in the matrix (b) via the antibody, binds to the substance to be assayed 14 and becomes trapped mainly in the upper part of the matrix (b). An excess portion of the signal substance generator 11, however, is not trapped in the matrix (b) but reaches lower part of the matrix (b).

As a result, the signal substance generator 11 is trapped in an area ranging from the upper part to the middle part or from the upper part to the lower part of the matrix (b) in the case of FIG. 6-(B) in which the amount of the substance to be assayed 14 is smaller than the amount of the signal substance generator 11.

Also, the signal substance generator 11 is trapped mainly in the upper part of the matrix (b) in the case of FIG. 6-(C) in which the substance to be assayed 14 exists in an appropriate amount compared to the amount of the antibody immobilized in the matrix (b) and the amount of the signal substance generator 11.

When the amount of the substance to be assayed 14 is large, the substance to be assayed 14 is trapped in the matrix (b) ranging from its upper part to lower part and, as a result, the signal substance generator 11 is also trapped in the matrix (b) ranging from its upper part to lower part. In consequence, the distribution of the signal substance generator 11 becomes close to the case of FIG. 6-(B), which is outside of the measuring range.

In the case of FIG. 6-(B), the distance between the signal substance generator 11 and the the detection means (c) is a medium-to-long distance type or a short-to-long distance type, while that of the case of FIG. 6-(C) is a long distance type. In consequence, signals measured after (until) a predetermined elapsed time are medium in the case of FIG. 6-(B) and very small or zero in FIG. 6-(C).

In other words, as shown in FIG. 7-(B), the signal strength becomes small in proportion to the amount of the substance to be assayed 14 but increases again as the amount of the substance to be assayed 14 exceeds the measurable range.

Thus, the relationship between the amount of the substance to be assayed 14 and the distribution conditions of the signal substance generator 11 in the matrix (b) in the assay process of the present invention has been described. Next, examples of immunological reactions (specific binding reaction) in the matrix (b) are described in which a component of the immunological reaction system is the substance to be assayed which is most suited to the assay process of the present invention.

A first example is a case which is preferable when the substance to be assayed is a hapten-like low molecular weight substance. In such a case, a substance (or an analogue thereof) which is identical to the substance to be assayed is immobilized in the matrix (b), a compound obtained by binding a labeling agent (for example, an enzyme which takes part in the generation reaction of a signal substance) to an anti-hapten antibody as a specific binding substance is used as the signal substance generator, and the substance to be assayed in a test sample and the immobilized substance to be assayed (or an analogue thereof) are allowed to undergo competitive binding to the antibody portion of the signal substance generator. As a result, the relationship between the amount of the substance to be assayed and the signal strength shows the pattern of FIG. 7-(A).

A second example is a case which is preferable when the substance to be assayed is a high molecular weight substance that can bind to a plurality of antibodies at the same time. In such a case, antibody specific for epitope A as a first specific binding substance of the substance to be assayed is immobilized in the matrix (b). The thus immobilized antibody is allowed to react with the substance to be assayed, and then the substance to be assayed is allowed to react with a signal substance generator 11 which is a compound obtained by binding a labeling agent to the antibody specific for epitope B as a second specific binding substance of the substance to be assayed. As a result, the relationship between the amount of the substance to be assayed and the signal strength shows a pattern of FIG. 7-(B).

A third example is also a case which is preferable when the substance to be assayed is a hapten-like low molecular weight substance. In such a case, an anti-hapten antibody as a first specific binding substance is immobilized in the matrix (b), a compound obtained by binding a labeling agent to a substance (or an analogue thereof) which is identical to the substance to be assayed and which competes with the substance to be assayed for the first specific binding substance is used as the signal substance generator, and the substance to be assayed in a test sample and the signal substance generator are allowed to undergo competitive binding to the immobilized anti-hapten antibody. As a result, the relationship between the amount of the substance to be assayed and the signal strength shows the pattern of FIG. 7-(A)

A fourth example is a case which is preferable when the substance to be assayed is a hapten-like low molecular weight substance. In such a case, a substance (or an analogue thereof) which is identical to the substance to be assayed and which competes with the substance to be assayed for a specific binding substance is immobilized in the matrix (b) in which an anti-hapten antibody is included in the free state as the specific binding substance, and the substance to be assayed in a test sample and the immobilized substance to be assayed (or an analogue thereof) are allowed to undergo competitive binding to the free anti-hapten antibody, followed by a binding reaction of a signal substance generator obtained by binding a labeling agent to an anti-antihapten antibody (second antibody). As a result, the relationship between the amount of the substance to be assayed and the signal strength shows the pattern of FIG. 7-(A).

In the above description, antibody molecules were immobilized in the matrix (b), and a signal substance generator, a substance to be assayed and the like were allowed to bind to the immobilized antibody directly or indirectly. However, it is possible to change the distribution of the signal substance generator in the matrix (b) in response to the amount of the substance to be assayed without allowing the signal substance generator, the substance to be assayed and the like to bind to the matrix (b), that is, without immobilizing the antibody in the matrix (b). Such a case is also included in the scope of the assay process of the present invention.

For example, when the substance to be assayed is a microorganism (a pathogenic fungus or the like) and the signal substance generator is a labeled specific binding substance obtained by binding a labeling agent to an anti-microorganism antibody (anti-pathogenic fungus antibody or the like), the travel speed or reaching point of a complex of the substance to be assayed and the signal substance generator in the matrix (b) is considerably different from that of the free-state signal substance generator, because the size of the substance to be assayed (microorganism) is fairly large in comparison with the signal substance generator. Such a difference in the reaching point becomes more clear when a porous material is used as the matrix (b) and its mesh (pore) size is correctly selected, or when a gel or sol carrier is used as the matrix (b) and its viscosity is selected correctly in response to the size of the microorganism. In consequence, the substance to be assayed is not bound to the matrix (b) but its distribution in the matrix (b) is localized, and the signal substance generator which is capable of undergoing a specific binding reaction with the substance to be assayed is distributed in the matrix (b) in response to the amount of the substance to be assayed in the matrix (b). As a result, the substance to be assayed can be determined quantitatively by measuring signals related to the free-state signal substance generator which reaches a position close to the detection means (c).

As another example, the measurement may be effected by making use of the formation (gel immunoprecipitation reaction) of a spontaneous precipitation complex (immunoprecipitate) of a labeled antibody and a substance to be assayed both in the free state. In such a case, the amount of the formed immunoprecipitate changes in response to the amount of the substance to be assayed and the formed immunoprecipitate is trapped in an upper area of the matrix (b) which comprises a porous material and/or a gel carrier, but the free-state labeled antibody which did not take part in the immunoprecipitation reaction can travel inside of the matrix (b). As a result, the distribution of the signal substance generator changes in response to the amount of the substance to be assayed in a test sample.

Alternatively, when a material of proper hole size is used as the matrix (b), a substance to be assayed (microorganism) can be trapped in the upper area of the matrix (b), thereby effecting distribution of a signal substance generator in the matrix (b) in response to the amount of the substance to be assayed in the manner as shown in FIGS. 6A–6C.

Next, generation of signals in the assay process of the present invention is described in detail.

The following describes a typical example in which an enzyme-labeled specific binding substance is used as the signal substance generator, based on FIGS. 1A, 1B and 8 and Table 1.

In this case, when a substance related to the generation of a signal substance (P-aminophenyl-α-D-galactoside) 12 reaches a signal substance generator (α-galactosidase-labeled specific binding substance) 11 in a matrix (b), the

TABLE 1

Reaction types of signal generation

Type 1 (signal, electron; detection means, electrode)

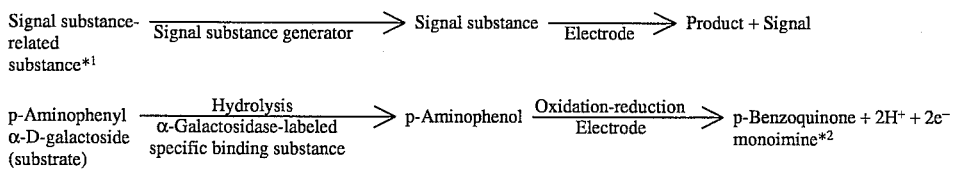

Type 2 (signal, electron; detection means, electrode)

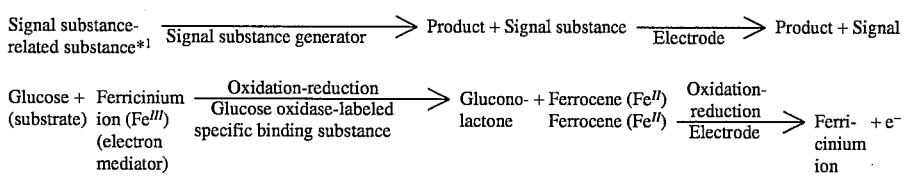

Type 3 (signal, electron; detection means, enzyme electrode)

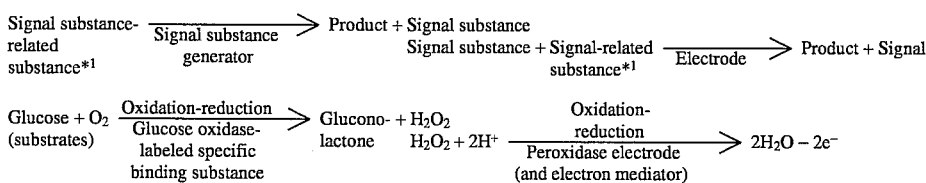

Type 4 (signal, fluorescence or emission; detection means, immobilized enzyme and/or substrate)

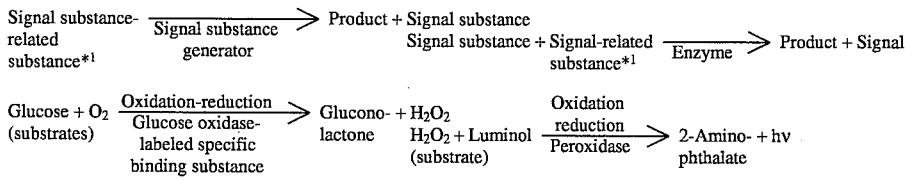

Type 5 (signal, color; detection means, immobilized enzyme and/or substrate)

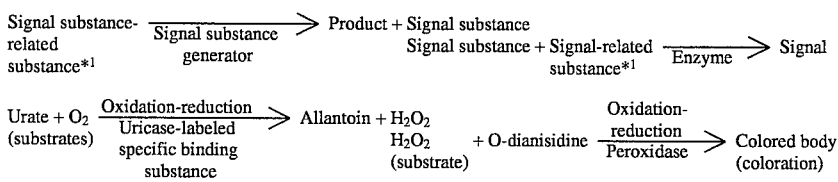

*1, Substance related to signal substance generation
*2, 4-imino-2,5-cyclohexadiene-1-one Table 1 shows five typical examples of the signal generation in the assay process of the present invention. In each column of the table, the upper row shows an example of the signal generation steps using the terminology of this invention, and the lower row explains the steps using illustrative terms.

The type 1 is an example in which an electrode is used as the detection means (c) and electron transfer is used as the signal. The following describes this type of signal generation based on FIGS. 1A and 1B.

substance related to the generation of a signal substance 12 is converted into a signal substance (p-aminophenol) 13. When the signal substance 13 reaches the detection means (electrode) (c) by diffusion, the signal substance 13 is converted into p-benzoquinone monoimine by oxidation and, at the same time, generates an oxidation current (electron transfer) as a signal. Thereafter, values related to the electron transfer signal are measured as the quantity of electricity or current values.

The type 2 is an example in which an electrode is used as the detection means (c), electron transfer is used as the signal and an electron mediator is used for the transfer of electron. The following describes this type of signal generation based on FIGS. 1A and 1B.

In this case, when a substance related to the generation of a signal substance (a combination of glucose and ferricinium ion as an electron mediator) 12 reaches a signal substance generator (glucose oxidase-labeled specific binding substance) 11 in a matrix (b), the ferricinium ion is converted into a signal substance (ferrocene) 13. When the signal substance 13 reaches the detection means (electrode) (c) by diffusion, the signal substance 13 is oxidized (reversed into the oxidized snare ferricinium ion) and, at the same time, generates an oxidation current (electron transfer) as a signal. Thereafter, values related to the electron transfer signal are measured as the quantity of electricity or current values. In this instance, diffusion transfer of the electron itself between electron mediators by electron hopping or the like and measurement of the resulting signal (electron transfer) generated at the detection means (c) may also be applicable.

The type 3 is an example in which an enzyme electrode is used as the detection means (c) and electron transfer is used as the signal. In this case, it is possible to include an electron mediator and/or an electrically conductive high molecular weight compound (polypyrrole, polythiophene or the like) as composing elements in the enzyme electrode portion, in order to improve performance of the enzyme electrode. Reaction of a signal substance with a detection means (enzyme electrode) and resulting direct or indirect generation of a signal (electron transfer) are not affected by these composing elements. Preferred examples of the signal substance include a substrate, a cofactor, a coenzyme and the like which correspond to the enzyme electrode. When the signal substance generates a signal in concert with other substances, that is, when the enzyme electrode generates a signal in the presence of the signal substance and other substances which take part in the signal generation, the signal generation-related substance may be located on the detection means (c) and/or in an area close to the detection means (c). The following describes this type of signal generation based on FIG. 8.

In this case, when a substance related to the generation of a signal substance (a combination of glucose and dissolved oxygen) 12 reaches a signal substance generator (glucose oxidase-labeled specific binding substance) 11 in a matrix (b), a signal substance (hydrogen peroxide) 13 is formed. When the signal substance 13 reaches the detection means (peroxidase electrode) (c), the signal substance 13 receives an electron from the electrode, mediated or not mediated by an electron mediator, and reacts with a substance related to the generation of a signal (hydrogen ion) 15. In this way, the signal substance 13 is reduced and, at the same time, a signal (electron transfer) is generated at the detection means (peroxidase electrode) (c).

The type 4 is an example in which the detection means (c) is a part where an enzyme (peroxidase) is substantially immobilized and luminescence is used as the signal. In this case, the signal substance 13 itself does not generate the signal. The following describes this type of signal generation based on FIG. 8.

In this case, when a substance related to the generation of a signal substance (a combination of glucose and dissolved oxygen) 12 reaches a signal substance generator (glucose oxidase-labeled specific binding substance) 11 in a matrix (b), a signal substance (hydrogen peroxide) 13 is formed. When the signal substance 13 reaches the detection means (peroxidase-immobilized part) (c) together with a substance related to the generation of a signal (luminol) 15, the substance related to the generation of a signal 15 is changed and, at the same time, a signal (luminescence) is generated. Thereafter, the luminescence strength after or until a predetermined elapsed time is measured.

The type 5 is an example in which the detection means (c) is a part where an enzyme (peroxidase) is substantially immobilized and coloration is used as the signal. In this case, the signal substance 13 itself does not generate the signal. The following describes this type of signal generation based on FIG. 8.

In this case, when a substance related to the generation of a signal substance (a combination of urate and dissolved oxygen) 12 reaches a signal substance generator (uricase-labeled specific binding substance) 11 in a matrix (b), a signal substance (hydrogen peroxide) 13 is formed. When the signal substance 13 reaches the detection means (peroxidase-immobilized part) (c) together with a substance related to the generation of a signal (orthodianisidine) 15, the substance related to the generation of a signal 15 is changed to a colored body and, at the same time, a signal (coloration) is generated. Thereafter, coloration after or until a predetermined elapsed time is measured by detecting absorbance or reflected light of the color or visually observing the color.

In the above types 4 and 5, either of the signal generation-related substance (enzyme reaction substrate) or the immobilized substance (enzyme) which constitutes the detection means (c) may be used as the substance related to the generation of a signal. In that instance, the remaining substance is used as the immobilized substance which constitutes the detection means (c). In other words, the substrate and the enzyme are mutually exchangeable. As an alternative, the detection means (c) may be constructed by immobilizing both the substrate and the enzyme. In any case, excellent reaction efficiency may be obtained when at least the enzyme is immobilized.

Also, in the above types 1 to 5, it is possible to exchange the substance related to the generation of a signal substance (corresponding to an enzyme reaction substrate, but not the dissolved oxygen) and the labeled substance (enzyme) which constitutes the signal substance generator. In that instance, however, it is preferable to use the enzyme as the labeled substance in view of excellent reaction efficiency.

The following Table 2 shows an example of the combination of an enzyme (a label, a composing element of the signal substance generator in Table 1), which is suitable for use in the generation of a signal substance, with its substrate (a substance related to the generation of the signal substance in Table 1).

TABLE 2

| Enzyme | Substrate | Signal substance to be generated |
| --- | --- | --- |
| Uricase | Urate, $O_2$ | $H_2O_2$ |
| Choline oxidase | Choline, $O_2$ | $H_2O_2$ |
| Cholesterol oxidase | Cholesterol, $O_2$ | $H_2O_2$ |

TABLE 2-continued

| Enzyme | Substrate | Signal substance to be generated |
| --- | --- | --- |
| Oxalate oxidase | Oxalate, $O_2$ | $H_2O_2$ |
| Sarcosine oxidase | Sarcosine, $O_2$ | $H_2O_2$ |
| Superoxide dismutase | Pyrogallol | $H_2O_2$ |
| Xanthine oxidase | Xanthine, $O_2$ | $H_2O_2$ |
| Glucose oxidase | Glucose, $O_2$ | $H_2O_2$ |
| Horseradish peroxidase | Hydrogen donor (reduced type), $H_2O_2$ | Hydrogen acceptor (oxidized type) |
| α-Galactosidase | p-Aminophenyl-α-D-galactoside | p-Aminophenol |
| β-Galactosidase | p-Aminophenyl-β-D-galactoside | p-Aminophenol |
| Alkaline phosphatase | p-Aminophenyl phosphate | p-Aminophenol |
| Phosphodiesterase | Bis-p-aminophenyl phosphate | p-Aminophenol |
| Lactate dehydrogenase | Lactate, $NAD^+$ | NADH |
| Formate dehydrogenase | Formate, $NAD^+$ | NADH |
| β-Galactose dehydrogenase | Galactose, $NAD^+$ | NADH |
| 3-Hydroxybutyrate dehydrogenase | 3-Hydroxy butyrate, $NAD^+$ | NADH |
| Glucose-6-phosphate dehydrogenase | Glucose-6-phosphate, $NADP^+$ | NADPH |
| 6-Phosphogluconate dehydrogenase | Gluconate-6-phsophate, $NADP^+$ | NADPH |
| Pyruvate kinase | Phosphoenol pyruvate, ADP | ATP |
| α-Galactosidase | Raffinose | Galactose |
| β-Galactosidase | Lactose | Galactose, glucose |
| Citrate lyase | Citric acid | Oxaloacetic acid |
| Pyruvate kinase | Phosphoenol pyruvate, ADP | Pyruvate |
| Phosphoglucomutase | Glucose-1-phosphate Glucose-1,6-diphosphate | Glucose-6-phosphate |

Each of the combinations shown in Table 2 can be applied to the signal generation types 1, 3, 4 and 5 described above. However, in case of the type 1 in which a signal is generated by an oxidation-reduction reaction of a signal substance on an electrode, it is preferable to use such a combination that p-aminophenol, hydroquinone, p-cresol or the like is generated as a signal substance. Electron transfer from such a signal substance to an electrode occurs when an electric potential of + several hundred mV is applied based on an Ag/AgCl electrode.

In the case of the signal generation type 2, an oxidation-reduction substance (oxidation state) known as an electron mediator is used instead of $O_2$. By the use of such a substance, the reaction shown in Table 1 is effected in which a signal substance (an electron mediator in the reduction state) is generated, electrons are released from the signal substance to an electrode charged with an electric potential corresponding to the electron mediator in the same manner as the case of the type 1, and the electron mediator itself returns to its oxidation state.

A number of substances are known as electron mediators which include for example metal ions, ruthenium complex compounds, ferrocene compounds, quinone compounds, viologen compounds, porphyrin derivatives and proteins such as cytochrome c. Also included are compounds which take part in enzyme reactions as hydrogen donors. Typical examples of electron mediators are shown in Table 3, though chemically modified products of these examples or other suitable electron mediators can also be used. In addition, electron mediators are not limited to those which change from the oxidation state to the reduction state, but those having the function to change from the reduction state to the oxidation state may also be used.

TABLE 3

Typical electron mediator

Ferrocene
Vinyl ferrocene
Ferrocene acetatic acid
Ferrocene monocarboxylic acid

TABLE 3-continued

Typical electron mediator 1,1'-bishydroxymethylferrocene (BHMF)
$Ru(bpy)_3$
$Os(bpy)_3$
$Fe(bpy)_3$
$Fe(phen)_3$
$Ru(bpy)_2(im)_2$
$Mo(CN)_8$
$K_2Fe(phen)(CN)_4$
$Co(phen)_3Cl_2$
$K_4Fe(CN)_6$ or $K_3Fe(CN)_6$
Hydroquinone
p-Benzoquinone
Catechol
p-Quinone-dioxime
p-Methylphenol
Hydroquinone sulfonic acid
Hydroxyhydroquinone
N,N-Dimethyl-p-phenylenediamine (DMPD)
N,N,N',N'-Tetramethyl-p-phenylenediamine (TMPD)
2,6-Dichlorophenolindophenol
1,2-Naphthoquinone
Phenazine methosulfate (PMS)
5-Hydroxy-1,4-naphthoquinone
Pyocyanine
2-Amino-6,7-dihydro-4-pteridone
2-Amino-1,4-naphthoquinone
Anthraquinone-2-sulfate
2-Amino-4-pteridone
Methylviologen ($MV^{2+}$)
Benzylviologen ($BV^{2+}$)
Metal porohyrin Note: bpy, bipyridyl; phen, o-phenanthroline; im, imidazole The following describes substances which take part in the second stage reaction of the two stage enzyme reactions in the signal generation types 3 to 5 shown in Table 1 in which a signal substance formed by the first stage enzyme reaction reacts with other substances to generate a signal.

The type 3 in Table 1 shows an example in which an enzyme electrode is used as the detection means (c). In this case, the types of enzymes used in the enzyme electrode are limited depending on the types of the signal substance formed by the first stage reaction.

For example, when the signal substance formed by the first stage reaction is hydrogen peroxide, an enzyme electrode to which a peroxidase, such as horseradish peroxidase or the like, has been immobilized may be used as the detection means (c). Enzyme electrodes of this type have been disclosed for instance by J. E. Frew et al. (*J. Electoanal. Chem.*, vol. 201, pp. 1–10, 1986), by R. M. Paddock and E. F. Bowden (*J. Electoanal. Chem.*, vol. 260, pp. 487–494, 1989) and by Ulla Wollenberger et al. (Analytical Letters, vol. 23, pp. 1795–1808, 1990). When the signal substance is $NAD^+$ or NADH, an enzyme electrode to which diaphorase I obtained from a thermophilic bacterium has been immobilized (cf. K. Miki et al., *Analytical Sciences*, vol. 5, pp. 269–274, 1989) may be used as the detection means (c).

When these enzyme electrodes are used as the detection means (c), an electron mediator is used as a substance related to the generation of a signal in some cases as shown in Table 1. Examples of the electron mediator are already shown in Table 3.

Chemically modified electrodes are known as analogous means of the enzyme electrode, which are disclosed for instance by R. W. Murray (Chemically Modified Electrode, *Electroanalytical Chemistry*, vol. 13, pp. 191–368, Marcel Dekker, Inc., New York, 1084), by K. Nakamura, M. Aizawa and O. Miyawaki (*Electroenzymology Coenzyme Regeneration*, Springer-Verlag, Berlin, 1988) and by V. J. Razumas, J. J. Jasaitis and J. J. Kulys, *Bioelectrochemistry and Bioenergetics*, vol. 12, pp. 297–322, 1984).

When the signal is fluorescence or luminescence like the case of the type 4 signal generation system shown in Table 1, substances which take part in the second stage reaction (an enzyme and a fluorescent or luminescent substance as a substrate of the enzyme) are restricted depending on the types of signal substance formed by the first stage reaction.

For example, when the signal is fluorescence and the signal substance is hydrogen peroxide, a typical combination of the substances related to the second stage reaction may be peroxidase with 4-hydroxyphenyl acetate or 3-(4-hydroxyphenyl) propionate.

When the signal is luminescence and the signal substance is ATP, a typical combination of the substances related to the second stage reaction may be firefly luciferase with luciferin and $Mg^{2+}$.

When the signal substance is NADH, the combination of the substances related to the second stage reaction may be NAD(P)H:FMN oxidoreductase and a luciferase of luminescent bacterial origin with FMN and a saturated long chain aliphatic aldehyde such as tetradecanal.

In these examples, the detection means (c) may be constructed by immobilizing at least one of the substances which takes part in the second stage reaction, but preferably an enzyme from a reaction efficiency point of view.

When fluorescence or luminescence is used as a signal, it is possible to generate the signal from a signal substance itself, like the case of the type 1 signal generation system shown in Table 1.

For example, luciferin is formed as the signal substance when a luciferin derivative such as D-luciferin-o-phosphate is used as the substance related to the signal substance generation and alkaline phosphatase is used as a labeling agent which constitutes the signal substance generator, and luminescence (signal) is generated when the signal substance (luciferin) is treated with luciferase in the presence of ATP and Mg2+. In this instance, the detection means (c) may be constructed by immobilizing at least one of ATP, $Mg^{2+}$ and luciferase, but preferably luciferase from a reaction efficiency point of view.

When the signal is coloration like the case of the type 5 signal generation system shown in Table 1, substances which take part in the second stage reaction (an enzyme and a precursor of a coloring body as a substrate of the enzyme) are also restricted depending on the types of the signal substance formed by the first stage reaction.

For example, when the signal substance is hydrogen peroxide, a typical combination of the substances related to the second stage reaction may be peroxidase with a coloring substance precursor such as a mixture of 5-aminosalicylic acid, o-dianisidine, 2,2'-azino-di-(3-ethylbenzothiazoline-6-sulfonate) diammonium salt (ABTS), 3-methyl-2-benzothiazolinehydrazone (MBTH) and 3-(dimethytamino)benzoic acid (DMAB), or o-tolidine, 3,3'-diaminobenzidine ((DAB), 1,2-phenylenediamine, 3,3'-5,5'-tetramethylbenzidine or the like.

When the signal substance is NADH, the combination of the substances related to the second stage reaction may be diaphorase with a coloring substance precursor such as iodonitrotetrazolium violet.

In these examples, the detection means (c) may be constructed by immobilizing at least one of the substances which take part in the second stage reaction, but preferably an enzyme from a reaction efficiency point of view.

Thus, though not particularly limited, illustrative examples of the signal generation mechanism in the assay process of the present invention have been described.

In the assay process of the present invention, signals are generated in the aforementioned manner and then measured by an appropriate means. For example, though not particularly limited, the measurement may be effected by the use of electric measuring instruments such as a potentiostat, a coulomb meter, an ammeter and the like when the signal is electron transfer, a fluorophotometer when the signal is fluorescence, and a luminometer when the signal is luminescence. When the signal is coloration, it may be measured by visual judgment or by the use of a color-difference meter, an absorptiometer, a reflectiometer or the like.

Though an end point measurement is applicable, it is preferable to measure signal strength modulation for a certain period of time, because signals are generally supplied continuously. The concentration of a substance to be assayed in a test sample is calculated by comparing the degree of modulation measured for an unknown concentration of the substance to be assayed with the degree of modulation which corresponds to a known concentration of the substance to be assayed. In this instance, it is possible to incorporate modulation degrees for known concentrations of the substance to be assayed into a calculator in advance, for the purpose of simplifying the measurement.

Next, the specific binding assay device of the present invention which is useful for the practice of the aforementioned inventive assay process is described in the following.

The assay device of the present invention comprises a sample-introducing means (a), a matrix (b) and a detection means (c), or a sample-introducing means (a), a matrix (b), a detection means (c) and an absorption means (d). When required, the aforementioned substance related to the generation of a signal substance is located at an appropriate test sample-flowing part of the assay device.

The following describes the assay device of the present invention with reference to the drawings attached hereto.

Side views of examples of the assay device of the present invention are shown in FIG. 9 (A) to (E) and (G), (H) and a plan view of an example in FIG. 9 (F).

As shown in the figure, the sample-introducing means (a) may be arranged as an independent means [cf. FIG. 9 (A), (B), (D), (E), (G) and (H)], or a portion of the matrix (b) may be used as the sample-introducing means (a) [cf. FIG. 9 (C) and (F)].

The matrix (b) is a place arranged downstream of the sample-introducing means (a), where a specific binding reaction is carried out. When the assay device of the present invention also comprises the absorption means (d) [cf. FIG. 9 (B), (D) and (H)], the absorption means (d) may be separated from the matrix (b) [cf FIG. 9 (B) and (H)], or a downstream portion of the matrix (b) may be used as the absorption means (d) [cf. FIG. 9 (D)], provided that the absorption means (d) does not function as a field of the specific binding reaction.

The detection means (c) may be arranged at a position where the effect of signal modulation originating from the distributional changes of a signal substance generator in the matrix (b) is high. In general, the detection means (c) may be arranged in the most downstream side of the matrix (b) [cf. FIG. 9 (A), (B), (C), (D), (F) and (G)] or in the most upstream side [cf. FIG. 9 (H)].

The detection means (c) may be arranged as an independent area, or a portion of the matrix (b) or the absorption means (d) may be processed to be used as the detection means (c). Such a processing can be applied to any of the examples shown in FIG. 9 (A), (B), (C), (F) and (G).

The assay device of the present invention may also comprise a support (or a base) (e) and a cover (f) [cf. FIG. 9 (G) and (H)].

Next, each part of the assay device of the present invention ms described in detail.

When the sample-introducing means (a) is an independent means, it may be prepared from a porous filter, such as a cellulose filter paper, a glass fiber filter paper, a non woven fabric or the like, which has an appropriate size that corresponds to the amount of a test sample. Independent use of the sample-introducing means (a) is preferable, because addition of a test sample can be carried out easily, the test sample permeates into the matrix (b) uniformly and interfering elements in the test sample, such as high molecular weight aggregates, particles and the like, can be removed to a certain degree.

The matrix (b) may be prepared from for example a porous carrier or a gel carrier. In the case of a gel carrier, it is preferable to use a material which becomes a gel or sol when contacted with a test sample. Alternatively, a porous carrier may be impregnated with a water soluble high molecular weight compound and then dried for use as the matrix (b). A material in which a solid substance is kept in the porous carrier or the like may also be used as the matrix (b).

Illustrative examples of the porous carrier include: porous membranes made of cellulose acetate, cellulose nitrate, nylon and the like; filter papers made of glass fibers, cellulose fibers and the like; and porous ceramics and the like. Illustrative examples of the gel carrier include agar, agarose, dextran, polyacrylamide and the like. Illustrative examples of the water soluble high molecular weight compound include starch and derivatives thereof, mannan, galactan, agar, agarose, sodium alginate, gum arabic, dextran, gelatin, casein, collagen, methyl cellulose (MC), ethyl cellulose (EC), hydroxyethyl cellulose (HEC), carboxymethyl cellulose (CHC), polyvinyl alcohol (poval), sodium polyacrylate and the like. Illustrative examples of the solid substance described above include porous particles such as dextran and the like, latexes made of polystyrene and the like, and fine particles such as glass and the like or modified products thereof produced by adding active groups for binding use.

Since the matrix (b) is a site where a specific binding reaction is carried out as described in the foregoing, constitution of this part exerts a great influence on the detection results. In consequence, it is desirable to constitute the matrix (b) in such a manner that it exhibits appropriate properties in response to the kind of substances to be assayed, the type of specific binding reactions (for example, inhibition type, competitive type and sandwich type) and the like conditions. That is, distribution conditions of a signal substance generator and diffusion velocities of a signal substance and the like are controlled optionally by selecting appropriate material for the matrix (b) and adjusting its size (thickness), pore size, viscosity when a gel material is employed and the like.

Properties of the matrix (b) can be controlled easily when it is made into a laminated body. For example, difference in the distribution of a signal substance generator after a specific binding reaction, in response to the amount of a substance to be assayed, can be detected more clearly when a material having a small pore size is used in the downstream side (detection means (c) side) of the matrix (b) and another material having a large pore size is used in its upstream side (sample-introducing means (a) side). Such an effect may be realized by the use of a polyacrylamide gradient gel or laminated porous membranes having different pore sizes.

When a specific binding substance for a substance to be assayed is included or immobilized in the matrix (b), it may be included or immobilized uniformly in the entire area of the matrix, or by making a concentration gradient in the matrix for example by including or immobilizing the specific binding substance in a large amount in the upstream area (sample-introducing means (a) side) of the matrix and in a small amount in its downstream area (detection means (c) side).

Immobilization of a specific binding substance for a substance to be assayed in the matrix (b) may be attained by immobilizing it in a porous carrier or a gel carrier through covalent bonding or adsorption. In addition, when the matrix (b) is constructed with a porous carrier and a water soluble high molecular weight compound, or with a porous carrier or the like and a solid state substance to be kept in the carrier or the like, immobilization of a specific binding substance may be applied to all of the matrix-composing elements or to a part of them.

When the matrix (b) is constructed by immobilizing a specific binding substance which is specific for a substance to be assayed, the matrix (b) may be composed of only a solid state substance in which the specific binding substance has been immobilized. For example, as shown in FIG. 10 (F), the assay device of the present invention may be constructed by packing the solid state substance in a hollow cylinder support (e) and forming a detection means (c) in the downstream end of the support.

Length in the flow direction of a test sample of the matrix (b) of the assay device of the present invention may be generally in the range of from about 10 μm to several mm, because the necessary amount of a liquid test sample can be minimized by reducing the matrix volume, but changes in the distribution of a signal substance generator in response to the amount of a substance to be assayed in the test sample become unclear when the matrix volume is too small.

Though not particularly limited, the matrix (b) of the assay device of the present invention may have various shapes such as a flat body, a laminate of flat bodies, a cuboid, a cylindrical body, a capillary type, a conical body and the like or combinations thereof. Perspective diagrams of some examples of the matrix shape of the assay device of the present invention are shown in FIGS. 10A–10H.

The detection means (c) can also have various constitutions.

Firstly, the constitution when the detection means (c) is an electrode is described.

Various types of electrodes can be used, such as a platinum electrode, a gold electrode, a carbon electrode and the like, of which a carbon print electrode is particularly preferred from a production point of view. In this case, a liquid-impermeable plate such as a vinyl chloride plate or a liquid-permeable sheet (FIG. 9 (B), d) such as a filter paper may be used as an electrode base (FIG. 9 (G) e).

When a minute electrode constitution is required, a microarray electrode may be constructed making use of photographic techniques.

An Ag/AgCl electrode or the like may be used as a reference electrode of for the above electrode, which can be produced making use of printing techniques and the like.

Specificity and sensitivity of the electrode reaction can be improved when an enzyme electrode is used as the detection means (c). In that instance, a signal substance functions as a substrate or a cofactor of the enzyme electrode, and a signal is detected when electron transfer is effected on the electrode. Various types of the enzyme electrode are known in the fields of biochemical analysis and analytical chemistry.

When the detection means (c) is a site where fluorescence, luminescence, coloring or the like is detected, the detection means (c) is actually a fluorescence generation part where a substance which takes part in at least one signal generation necessary for the fluorescence reaction is substantially immobilized, a luminescence generation part where a substance which takes part in at least one signal generation necessary for the luminescence reaction is substantially immobilized or a color generation part where a substance which takes part in at least one signal generation necessary for the coloring reaction is substantially immobilized.

According to the signal generation types 4 and 5 shown in Table 1, the substance to be immobilized as a constituent of the detection means (c) is luminol and/or peroxidase (Type 4) or orthodianisidine and/or peroxidase (Type 5). However, it is preferable to constitute the detection means (c) by immobilizing at least the enzyme from a reaction efficiency point of view.

When the detection means (c) is a site where fluorescence, luminescence, coloring or the like is detected, the detection means (c) may be prepared by immobilizing the aforementioned signal generation-related substance in an area of the aforementioned matrix (b) or of an absorption means (d) which will be described later, or on a base (e) when the base (e) is arranged in the downstream side of the detection means (c) like the case shown in FIG. 9 (G). In that instance, the immobilization may be effected by various means, for example, by binding an enzyme of interest using glutaraldehyde to the surface of a glass base which has been treated with 3-aminopropyltriethoxysilane.

When an absorption means (d) is used [cf. FIG. 9 (B), (D) and (H)], the absorption means (d) is constructed with a porous carrier, a gel carrier or the like which have been described in the foregoing in relation to the matrix (b). It may also be made into a laminated body. In any case, a specific binding substance specific for a substance to be assayed is not included or immobilized in the absorption means (d) in general, when the specific binding substance is included or immobilized in the matrix (b).

In addition to the aforementioned composing elements, the assay device of the present invention may have a portion which corresponds to a support or base (e) and/or a portion that corresponds to a cover (f). The support or base (e) may be arranged for example in the downstream area of the detection means (c) like the case of FIG. 9 (G) or by surrounding the device with the support or base (e) like the case of FIG. 10 (F). The cover (f) may be arranged for example in the upstream area of the sample-introducing means (a) like the case of FIG. 9 (G) and (H). In addition, a pore (g) may be applied to the cover (g) for use in the introduction of a test sample.

In this instance, the term "support or base (e)" means a part which has been prepared from a water-impermeable material, and a part prepared from a water-permeable material is used as the absorption means (d). Also, the term "cover (f)" means a part which has been prepared from a water-impermeable material, and a part prepared from a water-permeable material is used as the sample-introducing means (a).

Examples of the construction materials of the support or base (e) and the cover (f) include polyvinyl chloride, glass, acrylic resin, polystyrene, ABS resin, epoxy resin and the like, which may be transparent or opaque. However, the support or base (e) may be transparent when the matrix (b) has the constitution of FIG. 9 (G) and the signal is fluorescence, luminescence, coloring or the like.

In the assay device of the present invention, a substance related to the generation of at least one signal substance is located in at least one of the sample-introducing means (a), the matrix (b) and the detection means (c) or in at least one of the sample-introducing means (a), the matrix (b), the detection means (c) and the absorption means (d). Such a substance has already been described in the foregoing in relation to the assay process of the present invention.

This substance related to the generation of a signal substance is located in the aforementioned manner because, when a test sample is introduced into the assay device of the present invention, this substance is carried away with the sample flow into an area close to the detection means (c) or into the absorption means (d). That is, the substance 12 related to the generation of a signal substance is transferred to the position shown in FIGS. 1A and 1B or 6A–6C, or to the position of the absorption means (d) shown in FIG. 9 (B) or (D). However, it is preferable to locate the substance 12 in an area close to the detection means (c) and/or in the absorption means (d) from an accuracy point of view.

Thus, the constitution of the assay device of the present invention has been described. In addition to this, substances other than the substance 12 related to the generation of a signal substance, which are necessary for the reaction in the assay process of the present invention, may also be located (adhered) in appropriate areas of the assay device of the present invention.

Illustrative examples of such substances include: a signal substance generator; a substance related to the generation of a signal in the case of the type 3 signal generation system shown in Table 1; and a substance which is not immobilized for the formation of a detection means (c) in the case of the type 4 or 5 in Table 1, that is, either an enzyme or its substrate which is not immobilized.

When these substances are not located in the assay device of the present invention, they are introduced into the device together with a test sample or before or after the introduction of the test sample. However, it is desirable to locate these substances in advance in appropriate areas of the assay device, because a step for their introduction into the assay device can be omitted. In this instance, most desirable assay device may contain all substances necessary for the reaction in the assay process of the present invention, except for a substance to be assayed in a test sample and a substance generally contained in a test sample (dissolved oxygen for example). By the use of such a device, a specific binding assay can be effected only by introducing a test sample and judging the results.

When these substances necessary for the specific binding assay are located in the assay device of the present invention, like the case of the aforementioned substance related to the generation of at least one signal substance, substances other than the signal substance generator are located in at least one of the sample-introducing means (a), the matrix (b) and the detection means (c) or in at least one of the sample-introducing means (a), the matrix (b), the detection means (c) and the absorption means (d).

The signal substance generator, on the other hand, is located in the sample-introducing means (a) and/or in an upstream area of the matrix (b) of the assay device of the present invention, because it should undergo a specific binding reaction and be distributed in the matrix (b) in response to the amount of a substance to be assayed in a test sample.

Though an assay device having a single detection means (c) or a device which corresponds to a single substance to be assayed has been described in the foregoing, the assay device of the present invention may have a plurality of the detection means (c). For example, when a plurality of the detection means (c) are arranged and distribution of a signal substance generator is measured at a plurality of detection sites, accuracy of the assay will be improved considerably. Also, when a plurality of the detection means (c) are arranged, different types of signals can be detected and therefore a plurality of substances to be assayed can be measured.

The assay device of the present invention can be used as it is when a signal is detected by visual observation, but should be used by connecting it to an appropriate detecting element (a measuring instrument) depending on the type of the signals. Such detecting elements or measuring instruments have already been described in the foregoing in relation to the assay process of the present invention.

Next, application methods of the assay device of the present invention are described.

When the assay device of the present invention contains all necessary substances for the reaction, a specific binding assay may be effected by introducing a predetermined amount of a test sample into the sample-introducing means (a) and by measuring signals after a predetermined period of time or continuously until a predetermined period of time.

When a test sample is loaded, liquid components in the test sample permeate toward the detection means (c) by gel permeation, diffusion, or capillary action. In this instance, a substance related to the generation of a signal substance and a substance related to the generation of a signal are once carried away together with the test sample by diffusion to the downstream side of the matrix (b) or to the absorption means (d) and then distributed in the reaction device by reverse direction, independent of their original location in the sample-introducing means (a), the matrix (b), the detection means (c) or the absorption means (d). On the other hand, a substance to be assayed and a signal substance generator react each other while traveling in the matrix (b) or are trapped in a certain area in the matrix (b) when a specific binding substance is immobilized. When the signal substance generation-related substance, which has once been carried away to an area close to the detection means (c) or to the absorption means (d), is transferred to the signal substance generator, it is converted into a signal substance, and the signal substance is subsequently transferred to the detection means (c) by means of a mass transfer (diffusion) and generates a signal directly, or indirectly through its reaction with the substance related to the generation of a signal.

When the assay device of the present invention lacks some of the necessary substances, these lacking substances are introduced to the assay device prior to, together with or after the introduction of a test sample. In general, the substance related to the generation of a signal substance and the substance related to the generation of a signal are dissolved in an appropriate buffer solution or the like and introduced into the device prior to the introduction of a test sample. When introduced, these substances diffuse into the reaction device and attain a steady state. The signal substance generator is introduced into the device together with or after the introduction of a test sample. Movement and reaction of each substance in the matrix (b), generation of a signal at the detection means (c) and other behavior of these substances are the same as in the case of the aforementioned assay device which contains all of the necessary substances.

Thus, the assay process and the assay device of the present invention have been described. The following describes an assay process in which a substance to be assayed (hCG) is measured by using $\alpha$-galactosidase as a composing element (labeling agent) of the signal substance generator and by detecting a signal based on electrochemical means, and a device for use in such an assay process, as an illustrative example of the specific binding assay process and device of the present invention.

Two monoclonal anti-hCG antibodies, HM21 and HM81, which recognize different epitopes of the hCG molecule are used, one of them (HM21) as immobilized antibody in the matrix (b) and the other (HM81) as a composing element of the signal substance generator. That is, the signal substance generator is the $\alpha$-galactosidase-labeled HM81 antibody. The HM21 antibody is adsorbed and immobilized to a porous nylon film carrier, a plurality of the resulting films are laminated corresponding to the hCG measuring range and the laminate is used as the matrix (b). The detecting means (c) is prepared by printing an Ag/AgCl reference/counter electrode and a carbon working electrode. On the thus prepared detection means (c) is superposed a porous nylon film (substrate layer which constitutes a part of the matrix (b)) which has been impregnated with p-aminophenyl-$\alpha$-D-galactopyranoside as an enzyme reaction substrate (the substance related to the generation of a signal substance). On the resulting laminate are further superposed the matrix (b) prepared above and a filter paper as the sample-introducing means (a) in that order. Adhesion of these layers is effected by the use of a hydrophilic gel such as agarose. The thus prepared laminate is used as a test piece for the hCG assay. Prior to the hCG measurement, an electric potential of +400 mV per Ag/AgCl reference electrode is applied to the working electrode side of the detection means (c) which is further arranged in such a manner that currents or charges flowing toward the working electrode or the counter electrode can be measured.

When a test sample is introduced into the sample-introducing means (a) together with a predetermined amount of the signal substance generator (α-galactosidase-labeled HM81 antibody) and allowed to permeate into the matrix (b), a specific binding reaction complex (immobilized HM21 antibody/substance to be assayed (hCG)/α-galactosidase-labeled HM81) is formed in the matrix (b). In this instance, when the amount of hCG in the test sample is large, the specific binding reaction complex is formed with a high efficiency and, as a result, distribution of the signal substance generator shifts to the upstream side in the matrix (b) (a side distant from the detection means (c)). On the contrary, when the amount of hCG in the test sample is small, distribution of the signal substance generator shifts to the downstream side in the matrix (b) (a side close to the detection means (c)). In this case, a portion of the signal substance generator, especially which failed to react with hCG, approaches an area close to the detection means (c). The test sample permeates further into the substrate layer (most downstream side layer of the matrix (b) where a substrate such as p-aminophenyl-α-D-galactoside is located), reaches the detection means (c) and causes liquid junction between the working electrode and the reference/counter electrode. Permeation of the test sample is substantially stopped at this stage.

At this stage, the substrate in the substrate layer is dissolved and diffused toward the upstream side of the matrix (b). When the thus diffused substrate contacts the signal substance generator, the substrate is hydrolyzed by the enzyme (labeling agent) and converted into a signal substance (p-aminophenol). The thus formed signal substance starts to diffuse round its generation source (signal substance generator) as a center. A portion of the signal substance, which diffused into the detection means (c) side, is subjected to an electrode reaction at the detection means (c) to release electrons. The electron transfer occurring in this way is measured as an electrochemical signal. Since the diffusion distance of this signal substance depends on the distance between the signal substance generator as the generation source of the signal substance and the detection means (c), a signal substance generator portion close to the detection means (c) can supply the signal substance to the detection means (c) more efficiently than a portion which is located in an area distant from the detection means (c). In consequence, the distribution of the signal substance generator in the matrix (b) exerts influence on the strength of a signal (current, charge or the like) measured at the detection means (c). In addition, since such a distribution of the signal substance generator changes in response to the amount of hCG in a test sample, the concentration (quantity) of hCG in the test sample can be measured based on the signal strength.

EXAMPLES

The following examples are provided to further illustrate the present invention. It is to be understood, however, that the examples are for purpose of illustration only and are not intended as a definition of the limits of the invention.

EXAMPLE 1

A specific binding assay device was constructed and hCG concentrations in test samples were measured using the device.

(1) Preparation of a conjugate of anti-hCGβ antibody and α-galactosidase (labeled antibody)

Mouse monoclonal antibody HM81 (Mochida Pharmaceutical Co., Ltd.) which recognizes the β chain of hCG was dissolved in a buffer solution consisting of 100 mM sodium chloride, 1 mM EDTA and 60 mM triethanolamine (pH 8.0, to be referred to as "TEA buffer" hereinafter) to a final concentration of 5.0 mg/ml, and the resulting solution was dialyzed thoroughly against the TEA buffer which has been purged with nitrogen gas. A 10 µl portion of 50 mM 2-iminothiolane hydrochloride (Pierce Chemical Company) solution was added to 0.5 ml of the thus prepared antibody solution, and the mixture was stirred and then allowed to stand still for 2 hours at 4° C. in an atmosphere of nitrogen gas. Thereafter, the resulting solution was dialyzed against TEA buffer which has been purged with nitrogen gas and then against 50 mM phosphate buffer solution containing 100 mM sodium chloride, 1 mM EDTA (pH 6.0, to be referred to as "EDTA-PB" hereinafter) which has also been purged with nitrogen gas. In this way, SH group-introduced anti-hCGβ antibody HM81 was obtained.

A 50 unit portion of α-galactosidase (melibiase, Seikagaku Kogyo Co., Ltd.) was dissolved in 0.5 ml of 50 mM sodium borate buffer (pH 7.6), and the resulting solution was dialyzed thoroughly against the same buffer and then mixed with 1 mg of sulfo-SMCC (Pierce Chemical Company). After 1.5 hours of reaction at 30° C. the resulting reaction mixture was dialyzed against EDTA-PB which has been purged with nitrogen gas to obtain maleimidated α-galactosidase.

A 0.5 ml portion of the SH group-introduced anti-hCGβ antibody HM81 solution was mixed with 0.5 ml of the maleimidated α-galactosidase solution, and the mixture was incubated at 4° C. for 20 hours in an atmosphere of nitrogen gas. After the reaction, 10 µl of 50 mM cysteamine solution was added to the reaction mixture, and the reaction was continued at 4° C. for 30 minutes in an atmosphere of nitrogen gas. Thereafter, the resulting reaction mixture was subjected to gel filtration chromatography using Sephadex G-200 (Pharmacia K.K.) column and Sephacryl S-300HR (Pharmacia K.K.) column which have been equilibrated with EDTA-PB purged with nitrogen.

Each of the thus eluted fractions was checked for its absorbance at 280 nm and for its α-galactosidase activity using a coloring substrate solution for α-galactosidase (10 mM p-nitrophenyl-α-D-galactopyranoside, Sigma Chemical Co.), in order to collect and concentrate fractions containing the anti-hCGβ antibody HM81/α-galactosidase linked product but not containing free enzyme molecules. The thus concentrated preparation of the linked product (to be referred to as "α-galactosidase-HM81" hereinafter) was checked for its molecular weight by a Phast system electrophoresis (Pharmacia K.K.) and used as a signal substance generator in measuring experiments.

(2) Preparation of a detection means (electrode)

Two carbon lines, each having a width of 2 mm and a length of 30 mm, were printed at an interval of 2 mm on a polyvinyl chloride plate (30 mm in length, 15 mm in width and 0.5 mm in thickness) using a conductive carbon ink (Electrodag 114 or Electrodag 109. available from Acheson Japan, Ltd.). A ½ portion in longitudinal direction (15 mm) of one of the carbon lines was further printed with a conductive silver ink (Fujikura Kasei Co., Ltd.), and the thus silver ink-superposed portion was subjected to electrolysis in 0.1M sodium chloride aqueous solution to form a silver chloride layer on the surface.

(3) Preparation of anti-hCGα antibody-immobilized porous nylon film

Mouse monoclonal antibody HM21 (Mochida Pharmaceutical Co., Ltd.) which recognizes the α chain of hCG was dissolved in a 0.076M phosphate-buffered saline (to be referred to as "PBS" hereinafter) to a final concentration of 0.5 mg/ml. A 5×10 mm section of a porous nylon film having a pore size of 3.0 μm (Immunodyne BIAO30HC5, Pall Process Filtration, Inc.) was impregnated with 5 μl of the thus prepared antibody solution to obtain a porous nylon film containing the HM21 solution. After 1 hour of incubation of these nylon film sections at room temperature in a moist box, 1 to 3 ml of a 0.1% bovine serum albumin/PBS solution was added to each section (5×10 mm), followed by 2 to 15 hours of blocking reaction at 4° C. with shaking. Thereafter, the thus treated sections were put in a 0.1% Tween 20/PBS solution and shaken for 2 hours at 4° C. to wash them. By repeating the washing step 3 to 4 times, anti-hCGα antibody (HM21)-immobilized porous nylon films were obtained.

(4) Preparation of a matrix (a part) having a sample-introducing means, by laminating anti-hCGα antibody-immobilized porous nylon film sections Five sections of the anti-hCGα antibody (HM21)-immobilized porous nylon film were put on a filter paper to remove moisture, soaked in a PBS solution containing 0.25% agarose and 0.01% Tween 20 (to be referred to as "hot agarose solution" hereinafter), which has been heated in advance to dissolve the agarose and kept at 50° C., and then immediately laminated on a glass plate.

Next, a 4×8 mm section of quantitative filter paper 5C (Advantech Toyo Co., Ltd.) to be used as a sample-introducing means was soaked in the hot agarose solution and then superposed on the uppermost layer of the nylon film laminate. Immediately thereafter, moisture in the upside portion was removed with a filter paper, and the laminated layers were adhered by pressing them with a pressure of 200 g/section, followed by drying in a desiccator.

(5) Junction of the matrix with the detection means

A piece of the anti-hCGα antibody-immobilized porous nylon film prepared in the above step (3) (a film section impregnated with PBS solution containing 0.5 mg/ml of HM21) was dried and superposed on the detection means (electrode) prepared in the above step (2) in such a manner that the film section covered both the carbon line and the Ag/AgCl line. The thus superposed nylon film was impregnated with 10 μl of a substrate solution which has been prepared by dissolving an enzyme substrate (p-aminophenyl-α-D-galactopyranoside, Sigma Chemical Co.) in the hot agarose solution to a final concentration of 10 mM, and the resulting nylon film was dried. The matrix (a part) having a sample-introducing means prepared in the above step (4) was superposed on the thus prepared detection means and adhered by pressing it with a pressure of 200 g/section. By drying the resulting laminate in a desiccator under a reduced pressure, a specific binding assay device for use in the measurement of hCG concentration was obtained. This device is close to the type shown in FIG. 9 (1).

(6) Measurement

The specific binding assay device thus constructed was connected with Potentiostat HA-150 (Hokuto Denko Co., Ltd.), using the carbon line side as a working electrode and the silver/silver chloride line side as counter/reference electrode. The assay device was further connected with Coulomb Meter HF-203D (Hokuto Denko Co., Ltd.) for use in the measurement of coulomb values, Function Generator HB-104 (Hokuto Denko Co., Ltd.) for use in the setting of electrode potentials and a recorder F-45 (Riken Denshi Co., Ltd.) for use in the recording of signals. The recorder was connected to a computer via a GPIB line to carry out measurement and data processing. When the measurement was carried out, potential of +400 mV was applied to the carbon line electrode side based on the silver/silver chloride line electrode side.

A test sample containing or not containing hCG was mixed with the same volume of the α-galactosidase-HM81 solution prepared in the above step (1) which has been dissolved in a 0.05M phosphate buffer solution (pH 6.0) containing 2.0% bovine serum albumin and 100 mM sodium chloride to a final concentration of 10 units/ml, in order to prepare a solution (A) containing 0 mIU/ml of hCG and 5 U/ml of α-galactosidase-HM81, a solution (B) containing 5 mIU/ml of hCG and 5 U/ml of α-galactosidase-HM81 and a solution (C) containing 50 mIU/ml of hCG and 5 U/ml of α-galactosidase-HM81.

A 45 μl portion of each of the thus prepared solutions (A), (B) and (C) was spotted on the sample-introducing means of the specific binding assay device to allow the sample to permeate into the matrix, and changes with time in the coulomb value were measured to determine coulomb values during one minute after the sample spotting.

The measurement was repeated three times for each of the solutions (A), (B) and (C).

(7) Results

The results are shown in Table 4 as mean values of three repetitions. As is evident from the table, the distribution of the enzyme-labeled antibody HM81 in the matrix (b) changes in response to the concentration of hCG in the test sample, and changes in such a distribution can be measured as changes in the coulomb value at the detection means (c), thus confirming that quantitative determination of hCG concentration in a test sample can be carried out easily and quickly by the use of the assay device of the present invention.

Similar results were obtained when the same type of assay device was constructed and used in the hCG measurement, except that a PBS buffer containing 2.0 mg/ml or 5.0 mg/ml of HM21 was used instead of 0.5 mg/ml when the matrix was prepared (data not shown).

TABLE 4

Relationship between hCG concentrations in test samples and coulomb values measured

| Concentration of hCG in test sample (m IU/ml) | Coulomb values during one minute after sample spotting (μC) |
|---|---|
| 0 | 170 |
| 10 | 133 |
| 100 | 103 |

EXAMPLE 2

A matrix of the specific binding assay device was prepared, and a test sample and a signal substance generator (labeled antibody) were introduced into the sample-introducing means to examine changes in the distribution of the labeled antibody in the matrix.

(1) Preparation of a matrix having a sample-introducing means

A matrix (a part) having a sample-introducing means was prepared in the same manner as in Example 1 (4). Next, a piece of the anti-hCGα antibody-immobilized porous nylon film prepared in Example 1 (3) (a film section impregnated with PBS solution containing 0.5 mg/ml of HM21) was dried and superposed on a polyvinyl chloride plate (30 mm in length, 15 mm in width and 0.5 mm in thickness). The thus superposed nylon film was impregnated with 10 μl of the hot agarose solution, and the resulting nylon film was dried. The matrix (a part) prepared above was superposed on the thus dried nylon film and adhered with pressure. By drying the resulting laminate in a desiccator under reduced pressure, a laminated body composed of a matrix (b), a sample-introducing means (a) and a support (e) was obtained. This device is similar to the type shown in FIG. 11 in which permeation direction 22 of a liquid test sample is indicated by an arrow.

(2) Measurement

A test sample containing or not containing hCG was mixed with the same volume of the α-galactosidase-HM81 solution prepared in Example 1 (1) which has been dissolved in a 0.05M phosphate buffer solution (pH 6.0) containing 2.0% bovine serum albumin and 100 mM sodium chloride to a final concentration of 10 units/ml, in order to prepare a solution (D) containing 0 mIU/ml of hCG and 5 U/ml of α-galactosidase-HM81, a solution (E) containing 10 mIU/ml of hCG and 5 U/ml of α-galactosidase-HM81 and a solution (F) containing 100 mIU/ml of hCG and 5 U/ml of α-galactosidase-HM81.

A 45 μl portion of each of the thus prepared solutions (D), (E) and (F) was spotted on the sample-introducing means of the specific binding assay device prepared in the above step (1).

Next, the filter paper and the anti-hCGα antibody-immobilized porous nylon film, both as composing elements of the matrix, were separated from each other in respective sections, and the amount of the α-galactosidase-HM81 (labeled antibody) in each section was measured by determining α-galactosidase activity using a coloring substrate solution for α-galactosidase (10 mM p-nitrophenyl-α-D-galactopyranoside, Sigma Chemical Co.).

(3) Results

The amount of the α-galactosidase-HM81 in each section thus measured was rearranged as an α-galactosidase-HM81 (α-galactosidase activity) distribution in the matrix, with the results shown in FIG. 12. In the figure, the α-galactosidase activity in each section (layer) containing 0, 10 or 100 mIU/ml of hCG was expressed by percentage based on the activity in the 0 mIU/ml section as 100%.

As is evident from FIG. 12, the distribution of the labeled antibody becomes frequent in the upper layers (first and second layers) and infrequent in the lower layers (third to sixth layers) as the amount of the substance to be assayed (hCG) in the test sample increases from 0 mIU/ml to 100 mIU/ml.

In FIG. 12, the increasing ratio of the amount of the labeled antibody in the upper layers caused by the substance to be assayed in the test sample is small in appearance in comparison with the decreasing ratio in the lower layers. The reason for this is that the distribution of the labeled antibody in the matrix when the amount of the substance to be assayed (hCG) in the test sample was 0 mIU/ml (basic distribution value) itself had a decreasing tendency from the upper layer side toward the lower layer side.

In consequence, it seemed that the signals measured by the procedure of Example 1 (shown by coulomb values) were mainly those signals related to the labeled antibody (signal substance generator) distributed in the lower layers, and changes in the distribution of the labeled antibody in the matrix by the substance to be assayed in the test sample were taking part in the modulation of signals.

The following illustratively describes an assay device for the specific binding assay process of the present invention to measure the distribution of a label (an enzyme) in the matrix.

EXAMPLE 3

Using a laminate of a porous material having an α-galactosidase-immobilized layer, changes in the current values in response to the distance between a carbon electrode and an enzyme layer were measured, in order to examine effects of the positional relation between the detection means and a label (α-galactosidase) on the current values.

(1) Preparation of α-galactosidase-immobilized porous nylon film and rabbit normal serum-immobilized nylon film A 5×8 mm section of a porous nylon film having a pore size of 3.0 μm (immunodyne BIAO30HC5, Pall Process Filtration, Inc.) was impregnated with 5 μl of a PBS solution containing 400 U/ml of α-galactosidase (Seikagaku Kogyo Co., Ltd.) or with 5 μl of normal rabbit serum (to be referred to as "NRS" hereinafter) (available from Japan Biomaterial Center). After 1 hour of reaction at room temperature, the thus treated sections were shaken for 15 hours in a 0.1% bovine serum albumin (BSA)/PBS solution at 4° C. to effect blocking. Thereafter, the thus treated sections were put in a 0.1% Tween 20/PBS solution and shaken for 2 hours at 4° C. to wash them. By repeating the washing step five times or more, α-galactosidase-immobilized nylon films and NRS-immobilized nylon films were obtained.

(2) Preparation of a laminate of porous material having α-galactosidase-immobilized layer One α-galactosidase-immobilized nylon film and five NRS-immobilized nylon films were put on a filter paper to remove moisture, and the resulting films were superposed on a slide glass to prepare a laminate. In this instance, 6 different laminates were prepared in which a single layer of the α-galactosidase-immobilized nylon film was used as the first (uppermost) layer, the second layer, the third layer, the fourth layer, the fifth layer or the sixth (the bottom) layer, in addition to a laminate solely consisting of six NRS-immobilized nylon films. On the uppermost layer of each of the thus prepared laminates was superposed a 4×6 mm section of a filter paper (No. 165, Whatman Corp.) which was subsequently impregnated with 40 μl of a PBS solution containing 0.25% agarose and 0.01% Tween 20 (hot agarose solution) that has been heated in advance to dissolve agarose and kept at 50° C. Thereafter, moisture in the upside portion was removed with a filter paper, and the laminated layers were adhered by pressing them with a pressure of 200 g/section and then dried in a desiccator to obtain the laminate of porous material having an α-galactosidase-immobilized layer.

(3) Preparation of substrate layer

A 5×8 mm section of a porous nylon film having a pore size of 3.0 μm (Immunodyne BIAO30HC5, Pall Process Filtration, Inc.) was impregnated with 5 μl of the hot agarose solution containing 100 mM of an enzyme substrate (p-aminophenyl-α-D-galactopyranoside, Sigma Chemical Co.) and then dried to obtain a substrate layer.

(4) Junction of the laminate of porous material having α-galactosidase-immobilized layer with a detection means A single layer of the substrate layer thus obtained was superposed on the detection means (electrode) prepared in Example 1 (2) in such a manner that the substrate layer covered both the carbon line and the silver/silver chloride line. On the thus prepared detection means were superposed the laminate of porous material containing one α-galactosidase-immobilized layer prepared in the above step (2) and an acrylic plate having a hole (3 mm in diameter) for sample-introduction use, in that order. The resulting laminate was used as a laminated device of porous material containing one α-galactosidase-immobilized layer. In this instance, the hole for sample-introduction use was put right over the uppermost filter paper layer of the laminate, and the acrylic plate was arranged in such a manner that it kept a distance of 1,200 μm from the surface of the electrode during measurement.

That is, as shown in FIG. 13, a laminated device of porous material was constructed which consisted of an acrylic plate 22 having a sample-introducing hole 21, a zero layer as a filter paper part for sample-spotting (introducing) use 30, first to sixth layers of porous nylon film sections, a seventh layer as a substrate layer and a detection means, arranged in that order in the permeation direction 20 of a liquid test sample.

(5) Measurement of electric current using the laminated device of porous material having α-galactosidase-immobilized layer The device constructed in the above step (4) was connected with necessary measuring equipment such as a potentiostat and the like as described in Example 1 (6), using the carbon line side as a working electrode and the silver/silver chloride line side as counter/reference electrode. When the measurement was carried out, an electric potential of +400 mV was applied to the carbon line electrode side based on the silver/silver chloride line electrode side. As a reaction buffer, 30 μl of a 5.0 mM phosphate buffer solution (pH 6.0) containing 2% bovine serum albumin and 100 mM sodium chloride was introduced into the assay device to record current values.

(6) Results

Figure 14A:
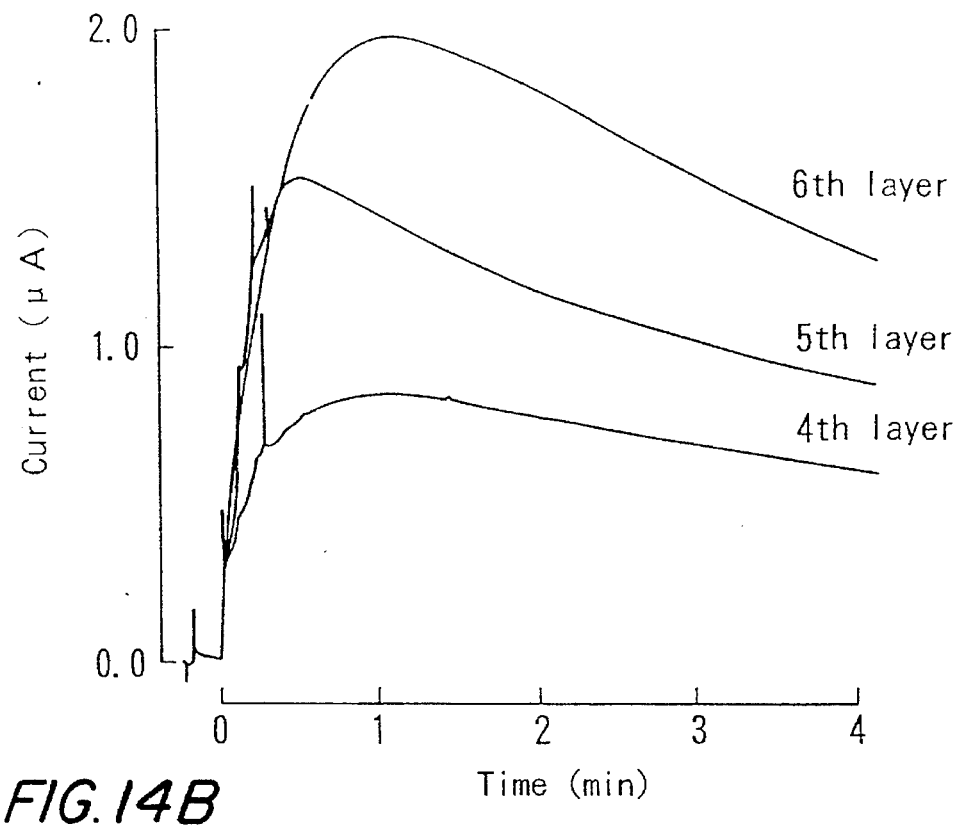
FIGS. 14A and 14B are graphs showing results of the measurement performed in Example 3.
Figure 14B:
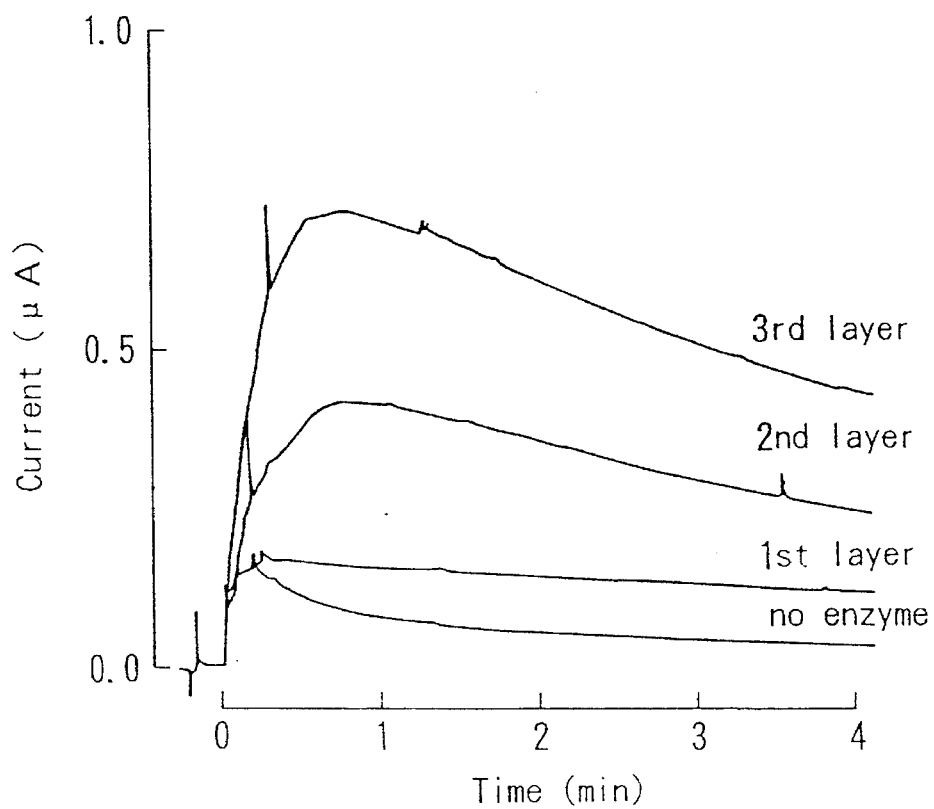

Periodical changes in the electric current when measured using the laminated device of porous material having an α-galactosidase-immobilized layer are shown in FIG. 14 (A) and 14B. The electric current was large when the α-galactosidase-immobilized layer was close to the carbon electrode (detection means), while the current was small when the α-galactosidase-immobilized layer was distant from the detection means. That is, under these experimental conditions, the enzyme molecules can contribute to the electric current when they are located within a distance of at least about 1,000 μm from the detection means, and such a contribution to the electric current gradually becomes large as the enzyme molecules approach the detection means. These results confirm that the present invention can precisely measure the distribution of enzyme molecules in the matrix like he case of Example 1.

EXAMPLE 4

Using a porous material laminate having a horseradish peroxidase (HRPO)-immobilized layer, a glucose oxidase (GOD)-immobilized layer or a HRPO-immobilized and GOD-immobilized layers, changes in the electric current in response to the distance between a carbon electrode and the HRPO-immobilized layer, the GOD-immobilized layer or the HRPO- and GOD-immobilized layers were measured, in order to examine effects of the positional relation between the detection means and a label (GOD) on the electric current.

(1) Preparation of enzyme-immobilized porous membrane

Each of horseradish peroxidase (HRPO, Toyobo Co., Ltd.) and glucose oxidase (GOD, Boehringer Mannheim Corp.) was dissolved in 0.076M phosphate-buffered saline (PBS) to a final concentration of 5 mg/ml. A cellulose nitrate-cellulose acetate mixture membrane having a pore size of 3.0 μm (Cat. No. SSWP 14200, Millipore Corp.) was cut out into a square section having a size of 5×8 mm to be used as an immobilization carrier. Necessary numbers of the thus cut out membrane sections were interposed between two pieces of quantitative filter paper having a diameter of 90 mm (5A, Advantech Toyo Co., Ltd.), and the resulting preparation was further interposed between two acrylic plates. Two sets of such a double-interposed preparation were made. The filter paper portion of each of the thus obtained double-interposed preparations was impregnated with each of the enzyme solution prepared above. After sealing the acrylic plates, the double-interposed preparations were allowed to stand still at 4° C. for at least 24 hours to adhere and fix the enzyme to the membrane sections. The thus treated membrane sections were recovered, washed with PBS, put into a 100 ml capacity beaker containing 60 ml of a 0.1% bovine serum albumin (BSA)/PBS solution and then shaken at 4° C. for at least 1 day to effect blocking. Thereafter, the thus treated sections were put in a 0.1% Tween 20/PBS solution and shaken at 4° C. to wash them. By repeating the washing step four times or more, HRPO-immobilized membrane sections and GOD-immobilized membrane sections were obtained.

(2) Preparation of a porous material laminate having a HRPO-immobilized layer A laminate was prepared which consisted of one dried piece of the HRPO-immobilized membrane section prepared in the above step (1) and five pieces (5×8 mm for each) of No. 54 filter paper (Whatman Corp.). In this instance, a total of 5 different laminates were prepared in which a single layer of the HRPO-immobilized layer was used as the first (uppermost) layer, the second layer, the third layer, the fourth layer or the fifth (the bottom) layer. Each of the thus obtained laminates was superposed on the detection means (electrode) prepared in Example 1 (2) in such a manner that the substrate layer covered both the carbon line and the silver/silver chloride line. On the thus prepared detection means were superposed an acrylic plate 22 having a sample-introducing hole 21 (3 mm in diameter). The resulting laminate was used as a laminated device of porous material having a HRPO-immobilized layer. In this instance, the sample-introducing hole was put right over the uppermost filter paper layer of the laminate, and the acrylic plate 22 was arranged in such a manner that it kept a distance of 1,200 μm from the surface of the electrode during measurement.

Figure 15:
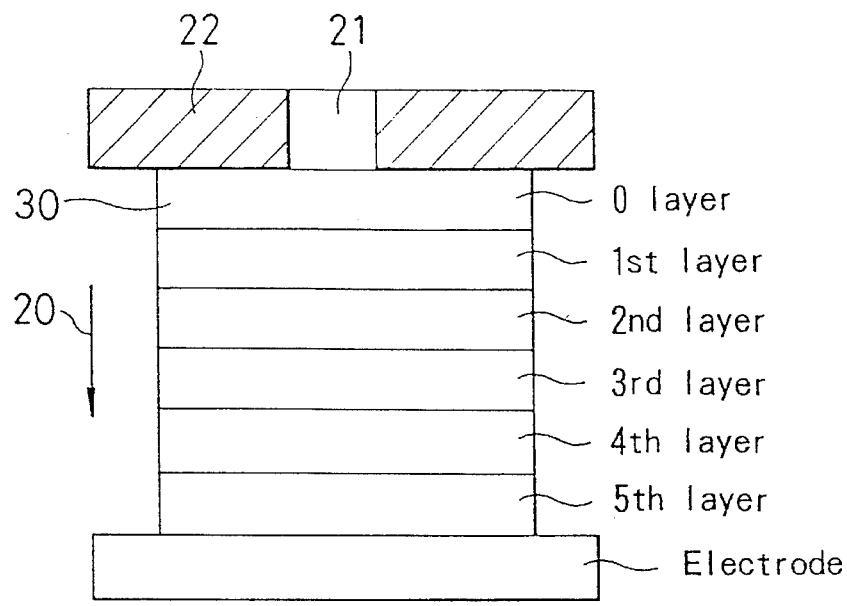
FIG. 15 is a schematic illustration showing an assay device prepared in Example 4 (2).

That is, as shown in FIG. 15, a laminated device of porous material was constructed which consisted of an acrylic plate 22 having a sample-introducing hole 21, a zero layer as a filter paper part for sample-spotting (introducing) use 30, first to fifth layers and an electrode portion as the detection means, arranged in that order in the permeation direction 20 of a liquid test sample.

(3) Measurement of electric current using the laminated device of porous material having a HRPO-immobilized layer The device constructed in the above step (2) was connected with necessary measuring equipment such as a potentiostat and the like as described in Example 1 (6), using the carbon line side as a working electrode and the silver/silver chloride line side as counter/reference electrode. Separately from this, the following aqueous solutions were prepared.

Figure 16:
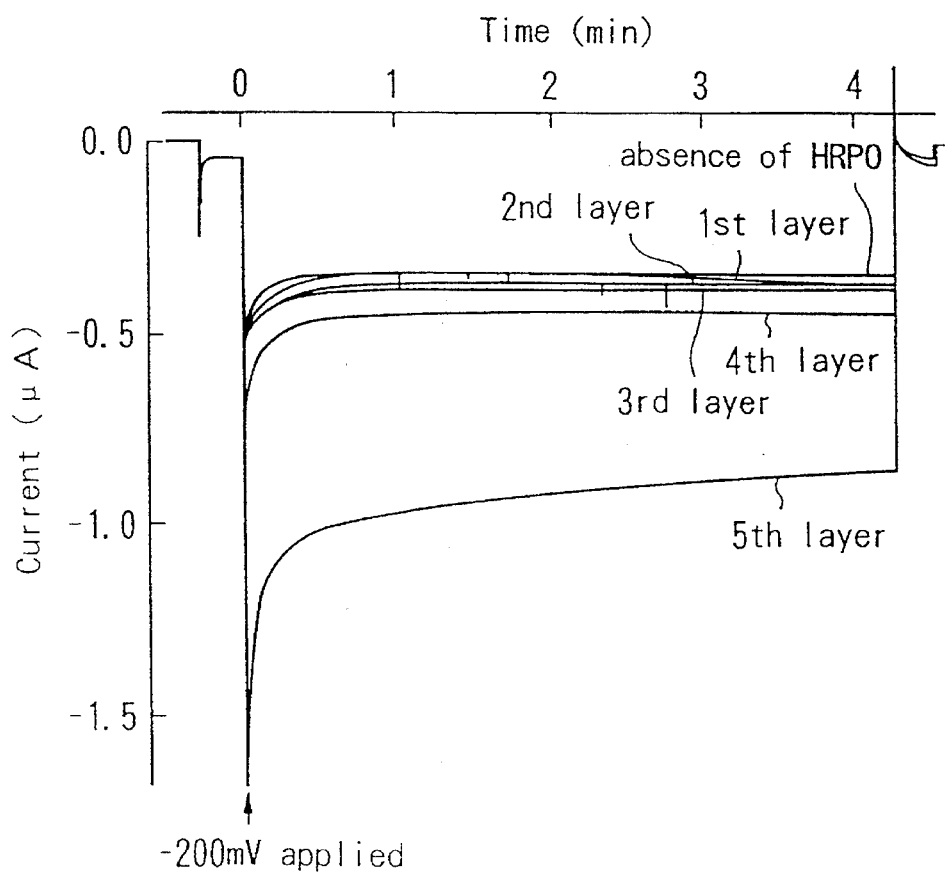
FIG. 16 is a graph showing results of the measurement performed in Example 4 (3).

(1) Hydroquinone aqueous solution (HQ solution) 100 mM hydroquinone (Wako Pure Chemical Industries) 50 mM phosphate buffer (pH 6.0) 100 mM sodium chloride 2) Hydrogen peroxide solution 3.4% hydrogen peroxide 50 mM phosphate buffer (pH 6.0) 100 mM sodium chloride 3) Electrolyte solution 50 mM phosphate buffer (pH 6.0) 100 mM sodium chloride Just before the measurement, 10 μl of the HQ solution, 40 μl of the hydrogen peroxide solution and 950 μl of the electrolyte solution were mixed thoroughly to obtain a mixture solution containing 1 mM of hydroquinone and about 40 mM of hydrogen peroxide as final concentrations. A 40 μl portion of the thus prepared mixture solution was introduced into the assay device through the sample-introducing hole of the acrylic plate. When the resting potential of the working electrode became stable (one minute after the sample-introduction), an electric potential of −200 mV was applied to the working electrode based on the counter/reference electrode to record the electric current. The results are shown in FIG. 16.

(4) Preparation of a porous material laminate having a GOD-immobilized layer A laminate was prepared which consisted of one dried piece of the GOD-immobilized membrane section prepared in the above step (1) and five pieces (5×8 mm for each) of No. 54 filter paper (Whatman Corp.). In this instance, a total of 5 different laminates were prepared in which a single layer of the GOD-immobilized layer was used as the first (uppermost) layer, the second layer, the third layer, the fourth layer or the fifth (the bottom) layer. Each of the thus obtained laminates was superposed on the detection means (electrode) prepared in Example 1 (2) in such a manner that the substrate layer covered both the carbon line and the silver/silver chloride line. On the thus prepared detection means were superposed an acrylic plate having a sample-introducing hole (3 mm in diameter). The resulting laminate was used as a laminated device of porous material having a GOD-immobilized layer. In tills instance, the sample-introducing hole was put right over the uppermost filter paper layer of the laminate, and the acrylic plate was arranged in such a manner that it kept a distance of 1,200 μm from the surface of the electrode during measurement.

Figure 17:
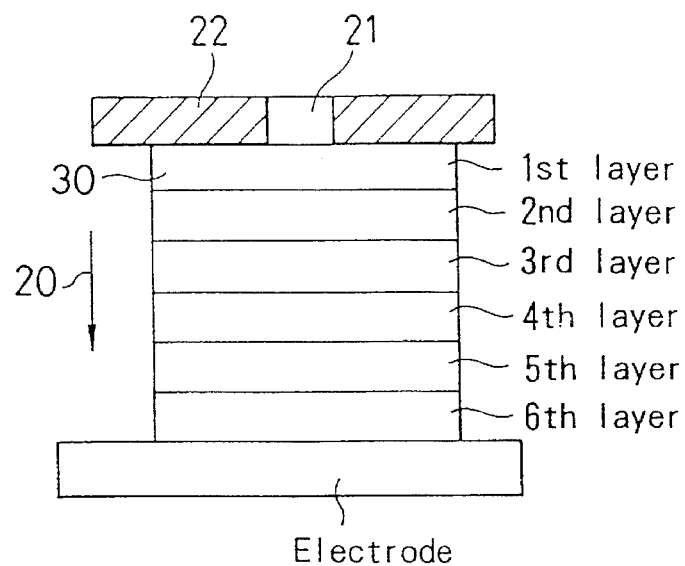
FIG. 17 is a schematic illustration showing an assay device prepared in Example 4 (4).

That is, as shown in FIG. 17, a laminated device of porous material was constructed which consisted of an acrylic plate 22 having a sample-introducing hole 21, first layer as a filter paper part for sample-spotting (introducing) use 30, second to sixth layers as a matrix and an electrode portion as the detection means, arranged in that order in the permeation direction 20 of a liquid test sample.

(5) Measurement of electric current using the laminated device of porous material having a GOD-immobilized layer The device constructed in the above step (4) was connected with necessary measuring equipment such as a potentiostat and the like as described in Example 1 (6), using the carbon line side as a working electrode and the silver/silver chloride line side as counter/reference electrode. Separately from this, the following aqueous solutions were prepared. In this instance, the glucose solution was stored in a refrigerator for at least 48 hours prior to its use.

Figure 18:
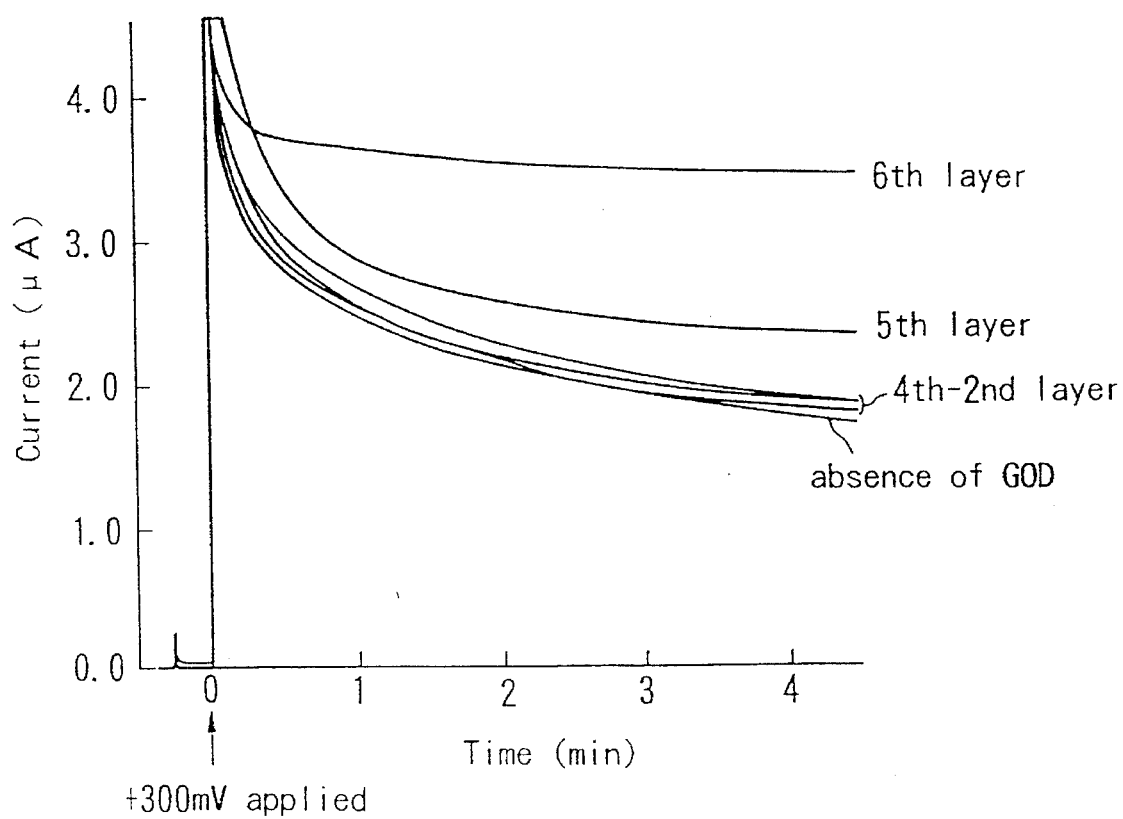
FIG. 18 is a graph showing results of the measurement performed in Example 4 (5).

(1) Hydroquinone aqueous solution (HQ solution) 5 mM hydroquinone (Wako Pure Chemical Industries) 100 mM phosphate buffer (pH 7.0) 100 mM sodium chloride (2) Glucose solution 1.5M glucose 100 mM phosphate buffer (pH 7.0) 100 mM sodium chloride Just before the measurement, 50 μl of the HQ solution was mixed thoroughly with 50 μl of the glucose solution to obtain a mixture solution containing 2.5 mM of hydroquinone and 0.75M of glucose as final concentrations. A 40 μl portion of the thus prepared mixture solution was introduced into the assay device through the sample-introducing hole of the acrylic plate. When the resting potential of the working electrode became stable (one minute after the sample-introduction), an electric potential of +300 mV was applied to the working electrode based on the counter/reference electrode to record the electric current. The results are shown in FIG. 18.

(6) Preparation of a porous material laminate having HRPO-immobilized and GOD-immobilized layers A seven layer laminate was prepared which consisted of one dried piece of the HRPO-immobilized membrane section and one dried piece of the GOD-immobilized membrane section, both prepared in the above step (1), and five pieces (5×8 mm for each) of No. 54 filter paper (Whatman Corp.). In this instance, a total of 5 different laminates were prepared in which a single layer of the HRPO-immobilized layer was always used as the bottom layer and a single layer of the GOD-immobilized layer was used as the first (uppermost) layer, the second layer, the third layer, the fourth layer or the fifth layer. Each of the thus obtained laminates was superposed on the detection means (electrode) prepared in Example 1 (2) in such a manner that the substrate layer covered both the carbon line and the silver/silver chloride line. On the thus prepared detection means were superposed an acrylic plate having a sample-introducing hole (3 mm in diameter). The resulting laminate was used as a laminated device of porous material having a HRPO-immobilized layer and a GOD-immobilized layer. In this instance, the sample-introducing hole was put right over the uppermost filter paper layer of the laminate, and the acrylic plate was arranged in such a manner that it kept a distance of 1,200 μm from the surface of the electrode during measurement.

Figure 19:
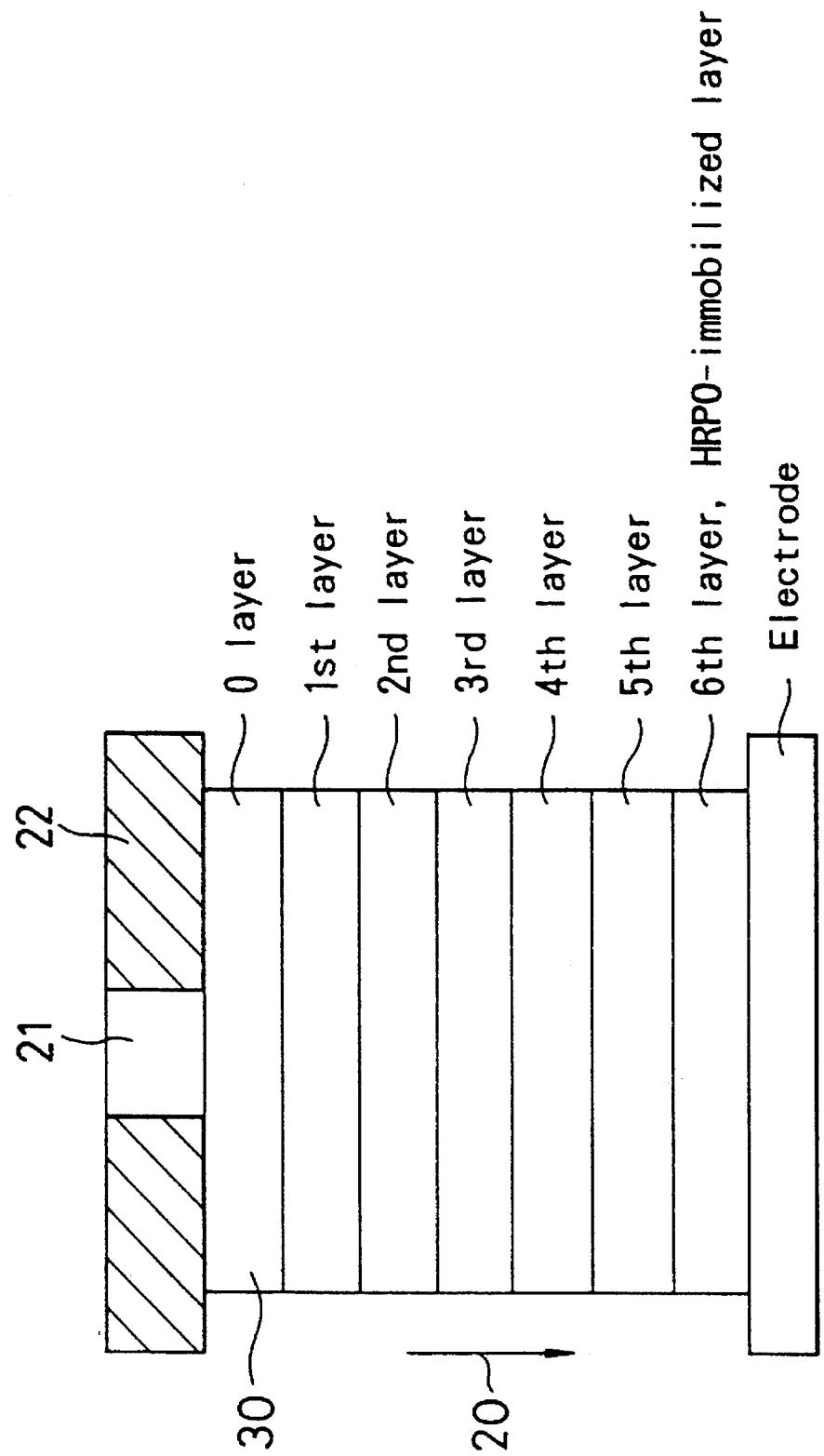
FIG. 19 is a schematic illustration showing an assay device prepared in Example 4 (6).

That is, as shown in FIG. 19, a laminated device of porous material was constructed which consisted of an acrylic plane 22 having a sample-introducing hole 21, a zero layer as a filter paper part for sample-spotting (introducing) use 30, first to fifth layers, a sixth layer as a HRPO-immobilized layer and an electrode portion as the detection means, arranged in that order in the permeation direction 20 of a liquid test sample.

(7) Measurement of electric current using the laminated device of porous material having a HRPO-immobilized layer and a GOD-immobilized layer The device constructed in the above step (6) was connected with necessary measuring equipment such as a potentiostat and the like as described in Example 1 (6), using the carbon line side as a working electrode and the silver/silver chloride line side as counter/reference electrode. Separately from this, the following aqueous solutions were prepared. In this instance, the glucose solution was stored in a refrigerator for at least 48 hours prior to its use.

Figure 20:
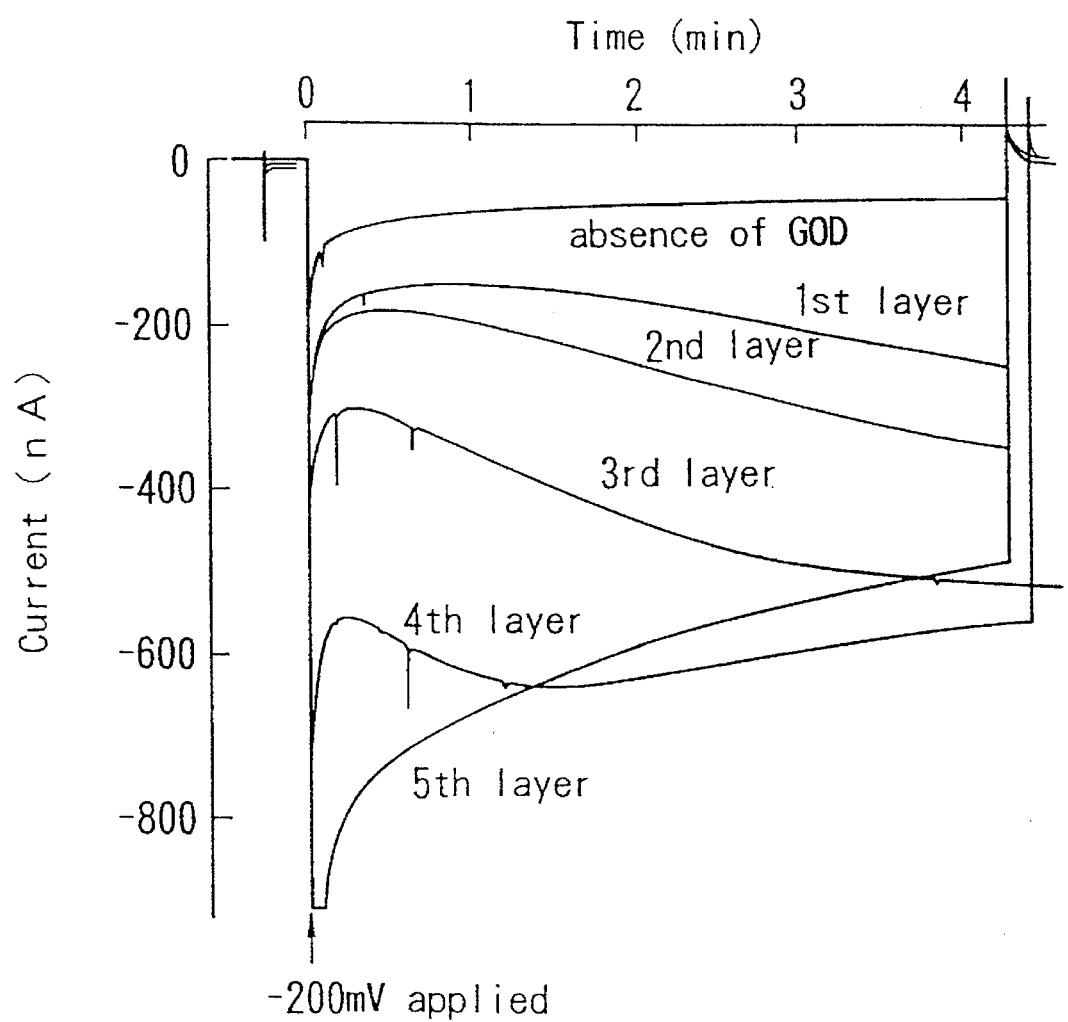
FIG. 20 is a schematic illustration showing an assay device prepared in Example 4 (7).

(1) Hydroquinone aqueous solution (HQ solution) 10 mM hydroquinone (Wako Pure Chemical Industries) 100 mM phosphate buffer (pH 7.0) 100 mM sodium chloride (2) Glucose solution 1.5M glucose 100 mM phosphate buffer (pH 7.0) 100 mM sodium chloride (3) Electrolyte solution 100 mM phosphate buffer (pH 7.0) 100 mM sodium chloride Just before the measurement, 45 μl of the HQ solution, 300 μl of the glucose solution and 555 μl of the electrolyte solution were mixed thoroughly to obtain a mixture solution containing 0.5 mM of hydroquinone and 0.5M of glucose as final concentrations. A 40 μl portion of the thus prepared mixture solution was introduced into the assay device through the sample-introducing hole of the acrylic plate. When the resting potential of the working electrode became stable (one minute after the sample-introduction), an electric potential of −200 mV was applied to the working electrode based on the counter/reference electrode to record the electric current. The results are shown in FIG. 20.

(8) Results

FIG. 16 shows periodical changes in the electric current when measured using the laminated device of porous material having a HRPO-immobilized layer constructed in the above step (3). The electric current was large when the HRPO-immobilized layer was close to the carbon electrode (detection means), while the current was small when the HRPO-immobilized layer was distant from the detection means. FIG. 18 shows periodical changes in the electric current when measured using the laminated device of porous material having GOD-immobilized layer constructed in the above step (5). The electric current was large when the GOD-immobilized layer was close to the carbon electrode (detection means), while the current was small when the GOD-immobilized layer was distant from the detection means.

In both of these cases, the contribution of the enzyme layer to the electric current decreased rapidly as the distance between the enzyme layer and the electrode (detection means) becomes large, and such a contribution of the enzyme layer to the electric current was almost negligible when the enzyme layer was two layers or more distant from the electrode (detection means). It was assumed that a cycling mechanism of a signal substance (probably hydroquinone/benzoquinone pair) between the enzyme and the electrode was taking place under these experimental conditions. On the basis of these results, it was confirmed that the enzyme molecules can contribute to the electric current mostly when they are located within a distance of at least about 500 μm from the detection means, and such a contribution to the electric current rapidly becomes large as the enzyme molecules approach the detection means. These results also confirm that the present invention can precisely measure the distribution of enzyme molecules in a thin layer having a thickness of several hundred μm.

FIG. 20 shows periodical changes in the electric current when measured using the laminated device of porous material having HRPO-immobilized and GOD-immobilized layers constructed in the above step (5). The electric current was large when the GOD-immobilized layer was close to the HRPO layer-covered carbon electrode (detection means), while the current was small when the GOD-immobilized layer was distant from the detection means. In contrast to the above two cases, the contribution of the enzyme (GOD) layer to the electric current decreased relatively gradually as the distance between the enzyme layer and the HRPO layer-covered electrode (detection means) becomes large, and such a contribution of the enzyme layer to the electric current was not negligible even when the enzyme layer was five layers or more distant from the electrode (detection means). It was confirmed that, similar to the case of Example 3, signals at the detection means are modulated by a relatively broad range of label distribution when participation of a signal substance-cycling mechanism is small or negligible. That is, it was confirmed that the enzyme molecules can contribute to the electric current when they are located within a distance of at least about 1,000 μm from the detection means, and such a contribution to the electric current gradually becomes large as the enzyme molecules approach the detection means. Such a contribution mode of the enzyme confirms that the present invention can precisely measure the distribution of enzyme molecules even in a relatively thick matrix. On the basis of these results, it was confirmed that the distribution of a label (an enzyme for example) in a matrix adjacent to a detection means can be effected precisely, easily and quickly with broad applicability by the use of the assay process of the present invention.

As another example of the specific binding assay process and device of the present invention, the following describes an assay process in which hCG is used as a substance to be assayed, glucose oxidase is used as a composing element (labeling agent) of a label (signal substance generator) and signal detection is effected by the measurement of electric current, as well as an assay device for use in the process.

Similar to the case of Example 1, the anti-hCG antibody HM21 was used as immobilized antibody in the matrix (b), and the anti-hCG antibody HM81 was used as a composing element of the signal substance generator. That is, glucose oxidase-labeled HM81 antibody was used as a label (signal substance generator). With regard to the matrix (b), a single layer of a rectangular section of a porous nylon film carrier to which the HM21 antibody has been adhered and immobilized was used in a horizontal direction.

EXAMPLE 5

A specific binding assay device was constructed and hCG concentrations in test samples were measured using the device.

(1) Preparation of a conjugate of anti-hCGβ antibody and glucose oxidase (labeled antibody)

Mouse monoclonal antibody HM81 (Mochida Pharmaceutical Co., Ltd.) which recognizes the β chain of hCG was dissolved in a buffer solution consisting of 100 mM sodium chloride, 1 mM EDTA and 60 mM triethanolamine (pH 8.0, TEA buffer) to a final concentration of 3.9 mg/ml, and the resulting solution was dialyzed thoroughly against the TEA buffer which has been purged with nitrogen gas. A 55 µl portion of 50 mM 2-iminothiolane hydrochloride (Pierce Chemical Company) solution was added to 1.0 ml of the thus prepared antibody solution, and the mixture was stirred and then allowed to stand still for 1.5 hours at 4° C. in an atmosphere of nitrogen. Thereafter, the resulting solution was dialyzed thoroughly against a buffer solution consisting of 100 mM sodium chloride, 1 mM EDTA and 100 mM phosphate (pH 7.0, EDTA-PB) which has been purged with nitrogen gas. In this way, SH group-introduced anti-hCGβ antibody HM81 was obtained.

Glucose oxidase (GOD, Boehringer Mannheim Corp.) was dissolved in 1.43 ml of 100 mM phosphate buffer (pH 7.0) to a final concentration of 70 µM, and the resulting solution was mixed with 20 µl of 50 mM sulfo-SMCC (Pierce Chemical Company) while the solution was gently stirred at 30° C. After 45 minutes of reaction at 30° C., the resulting reaction mixture was dialyzed thoroughly against EDTA-PB which has been purged with nitrogen gas to obtain maleimidated GOD.

A 1.5 mole portion of the SH group-introduced HM81 antibody was mixed with 1 mole of the maleimidated GOD, and the mixture was incubated at 4° C. for 20 hours in an atmosphere of nitrogen gas. After the reaction, 50 µl of 50 mM cysteamine solution was added to the reaction mixture, and the reaction was continued at 4° C. for 30 minutes in an atmosphere of nitrogen gas. Thereafter, the resulting reaction mixture was subjected to gel filtration chromatography using a Sephacryl 300HR (Pharmacia K.K.) column which has been equilibrated with EDTA-PB purged with nitrogen.

Each of the thus eluted fractions was checked for its absorbances at 280 nm and 452 nm and for its GOD activity in accordance with the procedure disclosed in *"Biochemical Information"* by Boehringer Mannheim Corp., in order to collect and concentrate fractions containing the HM81/GOD linked product but not containing free enzyme molecules. The thus concentrated preparation of the linked product (to be referred to as "GOD-HM81" hereinafter) was checked for its molecular weight by a Phast system electrophoresis (Pharmacia K.K.) and used as a signal substance generator in measuring experiments.

(2) Preparation of anti-hCGα antibody-immobilized porous nylon film

Mouse monoclonal antibody HM21 (Mochida Pharmaceutical Co., Ltd.) which recognizes the α chain of hCG was dissolved in a 0.1M sodium bicarbonate aqueous solution (pH 8.3) to a final concentration of 1.0 mg/ml. A 4×15 mm section of a porous nylon film having a pore size of 3.0 µm (Immunodyne BIAO30HC5, Pall Process Filtration, Inc.) was impregnated with 8 µl of the thus prepared antibody solution. After 1 hour of reaction at room temperature, the thus treated section was put in a 100 ml capacity beaker containing 60 ml of a 0.1% bovine serum albumin (BSA)/PBS solution and shaken for 2 days at 4° C. to effect blocking. Thereafter, the resulting nylon film section was washed by shaking it in a 1% Tween 20/PBS solution at 4° C. By repeating the washing step 4 times or more, an anti-hCGα antibody (HM21)-immobilized porous nylon film was obtained.

Figure 21:
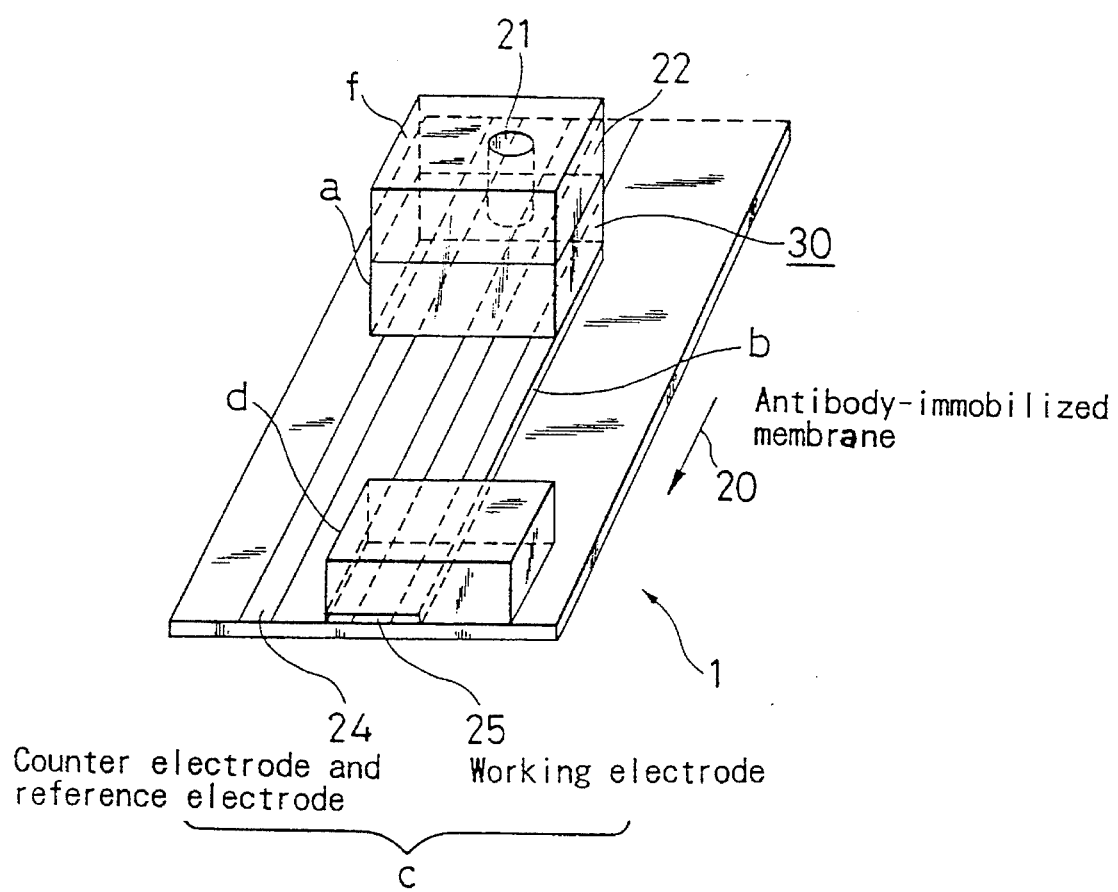
FIG. 21 is a perspective diagram showing an assay device prepared in Example 5 (3).

(3) Construction of a specific binding assay device having a sample-introducing means and a water-absorbing means, by arranging a single layer of anti-hCGα antibody-immobilized porous nylon film section on an electrode As shown in FIG. 21, the working electrode 23 and the counter/reference electrode 24 prepared in Example 1 (2) were used as the detection means (c) (electrode). A single sheet of the dried HM21 antibody-immobilized porous nylon film as the specific binding matrix (b) was arranged on the detection means (c) (electrode) in such a manner that the direction of the carbon line of the working electrode 23 coincided with the longitudinal direction of the nylon film and that the nylon film covered a part of the carbon line. Four layers of 5×8 mm sections of Whatman filter paper No. 54 were superposed on each side of the resulting nylon film in such a manner that the 8 mm direction became vertical to the electrode lines. In this instance, the filter paper sections laminated on the closer side to the terminal of the electrode were arranged in such a manner that the filter paper laminate covered both the silver/silver chloride line and the carbon line, and the thus arranged laminate was used as the sample-introducing means (a). The other filter paper sections laminated on the distant side from the terminal of the electrode were arranged in such a manner that the filter paper laminate covered not the silver/silver chloride line but the carbon line, and the thus arranged laminate was used as the absorption means (d). Thereafter, an acrylic plate 22 having a sample-introducing hole 21 (3 mm in diameter) was superposed on the sample-introducing means (a) to complete a specific binding assay device for use in the measurement of hCG concentration. In this instance, the hole 21 for sample-introduction use was put right over the uppermost filter paper layer of the sample-introducing means (a), and the acrylic plate 22 was arranged in such a manner that it kept a distance of 1,200 µm from the surface of the electrode during measurement. This device is close to the type shown in FIG. 9 (E).

(4) Measurement

The device constructed in the above step (3) was connected with necessary measuring equipment such as a potentiostat and the like as described in Example 1 (6), using the carbon line side as a working electrode and the silver/silver chloride line side as counter/reference electrode.

Each of three test samples containing different amounts of hCG was mixed with the same volume of a GOD-HM81 solution which has been adjusted to an antibody-based concentration of 7.5 µg/ml using a 100 mM sodium chloride/0.1M phosphate buffer (pH 7.0) supplemented with 0.1% BSA (to be referred to as "PB for reaction use" hereinafter). A 55 µl portion of the thus prepared mixture solution was mixed thoroughly with 55 µl of a 400 µM hydroquinone solution prepared using the 0.1% BSA-containing PB for reaction use and further with 110 µl of a 1.5M glucose solution prepared using the PB for reaction use. In this way, a solution (A) having an hCG concentration of 0 IU/l, a solution (B) having an hCG concentration of 0.31 IU/l and a solution (C) having an hCG concentration of 3.1 IU/l were prepared, each solution containing 0.94 µg/ml of GOD- HM81 in antibody-based concentration, 100 μM of hydroquinone and 0.75M of glucose.

A 55 μl portion of each of the solutions (A), (B) and (C) was spotted on the sample-introducing means through the sample-introducing hole of the acrylic plate of the specific binding assay device. When the the test sample permeated into the matrix and further into the water absorption matrix (3 minutes after the sample spotting), an electric potential of +300 mV was applied to the working electrode based on the counter/reference electrode to record electric current.

(5) Results

Table 5 shows changes in the electric current 2, 4, 6 and 8 minutes after the application of the electric potential to the working electrode. At each time measured, the electric current became high in response to the concentration of hCG. On the basis of these results, it was confirmed that quantitative determination of the concentration of hCG in a test sample can be made easily and quickly by the use of the assay device of the present invention.

TABLE 5

Relationship between the hCG concentration in reaction solution and the electric current measured

| Conc. of hCG in reaction solution | Electric current (nA) after: | | | |
|---|---|---|---|---|
| (IU/l) | 2 min | 4 min | 6 min | 8 min |
| 0.0 | 195 | 170 | 156 | 148 |
| 0.31 | 215 | 190 | 177 | 168 |
| 3.1 | 232 | 204 | 189 | 182 |

As another example of the specific binding assay process and device of the present invention, the following describes an assay process in which hCG is used as a substance to be assayed, glucose oxidase is used as a composing element (labeling agent) of the signal substance generator and signal detection is effected by the measurement of periodical changes in the electric current, as well as an assay device for use in the process.

Similar to the case of Example 1, the anti-hCG antibody HM21 was used as immobilized antibody in the matrix (b), and the anti-hCG antibody HM81 was used as a composing element of the signal substance generator. That is, glucose oxidase-labeled HM81 antibody was used as the signal substance generator. With regard to the matrix (b), square sections cue out from a porous cellulose nitrate/cellulose acetate mixture membrane to which the HM21 antibody has been adhered and immobilized were used by laminating them in the same manner as described in Example 1.

EXAMPLE 6

A specific binding assay device was constructed and hCG concentrations in test samples were measured using the device.

(1) Preparation of anti-hCGα antibody-immobilized porous membrane and HRPO-immobilized porous membrane A cellulose nitrate/cellulose acetate mixture membrane having a pore size of 3.0 μm (Cat. No. SSWP 14200, Millipore Corp.) was cut into square sections (5×8 mm for each), and the thus obtained sections were put in a beaker containing 50 ml of a 0.1% BSA/PBS solution. The sections were shaken for 60 hours at 4° C. and then heated at 60° C. for 30 minutes to immobilize BSA on the membrane sections. Thereafter, the resulting membrane sections were washed by replacing the BSA/PBS solution with PBS and shaking the sections for 1.5 hours or more at 4° C. The washing step was repeated 5 times and the resulting sections were dried. Separately from this, mouse monoclonal antibody HM21 (Mochida Pharmaceutical Co., Ltd.) which recognizes the α chain of hCG was dissolved in PBS to a final concentration of 1.0 mg/ml. Each of the dried membrane sections obtained above was impregnated with 15 μl of the thus prepared antibody solution and then with 15 μl of a 0.1% aqueous solution of glutaraldehyde (GA, Wako Pure Chemical Industries, Ltd.). By drying the thus treated sections, anti-hCGα antibody-immobilized porous membrane sections were obtained. Separately from this, each of the dried membrane sections obtained above was impregnated with 15 μl of a PBS solution containing 5 mg/ml of HRPO (Toyobo Co., Ltd.) and then with 15 μl of a 0.1% aqueous solution of glutaraldehyde (GA, Wako Pure Chemical Industries, Ltd.). By drying the thus treated sections, HRPO-immobilized porous membrane sections were obtained. Each of the thus obtained anti-hCGα antibody-immobilized and HRPO-immobilized porous membrane sections was put in a 100 ml capacity beaker containing 60 ml of a 0.1% bovine serum albumin (BSA)/PBS solution and shaken for at least 15 hours at 4° C. to effect blocking. Thereafter, the resulting sections were washed by shaking them in a 0.1% Tween 20/PBS solution at 4° C. The washing step was repeated 4 times or more.

(2) Construction of a matrix by superposing 9 layers of the anti-hCGα antibody-immobilized porous membrane sections on an electrode which is covered with a layer of the HRPO-immobilized porous membrane A total of 9 layers of the anti-hCGα antibody-immobilized porous membrane were superposed on a single layer of the HRPO-immobilized porous membrane obtained in the above step (1), followed by additional superposition of 2 layers of 5×8 mm cut sections of filter paper (No. 54, Whatman Corp.) on the uppermost layer of the anti-hCGα antibody-immobilized porous membrane to obtain a laminate of 12 layers. The thus obtained laminate was arranged on the detection means (c) (electrode) prepared in Example 1 (2) in such a manner that the laminate covered both the silver/silver chloride line and the carbon line. Thereafter, an acrylic plate having a sample-introducing hole (3 mm in diameter) was superposed on the laminate to complete a specific binding assay device for use in the measurement of hCG concentration. In this instance, the hole for sample-introduction use was put right over the uppermost filter paper layer of the laminate, and the acrylic plate was arranged in such a manner that it kept a distance of 1,800 μm from the surface of the electrode during measurement. This device is close to the type shown in FIG. 9 (A).

(3) Measurement

The specific binding assay device constructed in the above step (2) was connected with necessary measuring equipment such as a potentiostat and the like as described in Example 1 (6), using the carbon line side as a working electrode and the silver/silver chloride line side as counter/reference electrode.

Each of four test samples containing different amounts of hCG was mixed with the same volume of a GOD-HM81 solution which has been adjusted to an antibody-based concentration of 4.0 μg/ml using a 100 mM sodium chloride/ 0.1M phosphate buffer (pH 7.0) supplemented with 0.1% BSA (PB for reaction use). In this way, a solution (A) having an hCG concentration of 0 IU/l, a solution (B) having an hCG concentration of 10 IU/l, a solution (C) having an hCG concentration of 100 IU/l and a solution (D) having an hCG concentration of 1,000 IU/l were prepared, each solution containing 2.0 μg/ml of GOD-HM81 in antibody-based final concentration.

Separately from this, the following hydroquinone-glucose aqueous solution (HQ-glucose solution) was prepared. In this instance, the 100 mM glucose solution was stored in a refrigerator for at least 48 hours prior to its use.

(HQ-glucose solution)

0.5 mM hydroquinone (Wako Pure Chemical Industries)

100 mM glucose 0.1% BSA 100 mM phosphate buffer (pH 7.0)

100 mM sodium chloride

A 50 μl portion of the thus prepared HQ-glucose solution was introduced into the specific binding assay device through the sample-introducing hole of the acrylic plate. When the resting potential of the working electrode became stable (about 2 minutes after the introduction of the HQ-glucose solution), an electric potential of −200 mV was applied to the working electrode based on the counter/ reference electrode to record the electric current. One minute after the setting of the electric potential, a 10 μl portion of each of the solutions (A), (B), (C) and (D) was introduced into the sample-introducing means through the sample-introducing hole of the acrylic plate of the specific binding assay device, and the recording of the electric current was continued to calculate the difference in the electric currents measured after 3 minutes and 9 minutes of the sample introduction.

(4) Results

Changes in the electric current per one minute were calculated from the difference in the electric currents measured after 3 minutes and 9 minutes of the sample introduction, with the results shown in Table 6. As shown in the table, the changing ratio of the electric current became low in response to the concentration of hCG. It seems probable that the frequency of the labeled antibody being trapped in the upper area of the multilayer matrix becomes high with the increase in the hCG concentration as a result of the specific binding reaction, thus causing shifting of the label distribution toward the upper side of the matrix. On the basis of these results, it was confirmed that quantitative determination of the concentration of hCG in a test sample can be made easily and quickly by the use of the assay device of the present invention.

TABLE 6

Relationship between the hCG concentration in reaction solution and the changing ratio of the electric current

| Conc. of hCG in reaction solution (IU/l) | Changing ratio of electric current (nA/min) |
| --- | --- |
| 0 | 7.8 |
| 10 | 7.8 |
| 100 | 6.5 |
| 1,000 | 4.5 |

Next, application of fine particles to a specific binding substance-immobilizing carrier is described as another example of the matrix preparation process of the present invention.

EXAMPLE 7

Bovine serum albumin (BSA)-immobilized fine particles and anti-C reactive protein (CRP) antibody-immobilized fine particles were prepared as examples of antigen immobilization and antibody immobilization, respectively, and a matrix for specific binding reaction use was prepared.

(1) Preparation of BSA-immobilized and anti-CRP antibody-immobilized fine particles A 4.28 g portion of sodium periodate (Wako Pure Chemical Industries, Ltd.) was dissolved in 100 ml of distilled water, and the solution was cooled down to 4° C. A 1.0 g portion of crystalline cellulose having a mean particle size of 6 μm (AVICEL PH-M06, Asahi Chemical Industry Co., Led.) was suspended in the above solution and stirred gently for 16 hours at 4° C. in the dark. The resulting suspension was added to a solution which has been prepared by dissolving 1.5 g of ethylene glycol (Wako Chemical Industries, Ltd.) in 100 ml of distilled water, and the resulting mixture was stirred at 4° C. for 1 hour. Thereafter, the thus treated cellulose particles were recovered on a glass filter by suction filtration, washed at least 8 times with 1 mM acetate buffer (pH 4.4) and when re-suspended in the same buffer to a concentration of 100 mg Avicel/ml.

Each solution of BSA (Seikagaku Kogyo Co., Ltd.) and rabbit anti-human CRP antibody (available from Nippon BioTest Laboratories, Inc.) was thoroughly dialyzed with 1 mM sodium acetate buffer (pH 4.4). Each of the crystalline cellulose treated above and an untreated crystalline cellulose preparation, both suspended in 1 mM acetate buffer (pH 4.4), was subjected to ultrasonic treatment, stirred and then mixed with the BSA solution or the anti-CRP antibody solution to prepare the following suspensions A to L.

| Suspension | Antigen or antibody | Crystalline cellulose |
| --- | --- | --- |
| A | BSA 20 mg/ml | treated 80 mg/ml |
| B | BSA 5 mg/ml | treated 80 mg/ml |
| C | BSA 1 mg/ml | treated 80 mg/ml |
| D | BSA 0.2 mg/ml | treated 80 mg/ml |
| E | BSA 0.0 mg/ml | treated 80 mg/ml |
| F | BSA 20 mg/ml | untreated 80 mg/ml |
| G | BSA 5 mg/ml | untreated 80 mg/ml |
| H | BSA 1 mg/ml | untreated 80 mg/ml |
| I | BSA 0.2 mg/ml | untreated 80 mg/ml |
| J | BSA 0.0 mg/ml | untreated 80 mg/ml |
| K | CRP Ab* 1 mg/ml | treated 80 mg/ml |
| L | CRP Ab* 1 mg/ml | untreated 80 mg/ml |

(CRP Ab*, anti-CRP antibody)

Each of the thus prepared suspensions was shaken at 4° C. for 5 hours and then mixed with 1/20 volume of 0.2M sodium carbonate buffer (pH 9.5). After 1 hour of shaking at 4° C., the thus treated suspension was subjected to centrifugation, and the absorbance (280 nm) of the resulting supernatant fluid was measured to calculate the amount of residual protein. The cellulose particles precipitated by the centrifugation were washed by re-suspending them in PBS and subjecting the suspension to centrifugation. The washing step was repeated at least 5 times. Thereafter, the suspensions A and K were selected as BSA-immobilized fine particles and anti-CRP antibody-immobilized fine particles, respectively, and each of the two preparations was made into a 50% crystalline cellulose/10% gelatin/PBS suspension.

(2) Results

The difference between the amount of the initially added BSA or anti-CRP antibody and the amount of the residual protein in the supernatant fluid measured in the above step (1) was used as the amount of protein bound to the crystalline cellulose. Table 7 shows the actual amount of bound protein which is expressed as the difference between the amount of protein bound to the treated crystalline cellulose and the amount of protein bound to the untreated crystalline cellulose.

TABLE 7

Amount of protein bound to crystalline cellulose

| | Protein conc. at the time of binding reaction (mg/ml) | Amount of bound protein (µg protein/mg crystalline cellulose) |
|---|---|---|
| BSA | 20 | 19 |
| BSA | 5 | 13 |
| BSA | 1 | 8.4 |
| BSA | 0.2 | 2.5 |
| BSA | 0.0 | 0.0 |
| Anti-CRP antibody | 1 | 9.2 |

(3) Preparation of a matrix for specific binding reaction use, making use of the BSA-immobilized fine particles A 0.8 µl portion of the BSA-immobilized fine particle suspension having a composition of ultrasonic-treated 50% crystalline cellulose/10% gelatin/PBS was mixed thoroughly with 0.2 ml of 10% glycerol aqueous solution. The thus prepared mixture was poured in a mold arranged on a horizontally placed electrode base and dried in a desiccator to obtain a matrix for use in the specific binding reaction.

EXAMPLE 8

As another example of the specific binding assay process and device of the present invention, the following describes an assay process in which hCG is used as a substance to be assayed, horseradish peroxidase is used as a composing element (labeling agent) of the signal substance generator and signal detection is effected by the measurement of electric current, as well as an assay device for use in the process.

Similar to the case of Example 1, the anti-hCG antibody HM21 was used as immobilized antibody in the matrix (b), and the anti-hCG antibody HM81 was used as a component of the signal substance generator. That is, horseradish peroxidase-labeled HM81 antibody was used as the signal substance generator. With regard to the matrix (b), a single layer of a circular section of a porous membrane carrier to which the HM21 antibody has been bound and immobilized was used.

A specific binding assay device was constructed and hCG concentrations in test samples were measured using the device.

Figure 22:
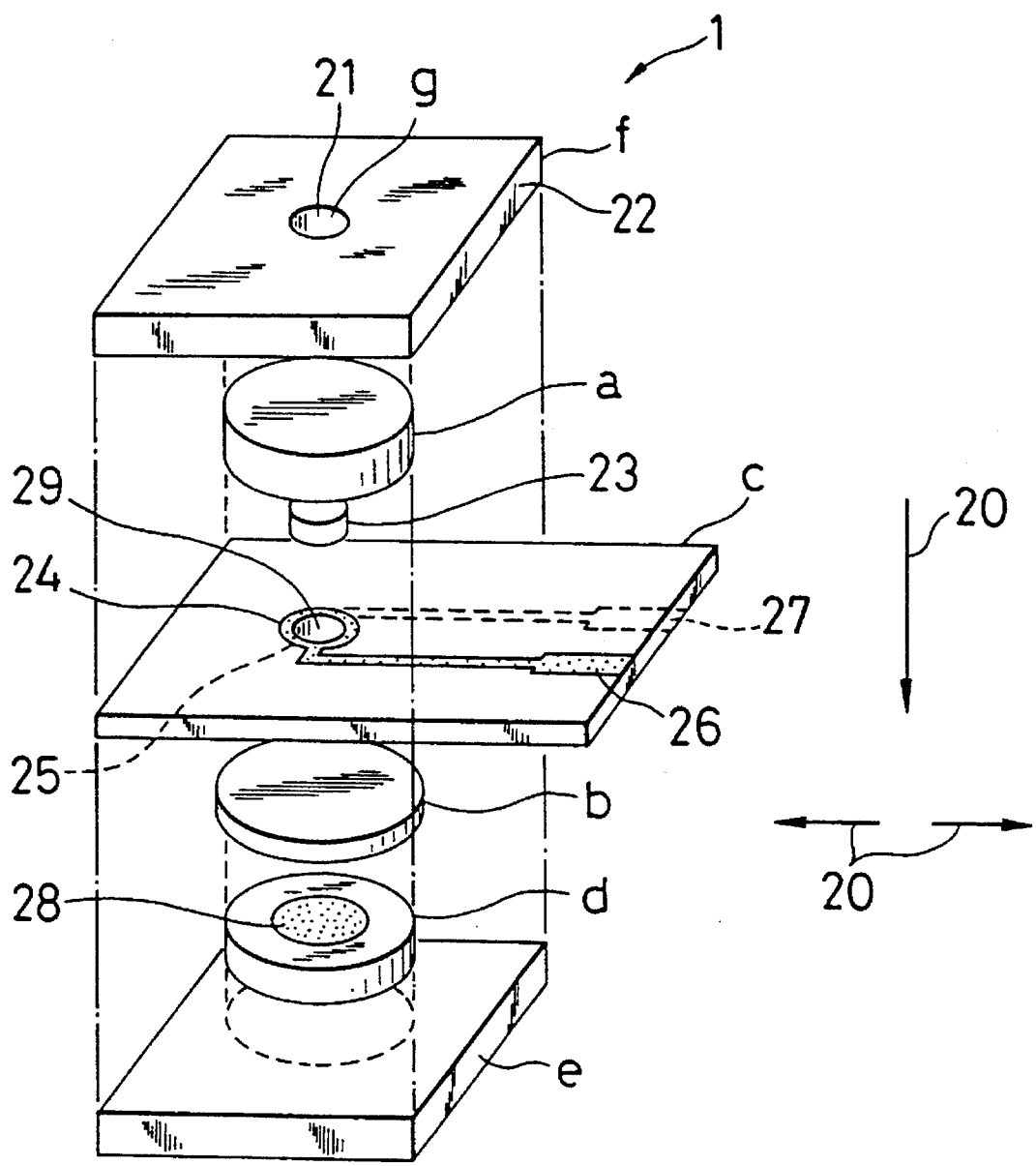
FIG. 22 is an assembly diagram showing an assay device prepared in Example 8.

FIG. 22 shows an assembly diagram of %he specific binding assay device 1 used in this example. In this device, as indicated with arrows, the permeation direction of a liquid test sample is vertical in the sample-introducing means (a), but becomes horizontal on the matrix (b) because of the liquid-impermeable sealing means 28 arranged on the surface of the absorption means (d). In addition, electrode parts to be used as the detection means (c) are arranged on the periphery of the upper and lower surfaces of the communication means 23 as a counter/reference electrode and a working electrode, respectively. Because of this, distribution of a specific binding reaction can be measured in the radial direction in the matrix (b) which is arranged under the communication means 23 and has a larger diameter than that of the communication means 23.

The following describes this device in detail. However, the assay device of the present invention is not limited to the structure described in the following, and any other structure is applicable provided that it has the just described sample flow directions, specific binding reaction distribution and electrode arrangement.

The assay device shown in FIG. 22 comprises, from the upstream side toward the downstream side, an upper plate 22 having a sample-introducing hole 21, a sample-introducing means (a) made of filter paper and the like and a detection means (c). The detection means (c) has a through hole 29 in the direction of sample flow, a counter/reference electrode 24 is arranged along the periphery of the upper surface of the through hole 29, and a working electrode 24 is arranged along the periphery of the lower surface of the through hole 29. Making use of a reference electrode terminal 26, the counter/reference electrode 24 can be connected electrically to an external measuring instrument which is not shown in the drawing. The working electrode 25 can also be connected in the same manner using a working electrode terminal 27. Inside of the through hole 29 is communicated by a communication means 23 made of filter paper and the like, as a site for the liquid permeation from the sample-introducing means (a) to a matrix (b) which is arranged just under the through hole 29. The matrix (b) has a diameter larger than that of the through hole 29 and is composed of a membrane and the like to which antibody molecules are immobilized. Further downstream of the matrix (b) is an absorption means (d) on which a liquid-impermeable sealing means 28 is arranged. The sealing means 28 has a diameter larger than that of the through hole 29 but smaller than that of the matrix (b). The lowermost part of the assay device is supported by a support (e).

Figure 23A:
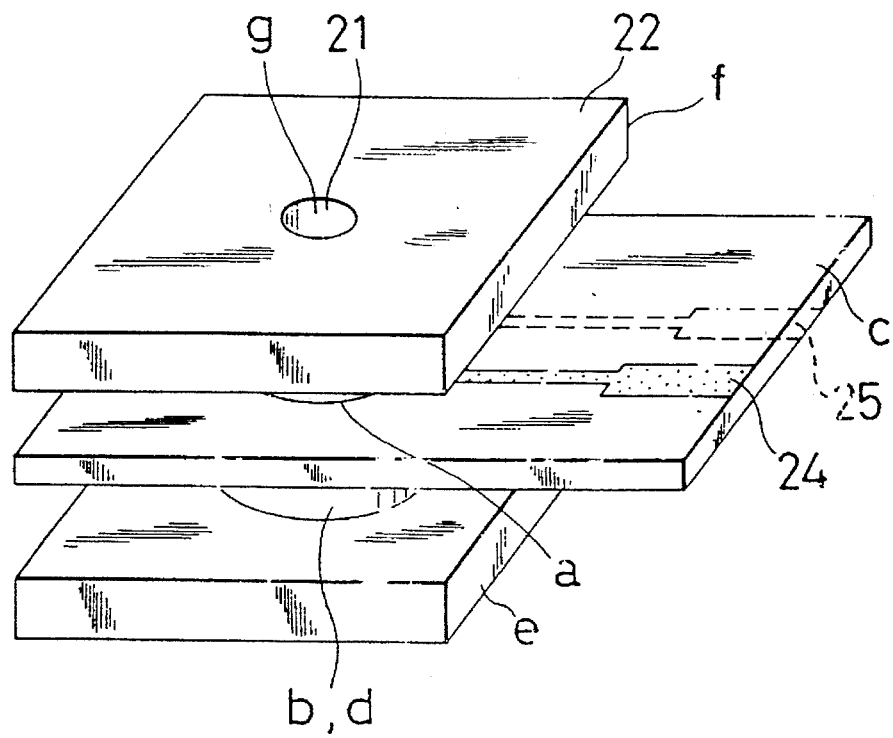
FIGS. 23A and 23B are a perspective diagram (A) or a section view (B) showing conditions of the assay device of FIG. 22 at the time of measurement.
Figure 23B:
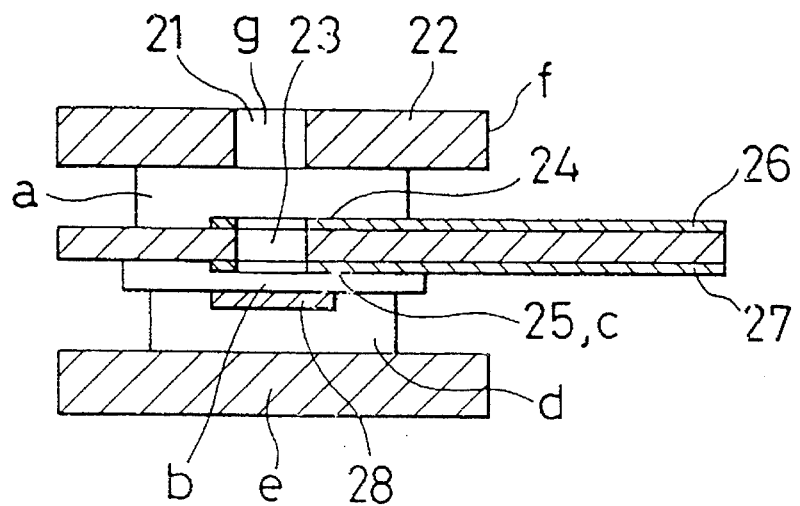

FIG. 23 (A) is a perspective diagram showing conditions of the specific binding assay device of FIG. 22 at the time of measurement, and FIG. 23 (B) is a section view of the device.

(1) Preparation of a conjugate of anti-hCGβ antibody and horseradish peroxidase (labeled antibody)

Mouse monoclonal antibody HM81 (Mochida Pharmaceutical Co., Ltd.) which recognizes the β chain of hCG was dissolved in a buffer solution consisting of 100 mM sodium chloride, 1 mM EDTA and 60 mM triethanolamine (pH 8.0, TEA buffer) to a final concentration of 8.3 mg/ml, and the resulting solution was dialyzed thoroughly against the TEA buffer which has been purged with nitrogen gas. A 61 μl portion of 50 mM 2-iminothiolane hydrochloride (Pierce Chemical Company) solution was added to 1.1 ml of the thus prepared antibody solution, and the mixture was stirred and then allowed to stand still for 1.5 hours at 4° C. in an atmosphere of nitrogen gas. Thereafter, the resulting solution was thoroughly dialyzed against a 100 mM phosphate buffer solution (pH 7.0) containing 100 mM sodium chloride and 1 mM EDTA (EDTA-PB) which has been purged with nitrogen gas. In this way, SH group-introduced anti-hCGβ antibody HM81 was obtained.

Horseradish peroxidase (HRPO, Toyobo Co., Ltd.) was dissolved in 100 mM phosphate buffer (pH 7.0) to a final concentration of 20 mg/ml. With stirring at 30° C., 500 μl of the thus prepared enzyme solution was mixed with 500 μl of 50 mM sulfo-SMCC (Pierce Chemical Company). After 20 minutes of reaction at 30° C., the resulting reaction mixture was passed through a Sephadex G-25 (Pharmacia K.K.) column (2.6φ×15 cm), which has been purged with nitrogen gas, to remove unreacted sulfo-SMCC and then concentrated using a concentrator (CENTRIPREP-10, Amicon Corp.) to obtain maleimidated HRPO. Concentration of the maleimidated HRPO was determined based on the absorbance at 403 nm.

A solution of the maleimidated HRPO ($1.25 \times 10^{-8}$ mole or $1.56 \times 10^{-8}$ mole) was mixed with the SH group-introduced HM81 antibody solution (3 times or ⅓ times in molar ratio), and the mixture was incubated at 4° C. for 12 hours in an atmosphere of nitrogen gas. After the reaction, 50 μl of 50 mM cysteamine solution was added to each of the reaction mixtures, and the reaction was continued at 4° C. for 60 minutes in an atmosphere of nitrogen gas. Thereafter, the resulting reaction mixture was subjected to gel filtration chromatography using an ULTROGEL AcA34 (IBF Biotechniques) column which have been equilibrated with EDTA-PB purged with nitrogen.

Each of the thus eluted fractions was checked for its absorbances at 280 nm and 403 nm, in order to collect and concentrate fractions containing the HM81/HRPO linked product but not containing free enzyme molecules. The thus concentrated preparation of the linked product (to be referred to as "HRPO-HM81" hereinafter) was checked for its molecular weight by a Phast system electrophoresis (Pharmacia K.K.) and used as a signal substance generator in measuring experiments.

(2) Preparation of anti-hCGα antibody-immobilized porous film

A total of 200 circular pieces (13 mm in diameter) of a porous membrane (cellulose acetate/cellulose nitrate) having a pore size of 8.0 μm (Cat. No. SCWP01300, Nippon Millipore Kogyo Co., Ltd.) were put in a beaker filled with 200 ml of a PBS solution containing 1.0% (w/v) of bovine γ globulin (Ca. No. G7516, Sigma Chemical Co.) and heated at 60° C. for 2 hours with gentle stirring. After removing the supernatant fluid and further removing the remaining liquid by suction, the thus treated circular pieces were washed by stirring them in a sufficient volume of PBS and then removing the used PBS. The washing step with PBS was further repeated twice, and the washed pieces were again washed with distilled water 7 times. After completion of the washing steps, the circular pieces were put in 200 ml of 1.0% glutaraldehyde aqueous solution and incubated at 25° C. for 3 hours with gentle stirring. After the reaction, the thus treated circular pieces of the porous membrane were washed with distilled water 10 times and then arranged on a glass plate one by one to dry them. Separately from this, mouse monoclonal antibody HM21 (Mochida Pharmaceutical Co., Ltd.) which recognizes the α chain of hCG was dissolved in a solution consisting of 0.05M sodium bicarbonate and 0.05M sodium chloride to a final concentration of 1.0 mg/ml. Each piece (13 mm in diameter) of the porous membrane dried on a glass plate was impregnated with 25 μl of the just prepared antibody solution from the central portion of the circular piece. After 1 hour of reaction at room temperature, the resulting circular pieces of the porous membrane were put in 200 ml of a 0.2% bovine serum albumin (BSA)/PBS solution and shaken at 4° C. for 2 days to effect blocking. Thereafter, the thus treated pieces were washed three times with a 0.1% Tween 20/PBS solution and then seven times with PBS to obtain anti-hCGα antibody (HM21)-immobilized porous membrane.

(3) Preparation of a detection means (electrode)

On each of the face side and back side of a transparent vinyl chloride plate (40 mm in length, 20 mm in width and 0.3 mm in thickness) were printed a circular area (6 mm in diameter) and an electrode terminal line (1.5 mm in width) connected to the circular area, using a conductive carbon ink (Electrodag 109. available from Acheson Japan, Ltd). In this instance, the circular area having a diameter of 6 mm on the face side and the other circular area on the back side were printed at the same point of the vinyl chloride plate (cf. FIG. 22). On the face side circular area was further printed a conductive silver ink (Fujikura Kasei Co., Ltd.). Thereafter, a hole having a diameter of 3 mm was made on the center of the circular area using a punch for the purpose of using it as a through hole, and the ring zones remaining on both face side and back side circular areas after the punching were used as conductive portions. After the punching, it was confirmed that the face side conductive portion and the back side conductive portion were electrically independent from each other. Thereafter, the conductive silver ink-superposed portion was subjected to 2 hours of electrolysis in 0.1M sodium chloride aqueous solution (+1.0 V vs silver/silver chloride electrode) to form a silver chloride layer on the surface. The face side and back side areas of the plastic plate were sealed by sticking a mending tape (Sumitomo 3M Co., Ltd.), excluding the ring zones and the terminal lines. Of the exposed ring zones, the face side ring zone laminated with a silver/silver chloride layer was used as a counter/reference electrode, and the other ring zone made of only conductive carbon was used as a working electrode. The thus prepared working electrode was used as a detection means in the measuring experiments.

(4) Preparation of a specific binding assay device having a sample-introducing means and an absorption matrix, in which a single layer of the anti-hCGα antibody-immobilized porous membrane is arranged under the working electrode (cf. FIG. 22)

Two circular pieces having a diameter of 12 mm were punched out from a chromatographic filter paper (17 Chr, Whatman Corp.) and superposed as an absorption means on a lower support made of an acrylate resin. To the central part of the surface of the upper layer of the circular filter papers was applied a seal having a diameter of 6 mm which has been prepared by punching a mending tape (Sumitomo 3M Co., Ltd.). A circular piece (13 mm in diameter) of the anti-CGα antibody (HM21)-immobilized porous membrane prepared in Example 8 (2) was dried and superposed on the central position of the absorption means (filter paper) equipped with a sealing means, and the porous membrane was used as a matrix portion. The detection means (electrode) prepared in Example 8 (3), with its silver/silver chloride electrode-possessing side being the upper side, was superposed on the matrix portion in such a manner that the central point of the 3 mm diameter through hole of the detection means coincided with that of the circular porous membrane of the matrix portion. A circular piece having a diameter of 3 mm was punched out from a glass fiber filter paper (GF75, Advantech Toyo Co., Ltd.) and inserted in the through hole of the electrode to use as a communication means. A circular piece having a diameter of 12 mm was punched out from a glass fiber filter paper (GA200, Advantech Toyo Co., Ltd.) and superposed, as a sample-introducing means, on the electrode in such a manner that the central point of the circular piece coincided with that of the through hole of the electrode. On the thus prepared sample-introducing means was further superposed an upper plate (5 mm in thickness) made of an acrylic resin having a sample-introducing hole (4 mm in diameter) in such a manner that the central point of the sample-introducing hole coincided with that of the circular sample-introduction means (filter paper). In this way, a specific binding assay device for use in the measurement of hCG concentration was constructed (cf. FIGS. 22 and 23A–23B). In this instance, the distance between the lower surface of the upper plate and the upper surface of the lower support was adjusted to 3,200 μm. This device is close to the type shown in FIG. 9 (G).

(5) Measurement

The assay device thus constructed was connected with necessary measuring equipment such as a potentiostat and the like as described in Example 1 (6), using the carbon ring side as a working electrode and the silver/silver chloride ring side as counter/reference electrode.

Each of five test samples containing different amounts of hCG was mixed the same volume of a HRPO-HM81 solution which has been adjusted to an antibody-based concentration of 0.1 μg/ml using a 100 mM sodium chloride/0.1M phosphate buffer /pH 6.0) supplemented with 0.1% BSA (PB for reaction use). A 285 μl portion of the thus prepared mixture solution was mixed thoroughly with 12.5 μl of a 2.5 mM p-benzoquinone solution prepared using 100 mM sodium chloride/0.1M phosphate buffer (pH 6.0) and further with 12.5 μl of about 0.25M hydrogen peroxide solution prepared using 100 mM sodium chloride/0.1M phosphate buffer (pH 6.0). In this way, a solution (A) having an hCG concentration of 0 IU/l, a solution (B) having an hCG concentration of 1 IU/l, a solution (C) having an hCG concentration of 10 IU/l, a solution (D) having an hCG concentration of 100 IU/l and a solution (E) having an hCG concentration of 1000 IU/l were prepared, each solution containing 0.046 μg/ml of HRPO-HM81 in antibody-based concentration, 100 μM of p-benzoquinone and about 10 mM of hydrogen peroxide.

A 260 μl portion of each of the solutions (A), (B), (C), (D) and (E) was introduced into (spotted on) the sample-introducing means through the sample-introducing hole of the upper acrylic plate of the specific binding assay device. When the the test sample permeated into the matrix and further into the water absorption matrix (1 minute after the sample introduction), an electric potential of −200 mV was applied to the working electrode based on the counter/reference electrode to record electric current.

(6) Results

Table 8 shows changes in the electric current 3 minutes after the application of the electric potential to the working electrode. The electric current became high in response to the concentration of hCG. On the basis of these results, it was confirmed that quantitative determination of the concentration of hCG in a test sample can be made easily and quickly by the use of the assay device of the present invention.

TABLE 8

| Relationship between the hCG concentration in reaction solution and the electric current measured | |
|---|---|
| Conc. of hCG in reaction solution (IU/l) | Electric current (nA) after 3 min. |
| 0 | 960 |
| 1 | 1000 |
| 10 | 1030 |
| 100 | 1080 |
| 1000 | 1270 |

Thus, it is apparent that there have been provided, according the present invention, a simple general purpose process useful for quick qualitative or quantitative assay, which is a homogeneous method based on the principle of a specific binding assay, but which does not require a step for the separation of unreacted substances, and a specific binding assay, device suitable for the practice of the process.

The assay process of the present invention can be applied to various specific binding reactions including a sandwich type reaction, a competition type reaction and the like, independent of the properties of test samples and the properties of substances to be assayed such as molecular weight and the like, and judgment of the results can be effected based on a coloring reaction, a fluorescence reaction, a luminescence reaction, an electrochemical reaction and the like. That is, the assay process of the present invention can be applied to various assay modes, because the results can be detected or measured by visual observation or using an appropriate external measuring instrument corresponding to the property of the generated signal.

In addition, the assay device of the present invention can be made into any mode suitable for the purpose of each measurement, such as minimization of its size, because the inventive assay device is not limited by the shape and size of its matrix and arrangement of its detection means. In consequence, the assay device can be used even when a test sample is available only in a trace quantity. In addition, the assay device of the present invention can be used as a disposable device, because it can easily be connected to and disconnected from an external measuring instrument.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. An electrochemical competitive specific binding assay process for measuring the amount of a substance to be assayed in a liquid test sample, comprising the steps of:

(a) providing a kit comprising:

a matrix through which said liquid test sample can flow in a predetermined direction, wherein a specific binding substance which can specifically bind to or compete with said substance to be assayed in said liquid test sample is immobilized, sample introducing means connected to said matrix, and detection means connected to said matrix for detecting an electrical signal which is generated when a signal substance contacts said detection means, wherein said detection means is distinct from said immobilized specific binding substance;

(b) introducing a labeled binding substance into said matrix together with said liquid test sample, wherein said labeled binding substance can specifically bind with said immobilized specific binding substance and generate said signal substance, causing said liquid test sample and said labeled binding substance to flow in a predetermined direction through said matrix, and causing said substance to be assayed and said labeled binding substance to bind competitively with said immobilized specific binding substance or causing said substance to be assayed and said immobilized specific binding substance to bind competitively with said labeled binding substance thereby trapping a portion of said labeled binding substance in said matrix, and forming a distribution of said labeled binding substance in the predetermined direction, wherein the distribution of said trapped portion depends upon the amount of said substance to be assayed in said liquid test sample;

(c) measuring the intensity of said electrical signal from said signal substance which diffuses from said labeled binding substance towards said detection means without a step for separating bound and free reactants produced by the binding of said labeled binding substance to said immobilized specific binding substance; and (d) determining the amount of said substance to be assayed by comparing said electrical signal to reference values.

2. An electrochemical sandwich specific binding assay process for measuring the amount of a substance to be assayed in a liquid test sample, comprising the steps of:

(a) providing a kit comprising:

a matrix through which said liquid test sample can flow in a predetermined direction, wherein a specific binding substance which can specifically bind with a first region of said substance to be assayed in said liquid test sample is immobilized, sample introducing means connected to said matrix, and detection means connected to said matrix for detecting an electrical signal which is generated when a signal substance contacts said detection means, wherein said detection means is distinct from said immobilized specific binding substance;

(b) introducing a labeled binding substance into said matrix together with said liquid test sample, wherein said labeled binding substance can specifically bind with a second region of said substance to be assayed and generate said signal substance, causing said liquid test sample and said labeled binding substance to flow in a predetermined direction through said matrix, and causing said substance to be assayed to bind with said immobilized specific binding substance thereby trapping a portion of said labeled binding substance in said matrix, and forming a distribution of said labeled binding substance in the predetermined direction, wherein the distribution of said trapped portion depends upon the amount of said substance to be assayed in said liquid test sample;

(c) measuring the intensity of said electrical signal from said signal substance which diffuses from said labeled binding substance towards said detection means without a step for separating bound and free reactants produced by the binding of said labeled binding substance to said substance to be assayed and the binding of said substance to be assayed to said immobilized specific binding substance; and (d) determining the amount of said substance to be assayed by comparing said electrical signal to reference values.

3. The assay of claims 1 or 2, wherein said detection means is upstream of said matrix.

4. The assay of claims 1 or 2, wherein said detection means is downstream of said matrix.

5. The assay of claim 1 or 2, wherein said labeled binding substance is an enzyme-labeled specific binding substance.

6. The assay of claim 1 or 2, wherein said matrix is a porous material.

7. The assay of claim 1, wherein said substance to be assayed is an antigen, said labeled binding substance is the antigen or an analog thereof which is labeled and said immobilized specific binding substance is an antibody of said antigen or the analog thereof.

8. The assay of claim 1, wherein said substance to be assayed is an antibody of an antigen, said labeled binding substance is an antibody of said antigen or an analog thereof which is labeled and said immobilized specific binding substance is said antigen or an analog thereof.

9. The assay of claim 1, wherein said substance to be assayed is an antigen, said labeled binding substance is an antibody of said antigen or an analog thereof which is labeled and said immobilized specific binding substance is said antigen or an analog thereof.

10. The assay of claim 1, wherein said substance to be assayed is an antibody of an antigen, said labeled binding substance is the antigen or an analog thereof which is labeled and said immobilized specific binding substance is an antibody of said antigen or an analog thereof.

* * * * *

UNITED STATES PATENT AND TRADEMARK OFFICE
CERTIFICATE OF CORRECTION

PATENT NO. : 5,516,644  
DATED : May 14, 1996  
INVENTOR(S) : Yamauchi et al

Page 1 of 2

It is certified that error appears in the above-indentified patent and that said Letters Patent is hereby corrected as shown below:

Column 14  
    line 3 after "(b)" insert --The upper tracing corresponds to frequent formation of a signal substance generator in the state of Fig. 1B. The lower tracing corresponds to frequent formation of signal substance generator in the state of Fig. 1A.--

Column 37  
    line 62 after "mIU/ml." insert --In Fig. 12, the activity in each layer in the absence of antigens was expressed as 100%.--

Column 39  
    line 60 after "(b)." insert --Each tracing indicates the position of the enzyme in a particular layer.--

UNITED STATES PATENT AND TRADEMARK OFFICE
CERTIFICATE OF CORRECTION

PATENT NO. : 5,516,644

DATED : May 14, 1996

INVENTOR(S) : Yamauchi et al

It is certified that error appears in the above-indentified patent and that said Letters Patent is hereby corrected as shown below:

Column 41
    line 46 after "Fig. 16." insert --Each tracing indicates the position of the HRPO in a particular layer.--

Column 42
    line 41 after "Fig 18." insert --Each tracing indicates the position of the GOD in a particular layer.--

Column 43
    after "Fig 20." insert --Each tracing indicates the position of the GOD in a particular layer.--

Signed and Sealed this

Nineteenth Day of November, 1996

Attest:

BRUCE LEHMAN

Attesting Officer     Commissioner of Patents and Trademarks